US008309601B2

(12) United States Patent
Walling et al.

(10) Patent No.: US 8,309,601 B2
(45) Date of Patent: Nov. 13, 2012

(54) FORMS OF CDDO METHYL ESTER

(75) Inventors: John Walling, Irving, TX (US); Stephan D. Parent, W. Lafayette, IN (US); David T. Jonaitis, Lafayette, IN (US); Robert M. Kral, Jr., Grapevine, TX (US)

(73) Assignee: Reata Pharmaceuticals, Inc., Irving, TX (US)

( * ) Notice: Subject to any disclaimer, the term of this patent is extended or adjusted under 35 U.S.C. 154(b) by 0 days.

(21) Appl. No.: 13/306,043

(22) Filed: Nov. 29, 2011

(65) Prior Publication Data

US 2012/0071684 A1 Mar. 22, 2012

Related U.S. Application Data

(63) Continuation of application No. 12/191,176, filed on Aug. 13, 2008, now Pat. No. 8,088,824.

(60) Provisional application No. 60/955,939, filed on Aug. 15, 2007.

(51) Int. Cl.
*A61K 31/21* (2006.01)
(52) U.S. Cl. ........................................ 514/510
(58) Field of Classification Search ................ None
See application file for complete search history.

(56) References Cited

U.S. PATENT DOCUMENTS

| 5,064,823 | A | 11/1991 | Lee et al. |
| 6,326,507 | B1 | 12/2001 | Gribble et al. |
| 6,890,946 | B2 | 5/2005 | Nakshatri et al. |
| 2003/0119732 | A1 | 6/2003 | Konopleva et al. |
| 2004/0002463 | A1 | 1/2004 | Honda et al. |
| 2005/0276836 | A1 | 12/2005 | Wilson et al. |
| 2006/0007097 | A1 | 1/2006 | Ichikawa |

FOREIGN PATENT DOCUMENTS

| DE | 102005041613 A1 | 3/2007 |
| WO | WO-2007/069895 A1 | 6/2007 |

OTHER PUBLICATIONS

Andrew E. Place et al., "The Novel Synthetic Triterpenoid, CDDO-Imidazolide, Inhibits Inflammatory Response and Tumor Growth in Vivo", Clinical Cancer Research, vol. 9, 2798-2806, Jul. 2003.
Bruker Advanced X-Ray Solutions, "Xprep Reciprocal Space Exploration for Macromoleucles", v. 6.12., Bruker AXS Inc. Mad. WI, 2002, 2 pgs.
Deliang Zhou et al., "Physical Stability of Amorphous Pharmaceuticals: Importance of Configurational Thermodynamic Quantities and Molecular Mobility", Journal of Pharmaceutical Sciences, vol. 91, No. 8, Aug. 2002, pp. 1863-1872.
Design and Evaluation of an Orally Administered Formulation, published on Feb. 10, 1995, pp. 172-179.
G. M. Sheldrick, "The SHELX-97 Manual—A Program for Crystal Structure Refinement", University of Gottingen Germany, 1997, pp. 1-1-20-1.
Ian J. Bruno et al., "New Software for searching the Cambridge Structural Database and visualizing crystal structures", Acta Cryst. (2002) B58, 389-397.
International Search Report PCT/US08/09703.
International Tables for Crystallography, vol. C, Tables 4.2.6.8 and 6.1.1.4. Kluwar Academic Publishers: Dordrecht, The Netherlands, (1992).
Lothar Bore et al., "The anti-inflammatory triterpenoid methyl 2-cyano-3, 12-dioxooleana-1,9(11)-dien-28-oate methanol solvate hydrate", Acta Cryst. (2002) C588, 0199-0200.
Louis J. Farrugia, "ORTEP-3 for Windows—a version of ORTEP-III with a Graphical User Interface (GUI)", j. Appl. Cryst. (1997) 30, 565.
Michael N. Burnett et al., "ORTEP-III: Oak Ridge Thermal Ellipsoid Plot Program for Crystal Structure Illustrations", Chemical and Analytical Sciences Division, Report ORNL-6895, Oak Ridge National Laboratory, TN, USA, 1996, pp. 1-90.
Michael Repka et al., "Hot-Melt Extrusion Technology", Encyclopedia of Pharmaceutical Technology, Second Edition, vol. 2, (Marcel Dekker, 2002), pp. 203-206.
Non-Final Office Action U.S. Appl. No. 12/191,176 dated Apr. 7, 2011.
Non-Final Office Action U.S. Appl. No. 12/191,176 dated Sep. 21, 2010.
Notice of Allowance U.S. Appl. No. 12/191,176 dated Aug. 31, 2011.
Notice of Reasons for Rejection Japanese Patent Application No. 2010-521031 dated Mar. 29, 2011.
Supplementary European Search Report EP 08 79 53030 dated Jul. 9, 2010.
Tadashi Honda et al., "A Novel Dicyanotriterpoenoid, 2-Cyano-3,12-dioxooleana-1,9(11)-dien-28-onitrile, Active at Picomolar Concentrations for Inhibition of Nitric Oxide Production", Bioorganic & Medicinal Chemistry Letters, 12 (2002) 1027-1030.
Tadashi Honda et al., "Design and Synthesis of 2-Cyano-3,12-Dioxoolean-1,9-Dien-28-Oic Acid, A Novel and Highly Active Inhibitor of Nitric Oxide Production in Mouse Macrophages", Bioorganic & Medicinal Chemistry Letters 8 (1998) 2711-2714.
Tadashi Honda et al., "New Encore Derivatives of Oleanolic Acid and Ursolic Acid As Inhibitors of Nitric Oxide Production in Mouse Macrophages", Bioorganic & Medicinal Chemistry Letters, vol. 7, No. 13, pp. 1623-1628, 1997.
Tadashi Honda et al., "Novel Synthetic Oleanane and Ursane Triterpenoids with Various Enone Functionalities in Ring A as Inhibitors of Nitric Oxide Production in Mouse Macrophages", J. Med. Chem., 2000, 43, 1866-1877.
Tadashi Honda et al., "Synthetic Oleanane and Ursane Triterpenoids with Modified Rings A and C: A Series of Highly Active Inhibitors of Nitric Oxide Production in Mouse Macrophages", J. Med. Chem. 2000, 43, 4233-4246.

(Continued)

*Primary Examiner* — Elli Peselev
(74) *Attorney, Agent, or Firm* — Foley & Lardner LLP

(57) ABSTRACT

A triterpenoid compound, methyl 2-cyano-3,12-dioxoleana-1,9(11)-dien-28-oate (CDDO methyl ester), has a non-crystalline, glassy solid form and a non-hydrous crystalline form that can prepared, for example, from a saturated methanol solution. The glassy form displays an enhanced bioavailability over the non-hydrous crystalline form. Each form of CDDO methyl ester is a superior candidate for use, typically in solid dosage form, for treating a variety of disease states, generally associated with inflammation.

9 Claims, 30 Drawing Sheets

OTHER PUBLICATIONS

W. Kraus et al., Powdercell for Windows Version 2.3, Federal Institute for Materials Research and Testing, Berlin, Germany, 1999.

Yong Cui, "A material science perspective of pharmaceutical solids", International Journal of Pharmaceutics 339 (2007) 3-18.

Zbyszek Otwinowski et al., "[20] Processing of X-Ray Diffraction Data Collected in Oscillation Mode", Methods in Enzymology vol. 276, 1997, pp. 307-326.

Chilean Patent Application No. 2417-2008, Office Action dated Jun. 17, 2012.

DSC $P4_32_12$ (#96)

FORMS OF CDDO METHYL ESTER

CROSS-REFERENCE TO RELATED PATENT APPLICATIONS

This application is a Continuation Application of U.S. Ser. No. 12/191,176, filed Aug. 13, 2008, now U.S. Pat. No. 8,088,824, which claims priority from U.S. Provisional Application 60/955,939, filed Aug. 15, 2007. Each of the above is incorporated herein by reference in entirety.

BACKGROUND OF THE INVENTION

Triterpenoids are biosynthesized in plants by the cyclization of squalene. Although candidates for medicinal use, these naturally occurring molecules display relatively weak biological activity. Accordingly, chemists have sought to synthesize analogues of enhanced potency (Honda et al., 1997 & 1998).

Several synthetic analogs are reported to suppress the de novo formation of iNOS and COX-2 in macrophages that have been stimulated by IFN-γ or LPS (Suh et al., 1998; Honda et al., 2002). Another synthetic triterpenoid, 2-cyano-3,12-dioxoleana-1,9(11)-dien-28-oate (CDDO), exhibits anti-inflammatory and anti-proliferative activity (Honda et al., 1998 & 2000).

Studying the methyl ester of CDDO, which is methyl 2-cyano-3,12-dioxoleana-1,9(11)-dien-28-oate (CDDO methyl ester), Bore et al. (2002) determined a crystal structure. In that form, which is hydrated, water coordinates interactions that engender a particular crystal packing and structure.

SUMMARY OF THE INVENTION

In one embodiment of the present invention, a non-hydrous crystalline form of CDDO methyl ester is provided. The non-hydrous crystal form preferably has a space group of $P4_32_12$ with unit cell dimensions of a=14.2 Å, b=14.2 Å, and c=81.6 Å. The invention also contemplates a pharmaceutical composition in solid dosage form, comprising (i) a therapeutically effective amount of a non-hydrous crystalline form of CDDO methyl ester with (ii) an edible carrier.

Additionally, the present invention is embodied in a glassy solid form of CDDO methyl ester, having an x-ray powder diffraction pattern with a halo peak at approximately 13.5°2θ, as shown in FIG. 2C, and a glass transition temperature ($T_g$). In particular embodiments, the $T_g$ can range from about 120° C. to about 135° C. In other embodiments, the $T_g$ ranges from about 125° C. to about 130° C. The glassy solid form of CDDO-methyl ester can have a PDF spectrum with similar peaks to FIG. 28 from about 5 Å to about 20 Å.

Furthermore, the invention provides a pharmaceutical composition in solid dosage form, comprising (i) a therapeutically effective amount of a glassy solid form of CDDO methyl ester with (ii) an edible carrier. In this regard, the invention contemplates a methodology for treating a cancer patient, comprising: administering such a pharmaceutical composition to a cancer patient. The invention also contemplates administering the glassy form of CDDO-methyl ester in combination with another anti-cancer drug. For example, the anti-cancer drug may be gemcitabine and the cancer may be pancreatic cancer. The invention encompasses as well a methodology for the treatment of diseases or disorders that involve acute or chronic oxidative stress and inflammation, particularly those characterized in part by overexpression of inducible nitric oxide synthase (iNOS) or inducible cyclooxygenase (COX-2).

In addition, the invention is drawn to a dimethanol solvate form of CDDO-methyl ester, having an x-ray powder diffraction pattern with characteristic peaks as shown in Table 18 and a DSC pattern as shown in FIG. 24. Pursuant to the invention, the dimethanol solvate form may be used as an intermediate for the production of a glassy solid form of CDDO methyl ester. A method for the production of the glassy solid form of CDDO-methyl ester, via the dimethanol solvate form, comprises preparing a dimethanol solvate form of CDDO-methyl ester and drying the dimethanol solvate form.

In accordance with another embodiment, the invention is drawn to a method of growing a crystal of CDDO methyl ester dimethanolate, comprising preparing a solution of purified CDDO methyl ester in warm anhydrous methanol, adding the warm solution to a vessel of chilled methanol, and filtering the resulting crystals.

In accordance with another embodiment, the invention is drawn to a pharmaceutical composition comprising (i) a therapeutically effective amount of CDDO-methyl ester and (ii) an excipient that is a glass former, such that the composition has a $T_g$.

The excipient may be selected, for instance, from the group consisting of (A) a carbohydrate, carbohydrate derivative, or carbohydrate polymer, (B) a synthetic organic polymer, (C) an organic acid salt, (D) a protein, polypeptide, or peptide, and (E) a high molecular weight polysaccharide. Illustrative of the class of synthetic organic polymer excipients are a hydroxpropyl methyl cellulose, such as hydroxypropyl methyl cellulose phthalate ester, a poly[1-(2-oxo-1-pyrrolidinyl)ethylene or copolymer thereof, such as PVP/VA, and a methacrylic acid copolymer, such as methacrylic acid—ethyl acrylate copolymer (1:1).

Another exemplary excipient in this regard is copovidone, which is 1-vinyl-2-pyrrolidone-vinyl acetate copolymer (3:2).

DETAILED DESCRIPTION OF THE PREFERRED EMBODIMENTS

As noted, the study of triterpenoids as suppressors of iNOS activity, and specifically in the inhibition of NO production, has demonstrated the high potency of CDDO and CDDO methyl ester ($IC_{50}$<1 nM level). See Honda et al. (2000). These studies focused on solubilized CDDO methyl ester, providing little characterization of a solid of CDDO methyl ester. The work of Bore et al. (2002) elucidated a structure, the first published for a triterpenoid, of a single, solvated crystalline form of CDDO methyl ester.

Figure 1:
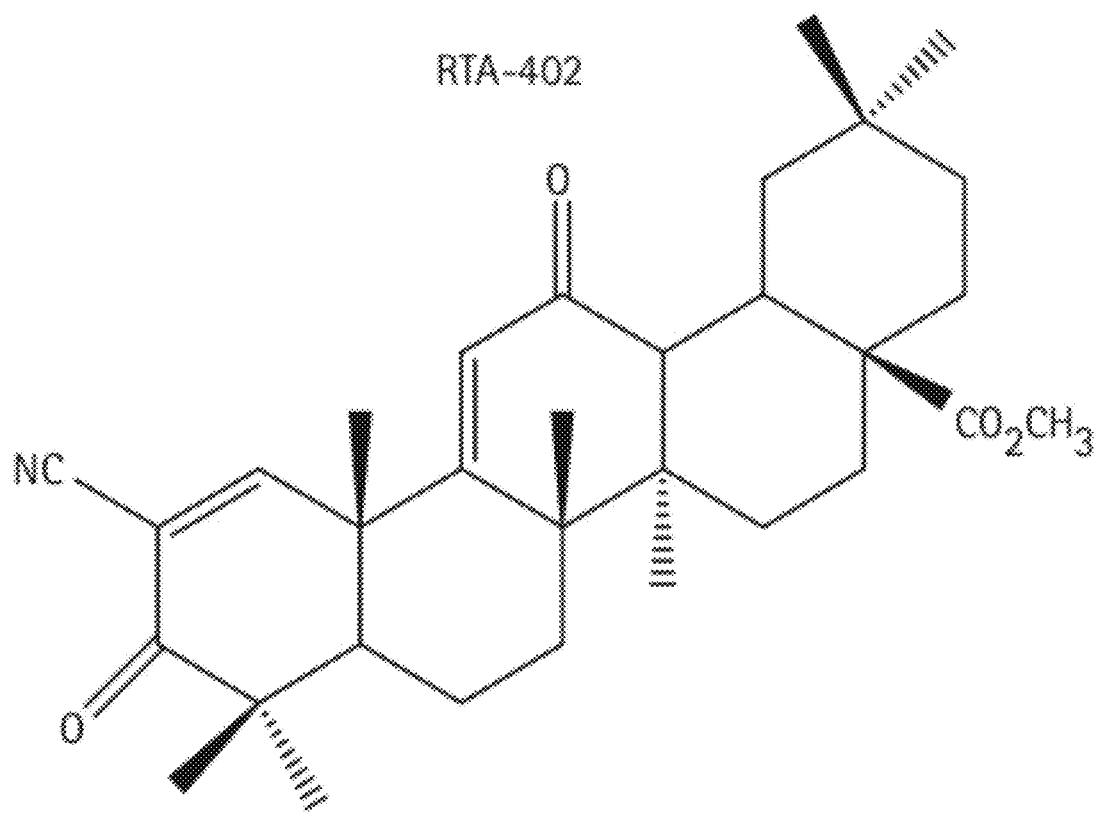
FIG. 1 depicts the chemical structure of CDDO methyl ester.
Figure 12:
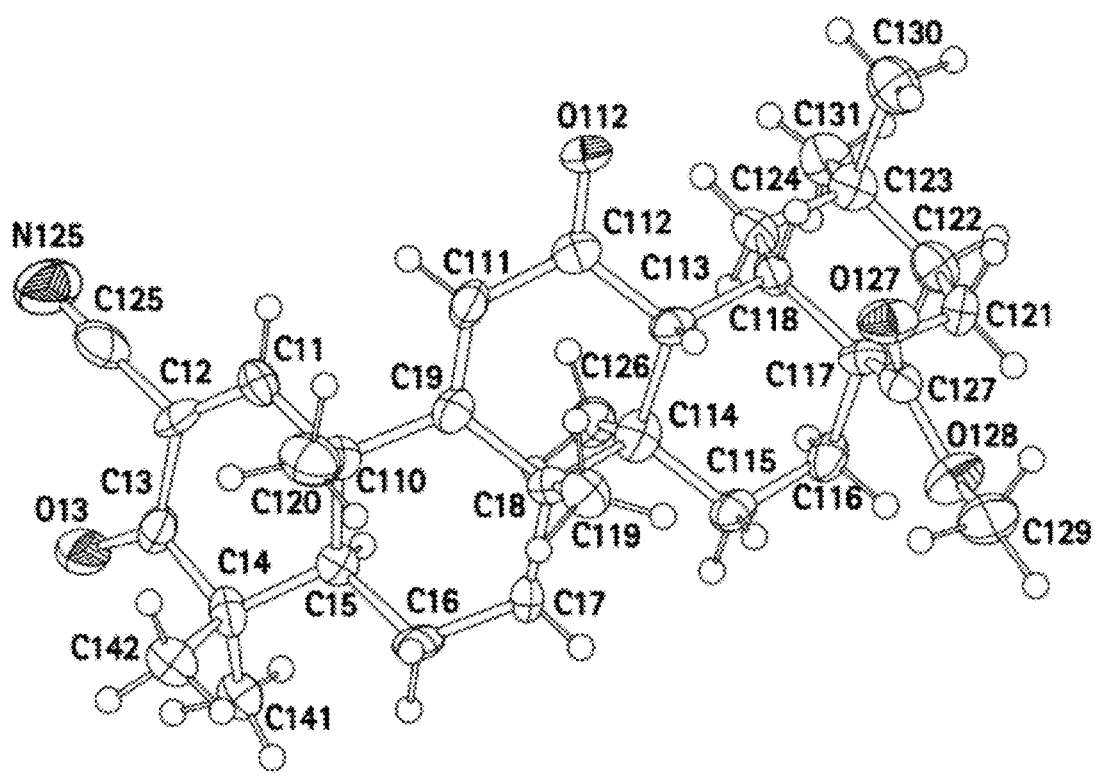
FIG. 12 shows an ORTEP drawing of a single Form A molecule with labeling. Atoms are represented by 50% probability anisotropic thermal ellipsoids.

To realize the therapeutic potential of CDDO methyl ester, depicted in FIG. 1 (chemical structure) and in FIG. 12 (ORTEP drawing), the present inventors investigated other forms of the compound that possessed properties, such as greater aqueous solubility and chemical stability, that are advantageous to development of a medicinal product with suitable pharmacokinetics. Consequently, the inventors discovered two forms of CDDO methyl ester, distinct from the crystal form elucidated by Bore et al. (2002), that have such properties and, hence, are candidates for drug development in their own right.

Figure 14:
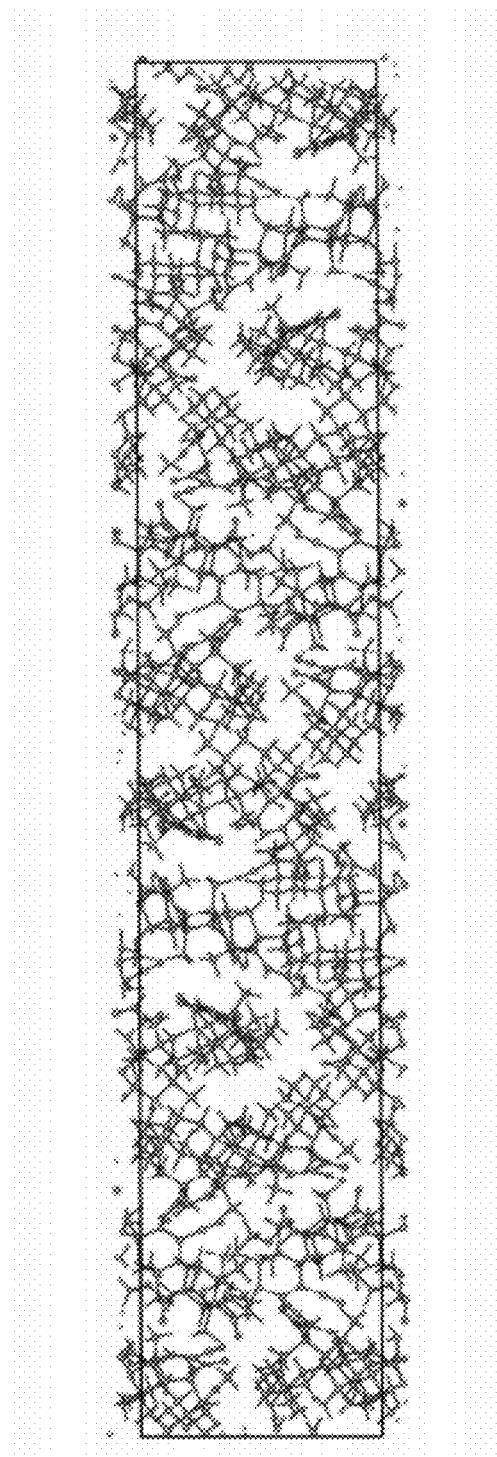
FIG. 14 shows a packing diagram of Form A crystals viewed down the crystallographic a axis.
Figure 15:
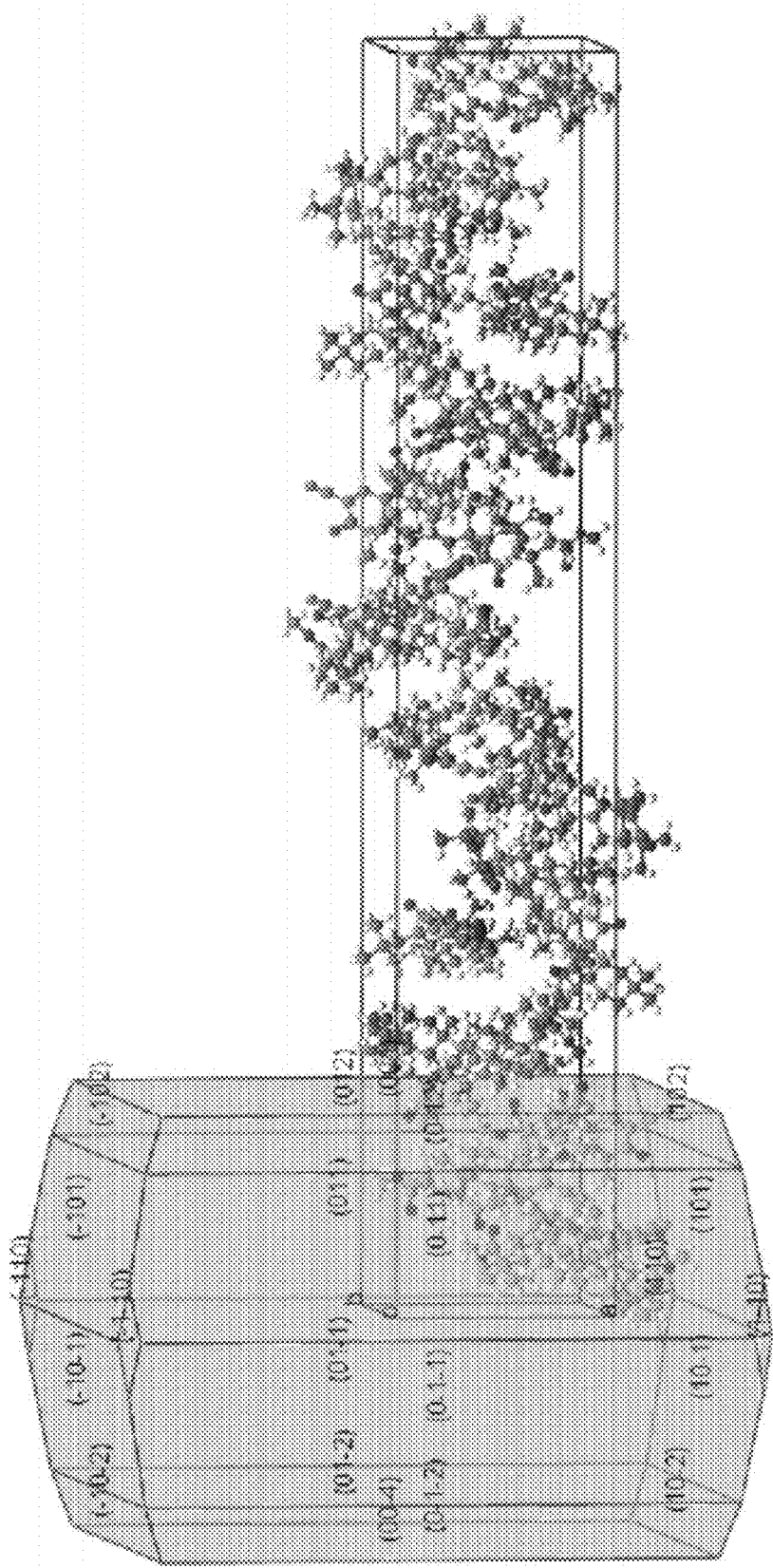
FIG. 15 shows a packing diagram of Form A crystals viewed down the crystallographic b axis.
Figure 16:
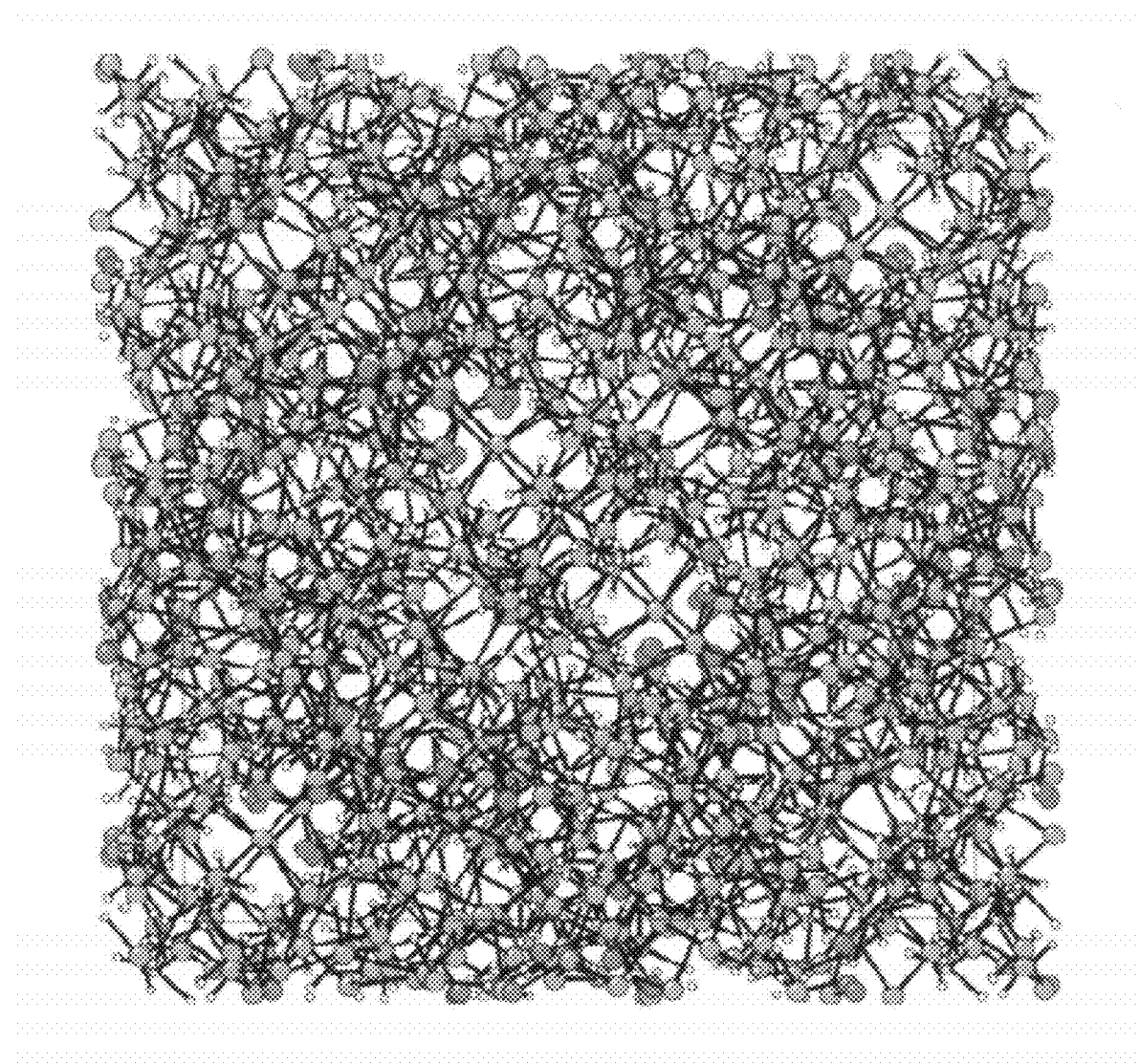
FIG. 16 shows a packing diagram of Form A crystals viewed down the crystallographic c axis.
Figure 29:
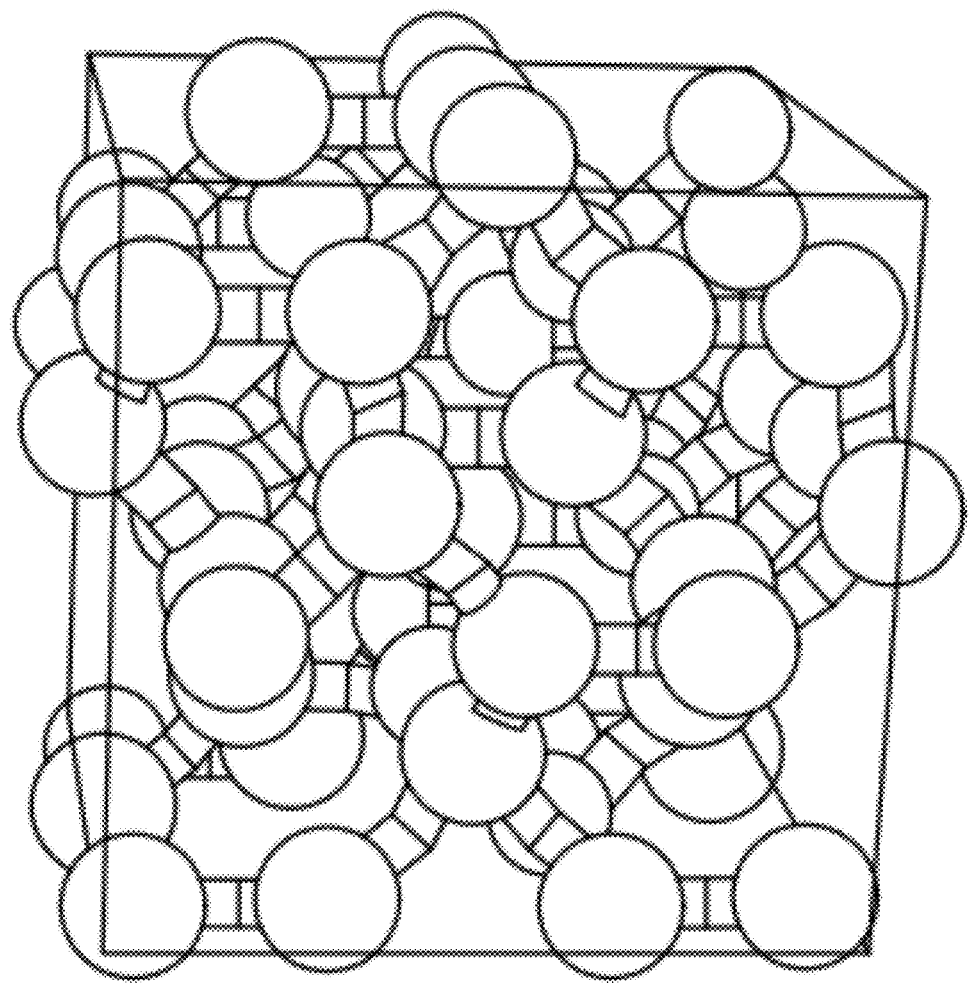
FIG. 29 is a schematic representation of space group $P4_32_12$ (#96).

Inventive "Form A" of CDDO methyl ester is unsolvated (non-hydrous) and is characterized by a distinctive crystal structure, with a space group of $P4_32_12$ (no. 96), shown in FIG. 29, unit cell dimensions of a=14.2 Å, b=14.2 Å and c=81.6 Å, and by a packing structure, depicted in FIGS. 14-16, whereby three molecules are packed in helical fashion down the crystallographic b axis. Table 10 below enumerates additional crystal data for Form A, along with crystallographic data-collection parameters.

The other "Form B" of the invention is in a single phase but lacks such a defined crystal structure. Rather, Form B is typified by an x-ray powder diffraction (XRPD) spectrum differing from that of Form A (see FIG. 2, inter alia). Moreover, Form B displays a bioavailability that is surprisingly better than that of Form A (see Example 7).

Methodology for the synthesis of CDDO methyl ester has been published. See U.S. Pat. No. 6,326,507, Honda et al. (1998), and Honda et al. (2000). The inventors have discovered that both Form A and Form B of CDDO methyl ester are readily prepared from a variety of solutions of the compound, illustrated by those detailed in Table 3-5, infra. In particular, Form B can be prepared by fast evaporation or slow evaporation in MTBE, THF, toluene, or ethyl acetate. By the same token, Form A can be prepared via fast evaporation, slow evaporation, or slow cooling of a CDDO methyl ester solution in ethanol or methanol. Preparations of CDDO methyl ester in acetone can produce either Form A, using fast evaporation, or Form B, using slow evaporation. Additional preparation methods are described below, including the tables provided there.

Since it does not have a defined crystal structure, Form B likewise lacks distinct XRPD peaks, such as those that typify Form A, and instead is characterized by a general "halo" XRPD pattern. In particular, the non-crystalline Form B falls into the category of "x-ray amorphous" solids because its XRPD pattern exhibits three or fewer primary diffraction halos (see FIG. 10, for instance). Within this category, Form B is a "glassy" material: As shown by the PDF, the nearest neighbor atom-atom interactions match that observed for crystalline Form A, but the notion of an average unit cell does not apply because there is no long-range order manifested.

Figure 27:
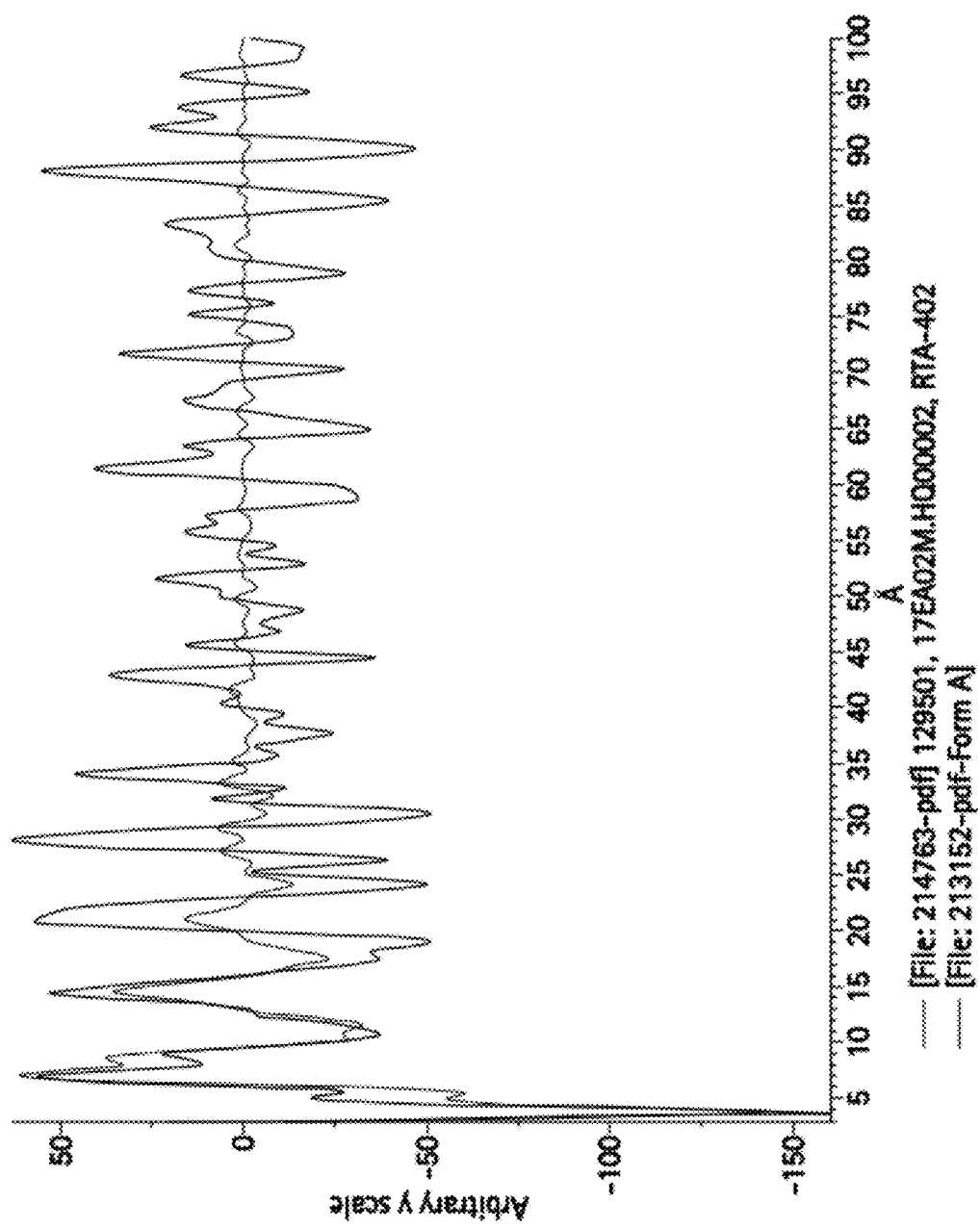
FIG. 27 is an overlay representation of PDF data for Form A vs. Form B Local order is similar from about 5 Å to about 20 Å.

Unlike Form A, therefore, samples of Form B show no long-range molecular correlation, i.e., above roughly 20 Å (see FIG. 27). Moreover, thermal analysis of Form B samples reveals a glass transition temperature ($T_g$). In contrast, a disordered nanocrystalline material, does not display a $T_g$ but instead only a melting temperature ($T_m$), above which crystalline structure becomes a liquid.

The present description also characterizes a CDDO-methyl ester dimethanol solvate form that can be used to prepare form B (see Example 9). Also characterized here is a CDDO-methyl ester hemibenzenate form (see Example 8).

Although micronization of other crystalline materials has been found to affect XRPD spectra, XRPD analysis of micronized Form A results in a spectrum similar to unmicronized Form A. See FIG. 2 for a side-by-side comparison of unmicronized Form A, micronized Form A, and Form B CDDO methyl ester.

Various means of characterization can be used together to distinguish Form A and Form B CDDO methyl ester from each other and from other forms of CDDO methyl ester. Illustrative of the techniques suitable for this purpose are solid state Nuclear Magnetic Resonance (NMR), X-ray powder diffraction, X-ray crystallography, Differential Scanning calorimetry (DSC), dynamic vapor sorption/desorption (DVS), Karl Fischer analysis (KF), hot stage microscopy, modulated differential screening calorimetry, FT-IR, and Raman spectroscopy.

In particular, analysis of the XRPD and DSC data can distinguish Form A, Form B, and hemibenzenate forms of CDDO-methyl ester.

The properties of the inventive CDDO methyl ester forms are both distinctive, as mentioned above, and conducive to their use as medicinal agents. For example, the bioavailability of Form B and Form A CDDO methyl ester varied in monkeys when the monkeys received equivalent dosages of the two forms orally, in gelatin capsules. See Example 7. In addition, the stability of the newly identified CDDO-methyl ester forms will be useful in the production of pharmaceutical compositions.

In similar manner to distinguishing Form A and Form B CDDO methyl ester from each other and from other forms of CDDO methyl ester, CDDO methyl ester dispersions that retain "x-ray amorphous" character, as described in greater detail below, can be distinguished from dispersions containing crystalline Form A CDDO methyl ester by a variety of techniques, including XRPD and DSC analysis. Thus, dispersions containing Form A crystalline CDDO methyl ester typically display discrete peaks characteristic of the pure Form A CDDO methyl ester, particularly those that occur at approximately 13.35 and 8.78 (°2θ) (for example, see Table 17, infra).

The properties of a CDDO methyl ester polymer excipient dispersion of the invention are both distinctive and conducive to their use as medical agents. For example, the bioavailability of selected CDDO methyl ester dispersions, formulated with additional inactive additives, varied in monkeys when the monkeys received equivalent dosages of the dispersions in gelatin capsules. See Example 7, infra, study phases 2 and 3. In several instances, formulations containing CDDO methyl polymer excipient dispersions produced surprising further enhancements in bioavailability, even relative to formulations produced from pure Form B CDDO methyl ester.

The presence of multiple forms, including polymorphs, in pharmaceutical solids has been previously described, for instance, by Cui (2007). The crystalline and amorphous forms of a compound may exhibit different physical and chemical characteristics. For instance, amorphous forms may have higher solubility relative to the crystalline form. Every compound is unique in this regard, however, and the degree to which an amorphous material will differ from the crystalline state must be investigated on a case-by-case basis and cannot be predicted a priori. In addition, some amorphous materials are prone to re-crystallization.

In the present context, variability in data collection can arise due to a myriad of factors. Accordingly, this description uses the terms "about" or "approximately" to indicate variations in data used to describe the CDDO-methyl ester forms. For example, a melting temperature may vary based on instrumentation or conditions. Regarding the precision of the measurement, the USP <891> states that "In the case of melting, both an "onset" and a "peak" temperature can be determined objectively and reproducibly, often to within a few tenths of a degree." Practical experience indicates this is not true for measuring the $T_g$ of a material. The $T_g$ will depend on many factors: how the sample was prepared, the thermal history of the sample (relaxation), residual solvent that may or may not volatilize prior to $T_g$, the instrument, sample preparation (sample mass, particle size, packing, diluents), the parameters used to measure $T_g$ (particularly scan rate), the parameters used to determine the location of the $T_g$ (onset temperature, mid-point temperature, inflection point temperature, or offset temperature), whether a relaxation endotherm is present at $T_g$, and other factors. Some factors will decrease $T_g$ (plasticization due to residual water/solvent), while others will increase $T_g$ (faster scan rate, relaxation) and may do so by as much as 10-15° C. The change in heat capacity at $T_g$ ($\Delta$Cp) can be important, as reported by Zhou et al., *J. Pharmaceutical Sciences* 91: 1863-72 (2002).

The present description speaks of different patterns in terms of their "characteristic" peaks. The assemblage or group of such peaks is unique to a given polymorphic form, within the uncertainty attributable to individual instruments and to experimental conditions, respectively.

For each of the crystalline forms, a group of five characteristic peaks is listed in Tables 17-19, below. Typical variation can be ±0.1°2θ, but peak position can vary up to ±0.2°2θ or more in some experiments.

TABLE 17

| Form A
Peak Position (°2θ) |
| --- |
| 13.35 |
| 8.78 |
| 17.4 |
| 12.94 |
| 14.18 |

TABLE 18

| Dimethanolate
Peak Position (°2θ) |
| --- |
| 8.87 |
| 11.26 |
| 16.63 |
| 16.9 |
| 13.72 |

TABLE 19

| Hemibenzenate
Peak Position (°2θ) |
| --- |
| 14.17 |
| 9.25 |
| 16.32 |
| 14.62 |
| 17.11 |

The XRPD pattern of the glassy material (Form B) shows a broad halo peak at approximately 13.5°2θ, which appears to be characteristic of Form B. Other halos are not as well-defined, and the shape/position of this pattern may change as a function of the instrument and experimental conditions. Variation in the position of this broad peak will be larger than that of the characteristic peaks of the respectively crystalline forms. In particular, variability of up to ±1°2θ for the broad peak of Form B can be expected in certain instruments.

The XRPD pattern of glassy materials produced as CDDO methyl ester excipient dispersions also show a broad halo peak, typically centered at approximately 13.5°2θ. These materials likewise display a $T_g$ by modulated Differential Scanning calorimetry (mDSC). Similar to pure Form B CDDO methyl ester samples, the shape and position of the XRPD pattern for an excipient dispersion may change as a function of the instrument used, the experimental conditions, and the specific excipient employed to produce the dispersions.

The present invention further relates to the use of Form A, Form B, and glassy, XRPD-amorphous excipient dispersions of CDDO methyl ester, respectively, for treating diseases associated with inflammation, including a cancerous condition and various pathologies affecting the central nervous system. Pursuant to the invention, treatment of these diseases comprises administering to a subject in need thereof an effective amount of the novel CDDO methyl ester forms enumerated here. These compounds have utility for ameliorating or preventing inflammation involved in the etiology of cancer, Alzheimer's disease (AD), Parkinson's disease (PD), multiple sclerosis (MS), amyotrophic lateral sclerosis (ALS), rheumatoid arthritis (RA) and other autoimmune diseases, inflammatory bowel disease, and other pathological conditions tied to excessive production of either nitric oxide or prostaglandins.

As previously noted, the aberrant or excessive expression of either cyclooxygenase-2 (COX-2) or inducible nitric oxide synthase (iNOS) has been implicated in the pathogenesis of many disease processes, including carcinogenesis in the colon. Several synthetic analogs of triterpenoids, including CDDO methyl ester, have been reported to suppress iNOS expression. Related studies have shown triterpenoid suppression of both iNOS and COX-2 expression in macrophages that have been stimulated by IFN-γ or LPS (Suh et al., 1998; Honda et al., 2002). Therefore, treatments administering CDDO methyl ester forms are expected to affect iNOS and COX-2 suppression.

Overexpression of the gene for COX-2 is an early and central event in colon carcinogenesis (Prescott and White, 1996; Dubois et al., 1996). Mice with defects in the APC (adenomatous polyposis coli) gene develop large numbers of intestinal polyps at an early age, and marked elevations in COX-2 enzyme levels have been found in these polyps. These animal findings correlate with the finding of elevated levels of COX-2 mRNA and protein in many human primary colon cancers and colon cancer cell lines (Prescott and White, 1996), and it is believed that this elevation in COX-2 leads to a suppression of apoptosis, which would ordinarily lead to death of pre-neoplastic cells (Tsujii and DuBois, 1996). The functional relevance of COX-2 to intestinal tumorigenesis has been demonstrated by knockout of the COX-2 gene (Oshima et al., 1996). Mice bearing this knockout were mated with polyp-forming mice bearing lesions in the APC gene; the COX-2 knockout caused a dramatic diminution in the number of polyps in the offspring. Furthermore, treatment of experimental animals with either selective COX-2 inhibitors or non-selective COX-1/COX-2 inhibitors has been reported to be a potent approach to chemoprevention of intestinal cancer (Marnett, 1992; Oshima et al., 1996; Boolbol et al., 1996; Reddy et al., 1996; Sheng et al., 1997). As for the role of iNOS in carcinogenesis, it is clear that NO is a potent mutagen (Tamir and Tannebaum, 1996), and that nitric oxide can also activate COX-2 (Salvemini et al., 1993, 1994). There also is a marked increase in iNOS in rat colon tumors induced by the carcinogen, azoxymethane (Takahashi et al., 1997). Similarly, overexpression of iNOS in human tumors has been reported as a negative prognostic factor (e.g., Ekemekcioglu et al., 2006).

Inflammatory signaling pathways and other disease-associated signaling pathways, such as are induced by angiotensin II, frequently stimulate excessive production of reactive oxygen or nitrogen species (RONS), including superoxide, hydrogen peroxide, nitric oxide and peroxynitrite. CDDO methyl ester has been shown to be a potent inducer of antioxidant activity and a potent inhibitor of inflammatory processes in many different cell types (Dinkova-Kostova et al., 2005; Liby et al., 2006; Ahmad et al., 2006; Shishodia et al., 2006). Severe, acute inflammation due to a variety of causes including infection, trauma, burns, and chemical exposure can be life threatening and may cause liver failure, kidney failure, respiratory failure, or heart failure. Chronic inflammation and the associated oxidative stress contribute to the pathology of many important diseases including autoimmune diseases (e.g., rheumatoid arthritis, lupus, psoriasis, and multiple sclerosis), cardiovascular diseases (e.g., atherosclerosis and heart failure), diabetes (type I and type II), respiratory diseases (e.g., chronic obstructive pulmonary disease and asthma), chronic kidney disease, renal failure, liver failure, and pain syndromes (e.g., neuropathic pain, fibromyalgia, and migraine). In addition, triterpenoids have been shown to inhibit the replication of HIV-1 in macrophages (Vazquez et al., 2005) and so may be useful in the treatment of viral diseases, particularly those in which significant morbidity is caused by organ or tissue inflammation (e.g., viral hepatitis, influenza, herpes simplex).

MS is known to be an inflammatory condition of the central nervous system (Williams, Ulvestad and Hickey, 1994; Merrill and Beneviste, 1996; Genain and Nauser, 1997). Inflammatory, oxidative, or immune mechanisms may be involved in the pathogenesis of MS, AD, PD, and ALS (Bagasra et al., 1995; Griffin et al., 1995; McGeer and McGeer, 1995; Good et al., 1996; Simonian and Coyle, 1996; Kaltschmidt et al., 1997). Both reactive astrocytes and activated microglia have been implicated in causation of NDD/NID; there has been a particular emphasis on microglia as cells that synthesize both NO and prostaglandins as products of the respective enzymes, iNOS and COX-2. De novo formation of these enzymes may be driven by inflammatory cytokines such as interferon-gamma or interleukin-1 In turn, excessive production of NO may lead to inflammatory cascades and/or oxidative damage in cells and tissues of many organs, including neurons and oligodendrocytes of the nervous system, with consequent manifestations in AD and MS, and possibly PD and ALS (Coyle and Puttfarcken, 1993; Goodwin et al., 1995; Beal, 1996; Good et al., 1996; Merrill and Benvenist, 1996; Simonian and Coyle, 1996; Vodovotz et al., 1996). Epidemiologic data indicate that chronic use of NSAID's, which block synthesis of prostaglandins from arachidonate, markedly lowers the risk for development of AD (McGeer et al., 1996; Stewart et al., 1997). Accordingly, Form A and Form B of CDDO methyl ester, as agents that block formation of NO and prostaglandins, should be useful in therapeutic approaches to treating or preventing NDD.

As described above, in a variety of preclinical studies CDDO-Me has demonstrated an ability to inhibit the expression of COX-2 and iNOS, enzymes associated with both inflammation and carcinogenesis. CDDO-Me also was shown to inhibit the activation of nuclear factor-kappa B (NF-κB) and Signal Transducer and Activator of Transcription 3 (STAT3), transcription factors associated with inflammation, tumor progression, and tumor resistance to therapy. Initial studies evidenced that CDDO-Me inhibited the growth of many cancer cell lines; the average $IC_{50}$ value for CDDO-Me in the NCI-60 tumor cell line panel was approximately 35 nM. In vivo studies confirmed that CDDO-Me effectively inhibited the growth of tumors formed by human tumor cell lines implanted in rodents or syngeneic cancer cell lines implanted in rodents (Table 16). Doses used in these studies were generally in the range of 10 to 100 mg/kg/day, depending on the species, strain, and method of administration.

Studies detailed below provide human data that reflect the beneficial effect of CDDO-methyl ester on patients suffering from a cancerous condition. See Example 10.

In light of the foregoing, the present invention encompasses stable, controlled release dosage forms containing a CDDO methyl ester form. A dosage form of the invention can be for once-per-day administration, for delayed release, or for pulsatile release, thereby to optimize therapy by matching pharmacokinetic performance with pharmacodynamic requirements.

Any of Form B, Form A, and formulations containing excipient dispersions of CDDO methyl ester may be administered orally. The active compound may be coated in a material to protect the compound from the action of acids and other natural conditions which may inactivate the compound. Other modes of administration, such as topical, subcutaneous, intravenous, and intraperitoneal are also part of the current invention.

To administer the therapeutic compound, it may be necessary to coat the compound with or to co-administer the compound with a material to prevent its inactivation. Thus, either Form B or Form A CDDO methyl ester may be administered to a subject in an appropriate carrier, such as liposomes, or in a diluent. Pharmaceutically acceptable diluents include saline and aqueous buffer solutions. Liposomes include water-in-oil-in-water CGF emulsions as well as conventional liposomes. See, e.g., Strejan et al., *J. Neuroimmunol.* 7: 27(1984).

The therapeutic compound can be administered orally, with inert diluents, additives, or an edible carrier, to form a pharmaceutical composition. To this end, the therapeutic compound of the invention, with other ingredients, may be enclosed in a hard or soft shell gelatin capsule, compressed into tablets, or incorporated directly into the subject's diet. For oral therapeutic administration, Form A or Form B may be incorporated with excipients and used in the form of ingestible tablets, buccal tablets, troches, capsules, elixirs, suspensions, syrups, wafers, and the like. Similarly, an excipient dispersion of the present invention may be presented in a variety of dosage form types, including those described here for Form A or Form B. The percentage of the therapeutic compound in the compositions and preparations may be varied, in accordance with conventional practice, to effect a suitable dosage of the active agent.

Additionally, the present invention relates to a pharmaceutical composition comprising an effective amount of Form B CDDO methyl ester or Form A, in association with one or more non-toxic, pharmaceutically acceptable carriers and/or diluents and, if desired, other active ingredients. As noted above, the active compound can be produced as a homogeneous excipient dispersion, starting from either Form B or Form A. Such a CDDO methyl ester excipient dispersion is a solid solution and can be viewed as a homogeneous dispersion at the molecular level. Such dispersions can be advantageously formulated together with other pharmaceutically acceptable additives, to stabilize the active compound and, in some instances, to provide further improvements in bioavailability.

In formulating CDDO methyl ester as an excipient dispersion, the choice of an excipient for the dispersion is guided by the criteria that the excipient be both a good "glass former" and pharmaceutically acceptable. More generally, the excipient should form a stable, homogeneous glassy matrix, which stabilizes the dispersion by affording a $T_g$ that is above typical, ambient temperature storage conditions. An additional criterion in this regard is that the excipient used for the dispersion should be chemically compatible with other additives, such as binders, fillers, lubricants, glidants, and the like, which may be employed in the final formulation to confer desired functional properties.

In satisfaction of these criteria, an excipient can be selected, pursuant to the invention, from a number of compounds characterized by suitably high $T_g$ values, such as (A) carbohydrates, carbohydrate derivatives, and carbohydrate polymers, (B) synthetic organic polymers, (C) organic acid salts, (D) proteins, polypeptides, and peptides, and (E) high molecular weight polysaccharides such as heparin, which is a sulfated polysaccharide, and hyaluronic acid, a mucopolysaccharide.

Illustrative of class (A) are: cellulose derivatives, such as hydroxypropyl cellulose (HPC), hydroxypropyl methyl cellulose (HPMC), and ethyl cellulose; polysaccharides, such as raffinose, maltotriose, stachyose, dextrins (including maltodextrins and cyclodextrins, inter alia), dextrans, and soluble starch; alditols, such as mannitol, xylitol, and sorbitol; and disaccharides, such as lactose, trehalose, maltose, and sucrose. A preferred excipient from this class is hydroxypropyl methyl cellulose phthalic ester (HPMC-P).

Class (B) is exemplified by poly[1-(2-oxo-1-pyrrolidinyl) ethylene, a/k/a povidone or polyvinylpyrrolidone (PVP) and related co-polymers, such as PVP/VA, of varying molecular weights. Also included in this class is the methacrylic acid family of copolymers, such as methacrylic acid copolymer Type C (USP/NF).

Class (C) is illustrated by salts, such as sodium, potassium, calcium and magnesium salts, of lactic acid, ascorbic acid, maleic acid, oxalic acid, malonic acid, malic acid, succinic acid, citric acid, gluconic acid, and glutamic acid, respectively. Thus, representative salts in this regard are sodium citrate, sodium lactate, sodium maleate, magnesium gluconate, and sodium ascorbate.

Exemplary class (D) excipients are: human serum albumin; a polyamino acid, e.g., polyalanine, polyarginine, polyglycine, and polyglutamic acid; casein; collagen; gelatin and purified gelatin proteins; and certain pharmacologically active compounds, such as insulin.

Excipients can alter some of the physical characteristics of the pharmaceutical formulations, as noted. For instance, dispersion within the various polymeric excipients may lead to a reduction in the observed $T_g$ of the formulation. Normally, $T_g$ is an additive property based on proportions of materials involved. Accordingly, when utilizing polymers with $T_g$ values that are less than that of the amorphous Form B, there is an expectation of a reduction in observed $T_g$ for the dispersions (mixtures). Additionally, moisture or traces of residual organic solvent often are present, which tends to reduce $T_g$ as well. For purposes of generating a solid CDDO-Me dispersion, the optimal choice of excipient typically must be determined empirically. For example, attempts to produce glassy, XRPD-amorphous dispersions using the polyethylene glycol (PEG) family of excipients, such as PEG 6000, produced mixtures containing characteristic peaks associated with the presence of Form A CDDO methyl ester. Similar results were obtained using Vitamin E—TPGS, an excipient produced by esterifying d-alpha-tocopheryl acid succinate with polyethylene glycol 1000, as well as using ethylene oxide—propylene oxide copolymers such as Pluronic®. As the examples below illustrate, certain polymeric excipients used to form dispersions with CDDO-Me, pursuant to the invention, display surprising improvements in oral bioavailability relative to the pure Form B drug substance.

Methods can vary for preparing homogenous, glassy, X-ray amorphous dispersions of CDDO-Me with pharmaceutically acceptable excipients, and the examples presented here utilize spray drying to generate such dispersions. Other methods of manufacture may be used to produce dispersions of the invention with equivalent properties and utility. See Repka et al., 2002, and references cited therein. Such other methods include but are not limited to solvent evaporation and extrusion, such as hot melt extrusion.

In addition to an excipient, other additives may be included to aid in stability of the active ingredient, to adjust the pH (i.e., a buffering agent), to improve dispersibility, to aid in providing uniformity of delivery, and to achieve other characteristics desired for a pharmaceutical formulation.

The administered quantity of the compound or composition of the present invention will vary, depending on the patient and the mode of administration, and can be any effective amount.

A given treatment regimen for the administration of a composition of the present invention can be developed by way of normal and routine pre-clinical and clinical testing, the details of which are a function of the therapeutic indication, among other factors. The quantity of the active agent administered may vary over a wide range, thereby to provide, in a unit dosage, a pharmacologically effective amount based upon the body weight of the patient per day, to achieve the desired effect. The desired dosage may also vary according to the condition being treated. For example, treatment of acute cancer may require a significantly higher dose than treatment of an inflammatory condition such as arthritis.

In particular, a composition of the present invention is presented as a unit dose and taken preferably from 1 to 3 times daily, most preferably once daily to achieve the desired effect.

In addition, a composition of the current invention may be taken every two days, every three days, every four days, every five days, every six days, or once a week.

The compositions of the current invention also may be administered alone or in combination with other drugs based on the particular needs of a patient. In particular, the compositions of the current invention may be administered with anti-cancer agents as part of a treatment regimen. For example, CDDO-methyl ester may be administered with gemcitabine, or other agents, during the treatment of a cancer, such as pancreatic cancer.

In general, pharmaceutical compositions of the invention are prepared using conventional materials and techniques, such as mixing, blending and the like. Moreover, a medicament containing Form A or Form B also can contain other components, including but not limited to suitable adjuvants, carriers, excipients, and stabilizers, etc. A therapeutic formulation of the invention is preferably a solid but, in principle, could be a liquid, such as a suspension or emulsion.

Pursuant to the invention, the oral maintenance dose typically is between about 0.1 mg and about 1000 mg, preferably given once daily. The dosage may be varied or keyed to a subjects weight. Typical dosages may be from about 0.01 mg/kg to 100 mg/kg, with the preferred unit dosage forms including tablets and capsules.

The following examples are illustrative only and are not intended to limit the present invention. The materials and methods employed in the examples are outlined below:

a. Materials

Solvents and other reagents were purchased from commercial suppliers and were either HPLC or ACS grade.

b. Experimental Methods i. Approximate Solubility—Solvent Addition Method

A weighed sample was treated with aliquots of the test solvent at room temperature. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than."

ii. Polymorph Screen

Both thermodynamic and kinetic crystallization techniques were employed. These techniques are described in more detail below. Once solid samples were harvested from crystallization attempts, they were either examined under a microscope for morphology or observed with the naked eye. Any crystalline shape was noted, but sometimes the solid exhibited unknown morphology, due to small particle size. Solid samples were then analyzed by XRPD, and the patterns were compared to each other to identify new crystalline or non-crystalline forms.

(i) Cold Precipitation (CP)

Solutions were prepared in various solvents at elevated temperature. The solutions were then filtered through a 0.2-µm nylon or PTFE filter into an antisolvent at sub-room temperature. The presence or absence of solids was noted. If there were no solids present, or if the amount of solids was judged too small for XRPD analysis, the vial was placed in a freezer. The resulting solids were isolated by filtration and dried prior to analysis.

(ii) Fast Evaporation (FE)

Solutions were prepared in various solvents and sonicated between aliquot additions to assist in dissolution. Once a mixture reached complete dissolution, as judged by visual observation, the solution was filtered through a 0.2-µm nylon filter. The filtered solution was allowed to evaporate at room temperature in an uncapped vial. The solids that formed were isolated and analyzed.

(iii) Freeze Dry (FD)

1,4-dioxane solutions were prepared, filtered through a 0.2-µm nylon filter, and frozen using dry ice. The frozen sample was lyophilized using an FTSsystems Flexi-Dry. The lyophilization temperature was not controlled.

(iv) Micronization

Micronization of materials can be accomplished in fluid energy mills and can reduce particle size to 1 to 20 microns. Further description of these processes can be found in PERRY'S CHEMICAL ENGINEERS' HANDBOOK, $7^{th}$ ed. (McGraw Hill, 1998).

(v) Grinding

A solid sample was placed into a stainless steel milling rotor with a small metal ball. Some samples had a small amount of water added (wet grinding). The sample was then ground at 30 Hz on a Retesh type MM220 mixermill for approximately 20 minutes. The resulting solids were isolated and analyzed.

(vi) Cryo grinding

A solid sample was placed into a stainless steel grinding jar with a grinding rod. The sample was then ground at 15 Hz on a SPEX Certiprep model 6750 cryomill for a set amount of time. The grinding jar was submerged in a bath of liquid nitrogen during the experiment. The solids were isolated and analyzed.

(vii) Melt/Quench

A solid sample was placed on a glass microscope slide and leveled. The slide was then placed on a hot plate at a set temperature until the solid melted. Upon melting, the slide was removed from the hot plate and placed on a cold counter top to cool quickly. The resulting solids were dried under nitrogen and analyzed.

(viii) Rotary Evaporation

Solutions were prepared in various solvents and filtered through a 0.2-μm nylon filter. The sample was placed on the rotary evaporator and removed when dry. The resulting solids were isolated and analyzed.

(ix) Slow Evaporation (SE)

Solutions were prepared in various solvents and sonicated between aliquot additions to assist in dissolution. Once a mixture reached complete dissolution, as judged by visual observation, the solution was filtered through a 0.2-μm nylon filter. The filtered solution was allowed to evaporate at room temperature or under nitrogen in a vial covered with aluminum foil perforated with pinholes. The solids thus formed were isolated and analyzed.

(x) Slow Cool (SC)

Saturated solutions were prepared in various solvents at approximately 60° C. and filtered through a 0.2-μm nylon filter into an open vial while still warm. The vial was covered and allowed to cool slowly to room temperature. The presence or absence of solids was noted. If there were no solids present, or if the amount of solids was judged too small for XRPD analysis, the vial was placed in a refrigerator. Again, the presence or absence of solids was noted and, if there were none, the vial was placed in a freezer. Solids that formed were isolated by filtration and allowed to dry prior to analysis.

(xi) Slurry Experiments

Solutions were prepared by adding enough solids to a given solvent so that excess solids were present. The mixture was then agitated in a sealed vial at room temperature. After either 7 or 10 days, the solids were isolated by vacuum filtration and analyzed.

(xii) Stress Experiments

Solids were stressed under different temperature and/or relative humidity (RH) environments for a measured time period. Specific RH values were achieved by placing the samples inside sealed chambers containing saturated salt solutions or inside ESPEC temperature and humidity cabinets. The salt solutions were selected and prepared following an ASTM standard procedure. Samples were analyzed by XRPD immediately after removal from the stress environment.

iii. Single Crystal Structure Determination (i) Sample Preparation

A saturated solution of CDDO methyl ester was prepared in methanol at ~60° C. and filtered through a 0.2-μm filter into an open vial while still warm. The vial was covered and allowed to cool slowly to room temperature. The presence of pyramidal tablets was observed after 1 day.

(ii) Data Collection

A colorless plate of CDDO-Me ($C_{32}H_{43}NO_4$) having approximate dimensions on two sides of 0.01×0.01 mm, was mounted on a glass fiber in random orientation. Preliminary examination and data collection were performed with Mo $K_\alpha$ radiation (λ=0.71073 Å) on a Nonius KappaCCD diffractometer equipped with a graphite crystal, incident beam monochromator. Refinements were performed on a LINUX PC using SHELX97 (Sheldrick, 1997) [1].

Cell constants and an orientation matrix for data collection were obtained from least-squares refinement using the setting angles of 46742 reflections in the range 2°<θ<22°. The refined mosaicity from DENZO/SCALEPACK [2] was 0.32° indicating good crystal quality. The space group was determined by the program XPREP [3]. From the systematic presence of the following conditions: h00 h=2n, 00l l=4n, and from subsequent least-squares refinement, the space group was determined to be $P4_32_12$ (no. 96).

The data were collected to a maximum 2θ value of 44.43°, at a temperature of 150±1 K.

(iii) Data Reduction

Frames were integrated with DENZO-SMN [2]. A total of 46742 reflections were collected, of which 9168 were unique. Lorentz and polarization corrections were applied to the data. The linear absorption coefficient is 0.074 mm$^{-1}$ for Mo $K_\alpha$ radiation. An empirical absorption correction using SCALEPACK [2] was applied. Transmission coefficients ranged from 0.9995 to 0.9999. Intensities of equivalent reflections were averaged. The agreement factor for the averaging was 9.3% based on intensity.

(iv) Structure Solution and Refinement

The structure was solved by direct methods using SHELXS97 [1]. The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2 - |F_c|^2)^2$$

The weight w is defined as $1/[\sigma^2(F_o^2)+(0.0176P)^2+(0.0000P)]$, where $P=(F_o^2+2F^2)/3$.

Scattering factors were taken from the "International Tables for Crystallography" [5]. Of the 9168 reflections used in the refinements, only the reflections with $F_o^2 > 2\sigma(F_o^2)$ were used in calculating R. A total of 5421 reflections were used in the calculation. The final cycle of refinement included 1024 variable parameters and converged (largest parameter shift was <0.01 times its estimated standard deviation) with unweighted and weighted agreement factors of:

$$R = \Sigma |F_o - F_c| / \Sigma F_o = 0.051$$

$$R_w = \sqrt{(\Sigma w(F_o^2 - F_c^2)^2 / \Sigma w(F_o^2)^2)} = 0.085$$

The standard deviation of an observation of unit weight was 1.05. The highest peak in the final difference Fourier had a height of 0.22 e/Å3. The minimum negative peak had a height of −0.25 e/Å$^3$.

(v) Calculated X-ray Powder Diffraction (XRPD) Pattern

A calculated XRPD pattern was generated for Cu radiation using PowderCell 2.3 [6] and the atomic coordinates, space group, and unit cell parameters from the single crystal data.

(vi) ORTEP and Packing Diagrams

The ORTEP diagram was prepared using ORTEP III [7] [9]. Atoms are represented by 50% probability anisotropic thermal ellipsoids. Packing diagrams were prepared using CAMERON [8] modeling software. Additional figures and BFDH morphology predictions were generated using Mercury 1.4.1 [4].

c. Instrumental Techniques i. Differential Scanning Calorimetry (DSC)

Analyses were carried out on a TA Instruments differential scanning calorimeter 2920 or Q1000. The instrument was calibrated using indium as the reference material. The sample was placed into a standard aluminum DSC pan with a crimped lid configuration, and the weight accurately recorded. The sample cell was equilibrated at 25° C. and heated under a nitrogen purge at a rate of 10° C./min, up to a final temperature of 250° C.

ii. Dynamic Vapor Sorption/Desorption (DVS)

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.010% weight change in 5 minutes, with a maximum equilibration time of 3 hours if the weight criterion was not met. Data were not corrected for the initial moisture content of the samples. Sodium chloride and polyvinypyrrolidine were used as calibration standards.

iii. Karl Fischer (KF)

Coulometric Karl Fischer (KF) analysis for water determination was performed using a Mettler Toledo DL39 Karl Fischer titrator. Approximately 24-32 mg of sample was placed in the KF titration vessel containing Hydranal—Coulomat AD. The sample was then titrated by means of a generator electrode which produces iodine by electrochemical oxidation:

$2 I-=>I_2+2e$. Three replicates were obtained to ensure reproducibility.

iv. Hot Stage Microscopy

Hot stage microscopy was performed using a Linkam hot stage (model FTIR 600) mounted on a Leica DM LP microscope. Samples were observed using a 20× objective (obj.) with cross polarizers (CP) and lambda ($\lambda$) compensator. Samples were placed on a coverslip. A second coverslip was then placed over the sample. Each sample was visually observed as the stage was heated. Images were captured using a SPOT Insight™ color digital camera with SPOT Software v. 4.5.9. The hot stage was calibrated using USP melting point standards.

v. Modulated Differential Scanning calorimetry (MDSC)

Modulated differential scanning calorimetry data were obtained on a TA Instruments differential scanning calorimeter equipped with a refrigerated cooling system (RCS). The sample was placed into an aluminum DSC pan, and the weight accurately recorded. The pan was covered with a lid and crimped. MDSC data were obtained using a modulation amplitude of +/−0.8° C. and a 60 second period with an underlying heating rate of 2° C./min from −25 to 250° C. The temperature and the heat capacity were calibrated using indium metal and sapphire as the calibration standards, respectively. The reported glass transition temperature is obtained from the inflection of the step change in the reversible heat flow versus temperature curve.

vi. Nuclear Magnetic Resonance (NMR)

The solution phase $^1$H NMR spectra were collected by Spectra Data Services, Inc. Acquisition parameters are printed on each spectrum. Spectra were referenced to internal tetramethylsilane at 0.0 ppm.

vii. Optical Microscopy

Observations made by optical microscopy were collected on a Wolfe polarizing optical microscope at a magnification of 4x. Crossed polarizers (CP) were used to observe birefringence in the samples.

viii. Scanning Electron Microscopy (SEM)

Scanning electron microscopy (SEM) was performed using a FEI Quanta 200 scanning electron microscope. Under high vacuum mode, a solid state backscatter (Etd) detector was used. Beam voltage was 5.0 kV. Samples were sputter coated using a Cressington 108auto Sputter Coater at ~20 mA and ~0.13 mbar (Ar) with Au/Pd for 75 seconds. Samples were prepared for analysis by placing a small amount on carbon double-stick tape fixed to an aluminum sample mount. The instrument was calibrated for magnification using NIST standards. Data was collected using xTm (v. 2.01), build number 1564 and analyzed using XT Docu (v. 3.2). Magnifications reported on the SEM images were calculated upon the initial data acquisition. The scale bar reported in the lower portion of each image is accurate upon resizing the images and should be utilized when making size determinations.

ix. Thermogravimetry (TG)

Analyses were carried out on a TA Instruments 2950 thermogravimetric analyzer. The calibration standards were nickel and Alumel™. Each sample was placed in an aluminum sample pan and inserted into the TG furnace. Samples were first equilibrated at 25° C., then heated under a stream of nitrogen at a heating rate of 10° C./min, up to a final temperature of 350° C. unless specified otherwise.

x. X-Ray Powder Diffraction (XRPD)

(i) Inel XRG-3000

X-ray powder diffraction analyses were also performed on an Inel XRG-3000 diffractometer, equipped with a curved position-sensitive detector with a 2θ range of 120°. Real time data was collected using Cu Kα radiation at a resolution of 0.03°2θ. The tube voltage and amperage were set to 40 kV and 30 mA, respectively. Patterns are displayed from 2.5 to 40°2θ to facilitate direct pattern comparisons. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard.

d. Additional Calculation Techniques i. PDF

One technique used in the computational analysis of x-ray amorphous data is the Pair Distribution Function (PDF). As the name suggests, the PDF is made up from a linear sum of all the coherent atom-atom interactions within the material. Defective (disordered) materials will exhibit the same atom-atom interactions as the crystalline phase, but over a reduced length scale. Therefore, such materials can be compared to parent crystalline materials by examining the peaks in the PDF over the first few nanometers. Comparisons between spectra in the range of 0 Å to about 5 Å are difficult due to artifacts in this region.

On the formation of glassy material, the PDF peaks will exhibit some movement from the crystalline peak positions as the molecules relax their positions. This is similar to a thermal expansion/contraction event where, although the PDF peaks move slightly, the relative peak intensities should still be recognizable as being related to the original crystalline material. As the material enters the thermodynamic amorphous state, some of the point group symmetry relationships will be lost giving a PDF of reduced complexity. There also will be some peak movement. The glassy/amorphous materials will exhibit PDFs that will rapidly fall to zero over 2 to 3 nearest neighbor (NN) distances.

Measurement conditions are used to minimize the background in the x-ray patterns and algorithms are used to calculate the PDF from measured x-ray data. The PDFs were calculated using PatternMatch v2.2.1, using the entire range of measured data for all samples.

EXAMPLE 1

Solubility Estimates

Approximate solubilities were determined in various solvents at room temperature, with the results as provided in Table 2. CDDO methyl ester exhibits high solubility in the majority of the organic solvents used. The solubility in water appears to be less than 0.1 mg/mL.

EXAMPLE 2

Polymorph Screen Results

Approximately 50 polymorph screen experiments were performed. Form A was observed from approximately 50% of the samples. The formation of Form A was not limited to a particular crystallization condition and was prepared from a variety of different experiments and solvents. Form B material was prepared from lyophilization, melt/quench, and several evaporation experiments.

Polymorph screen samples are listed alphabetically in Tables 3-5 by the solvent used. Representative XRPD patterns of Form A and Form B materials are compared in FIG. 2. Characterization data of the forms are summarized in the examples below.

EXAMPLE 3

Characterization of CDDO-methyl Ester—Form A (Unmicronized)

Form A is unsolvated (Table 6). The single crystal structure of Form A was determined based on methods described above. Crystals of CDDO-methyl ester were grown and submitted for single crystal structure analysis. The crystal structure was determined by single crystal X-ray diffraction. The proposed structure of CDDO-methyl ester is shown in FIG. 1.

The tetragonal cell parameters and calculated volume are: a=14.21620(10) Å, b=14.21620(10) Å, c=81.5875(12) Å, α=90.00°, β=90.00°, γ=90.00°, V=16488.9(3) Å$^3$. The molecular weight of CDDO methyl ester is 505.70 g/mol with Z=24 resulting in a calculated density of 1.222 g cm$^{-3}$. The space group was determined to be P4$_3$2$_1$2 (no. 96). A summary of the crystal data and crystallographic data collection parameters is provided in Table 10.

The quality of the structure obtained is high, as indicated by the R-value of 0.051 (5.1%). Usually R-values in the range of 0.02 to 0.06 are quoted for the most reliably determined structures.

Figure 13:
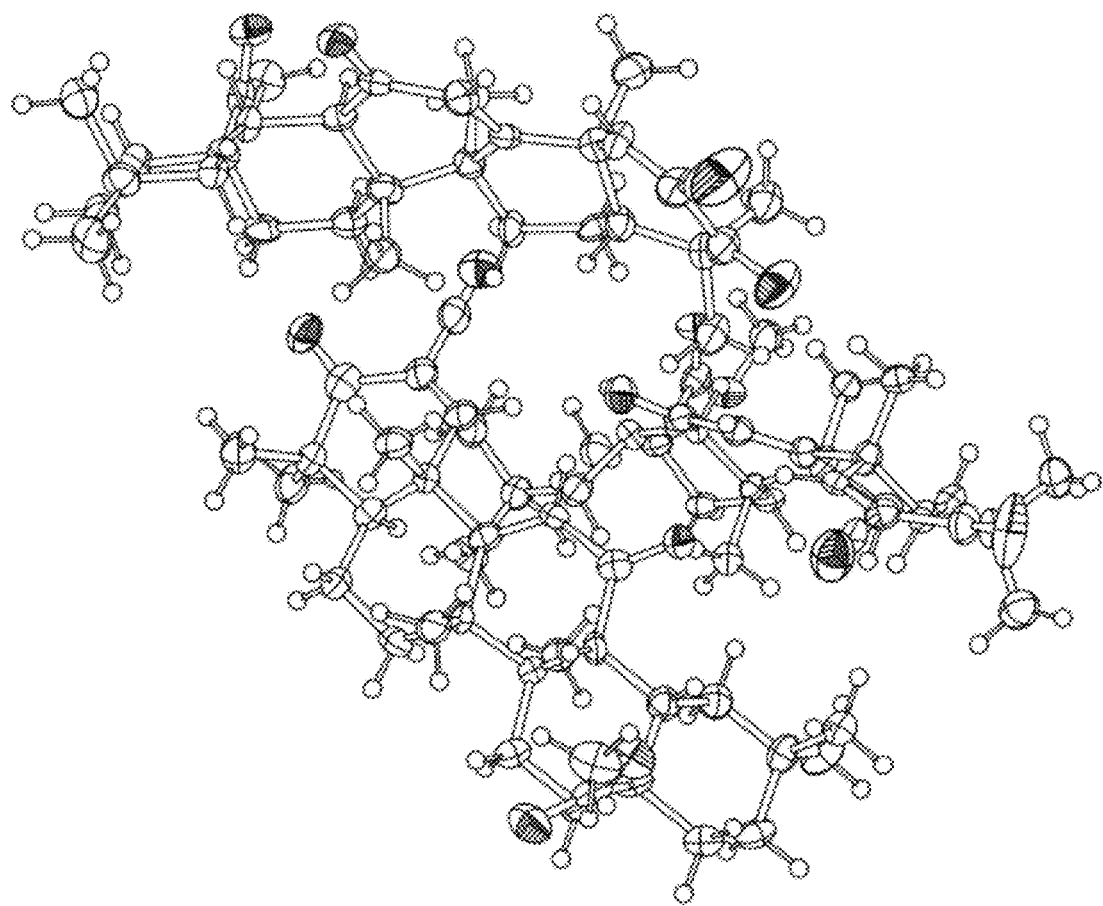
FIG. 13 shows an ORTEP drawing of the contents of the asymmetric unit of Form A crystals. Atoms are represented by 50% probability anisotropic thermal ellipsoids.

An ORTEP drawing of a single CDDO methyl ester molecule is shown in FIG. 12. The asymmetric unit shown in FIG. 13 contains three CDDO methyl ester molecules. The molecules are the same as the proposed structure from FIG. 1.

Packing diagrams viewed along the a, b, and c crystallographic axes are shown in FIGS. 14-16, respectively. With no hydrogen bonds, the crystal structure includes numerous van der Waals interactions. The view down the crystallographic b axis (FIG. 15) highlights the helical nature of the packing arrangement of the tetragonal screw axis and the predicted BFDH morphology. The predicted morphology is in good agreement with the observed habit of the single crystal used in the data collection.

Figure 17:
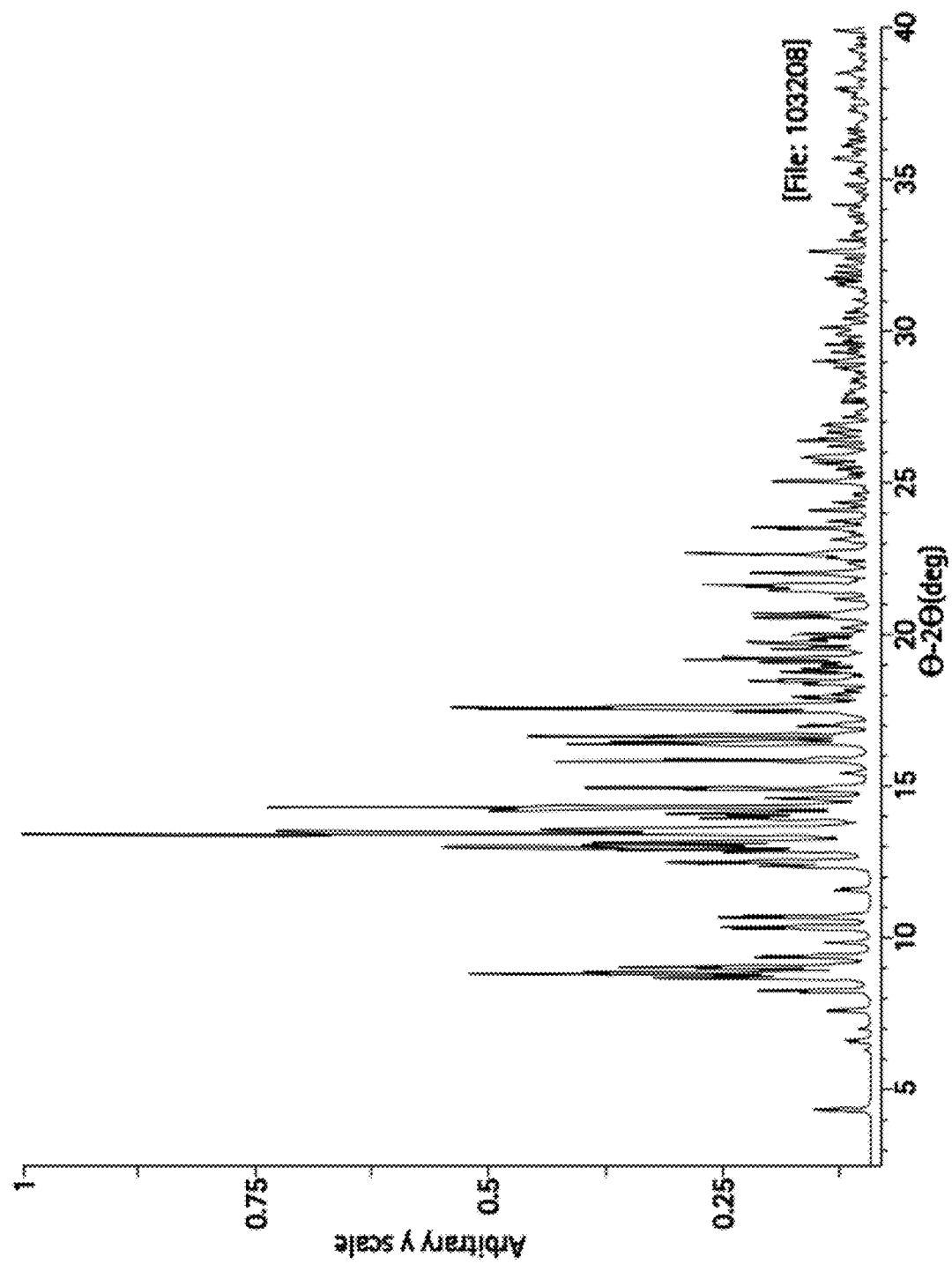
FIG. 17 shows the calculated X-ray powder pattern of Form A
Figure 18:
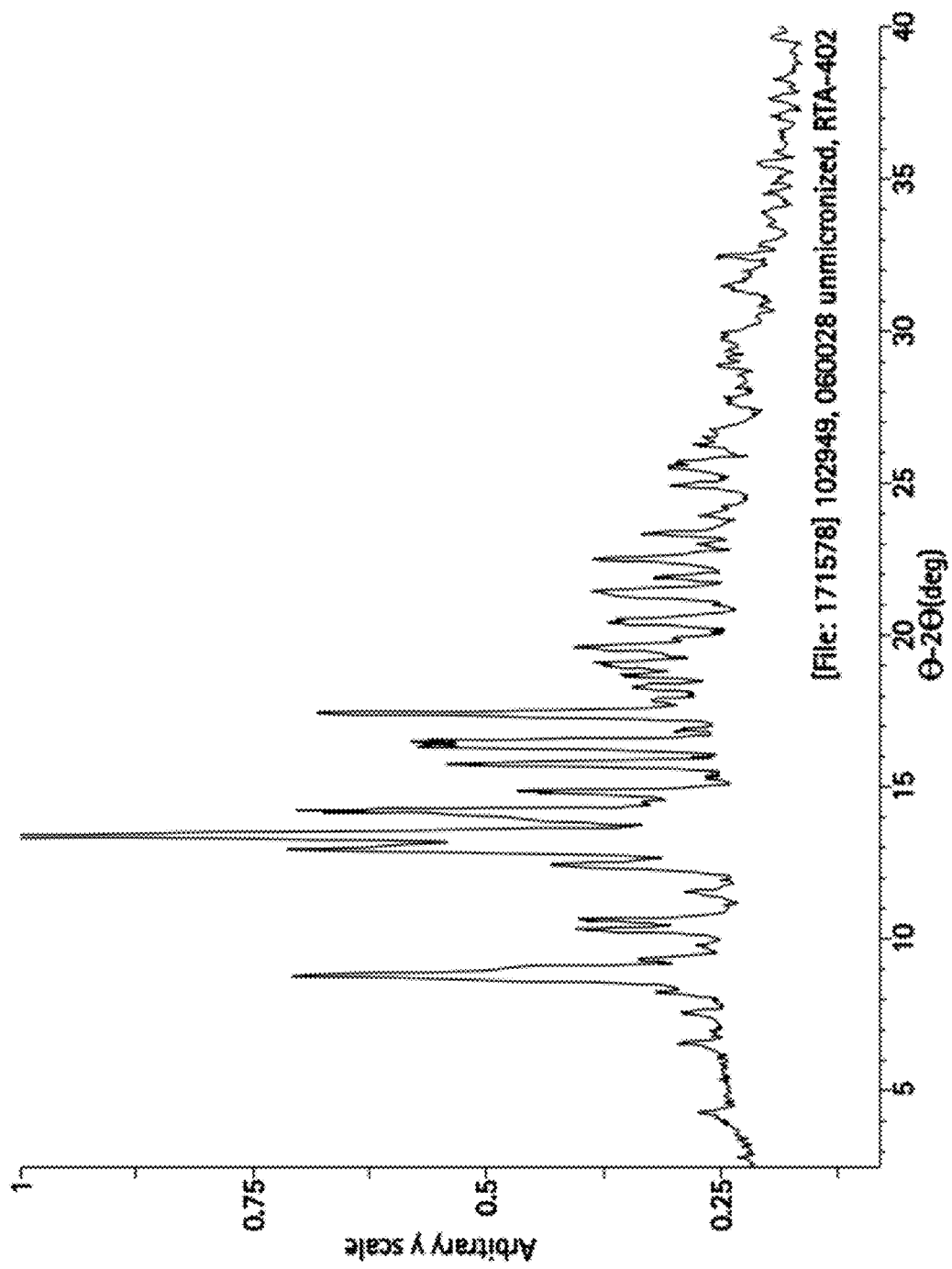
FIG. 18 shows the experimental XRPD of Form A.
Figure 19:
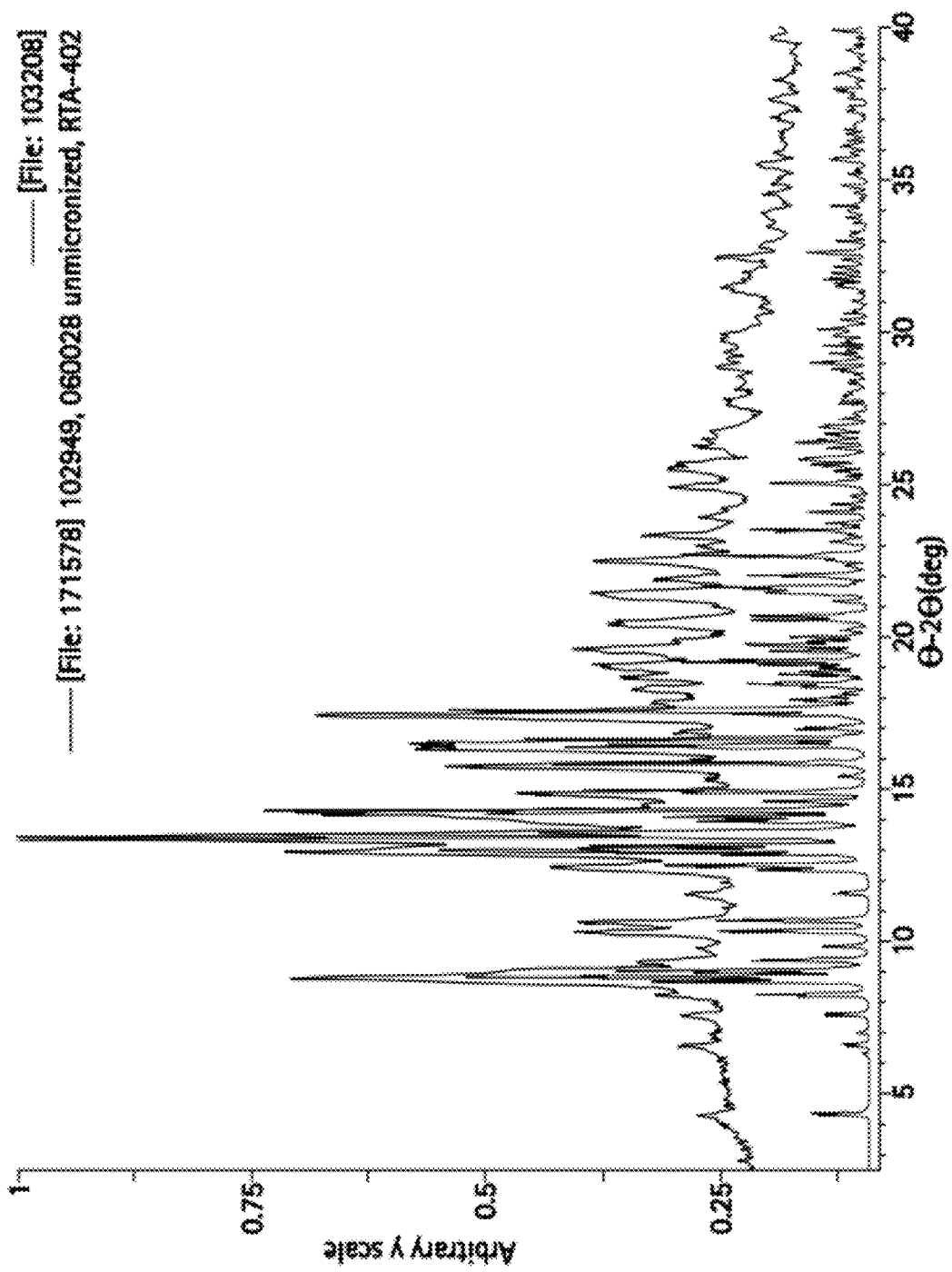
FIG. 19 presents a comparison of the calculated and experimental XRPD patterns for Form A CDDO methyl ester.

The calculated XRPD pattern of CDDO methyl ester, generated from the single crystal data, is provided in FIG. 17. The experimental XRPD pattern of CDDO methyl ester is shown in FIG. 18. Characteristic peaks for the Form A XRPD pattern are provided in Table 17. A comparison of the calculated and experimental XRPD patterns (FIG. 19) reveals all peaks in the experimental patterns are represented in the calculated XRPD pattern, indicating the bulk material is likely a single phase. The slight consistent shifting observed in peak location is likely due to the fact that the experimental powder pattern was collected at room temperature, and the single crystal data were collected at 150° K. Low temperatures are used in single crystal analysis to improve the quality of the structure.

In summary, the single crystal structure of CDDO methyl ester Form A was determined to confirm to the proposed molecular structure. The space group was determined to be P4$_3$2$_1$2 (no. 96). The structure of CDDO methyl ester consists of three molecules packed in a helical nature down the crystallographic b axis. All peaks in the experimental patterns are represented in the calculated XRPD pattern, indicating the bulk material is likely a single phase.

Figure 3:
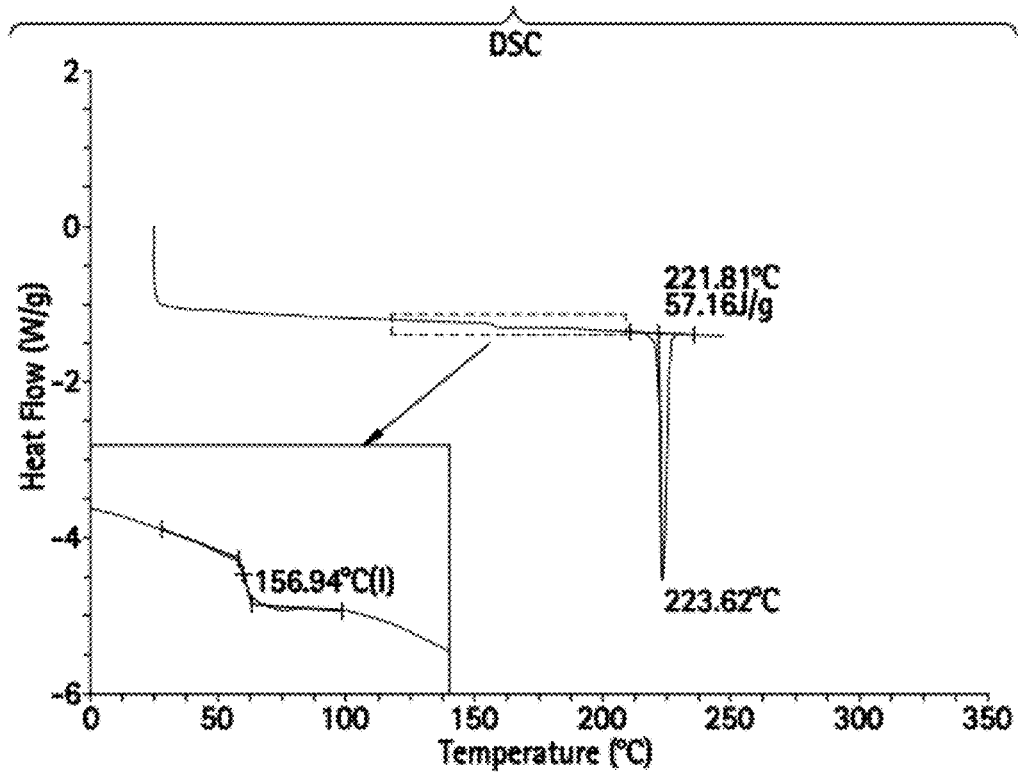
FIG. 3 shows the DSC and TG curve of CDDO methyl ester (Form A).
Figure 3:
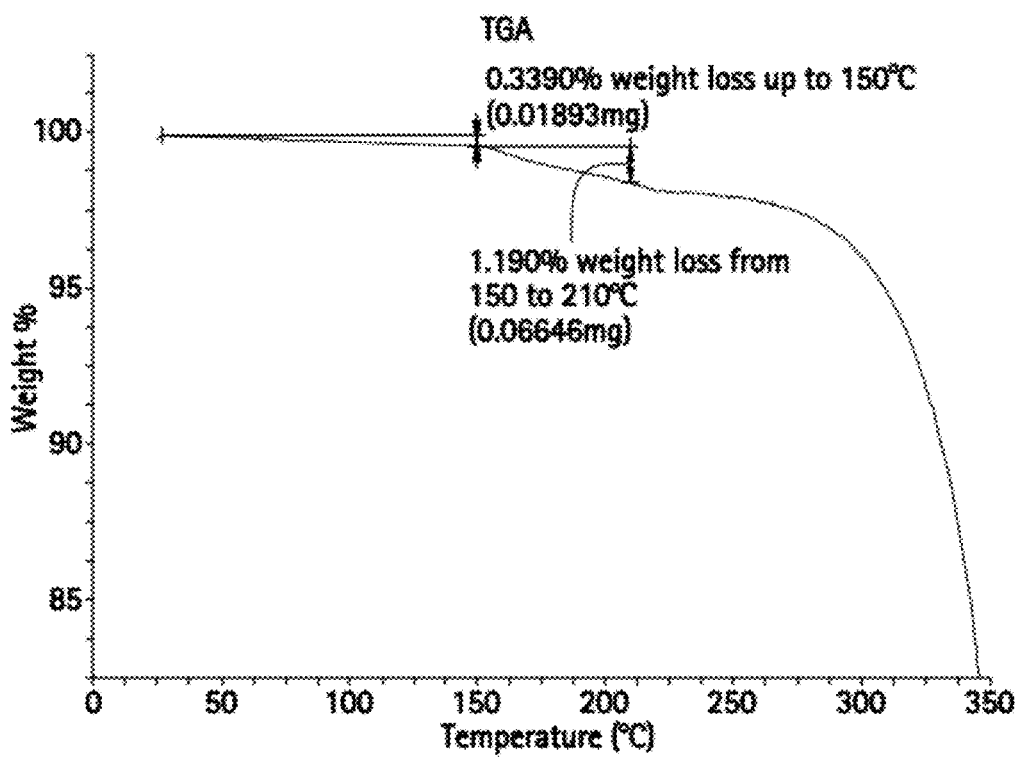
Figure 4:
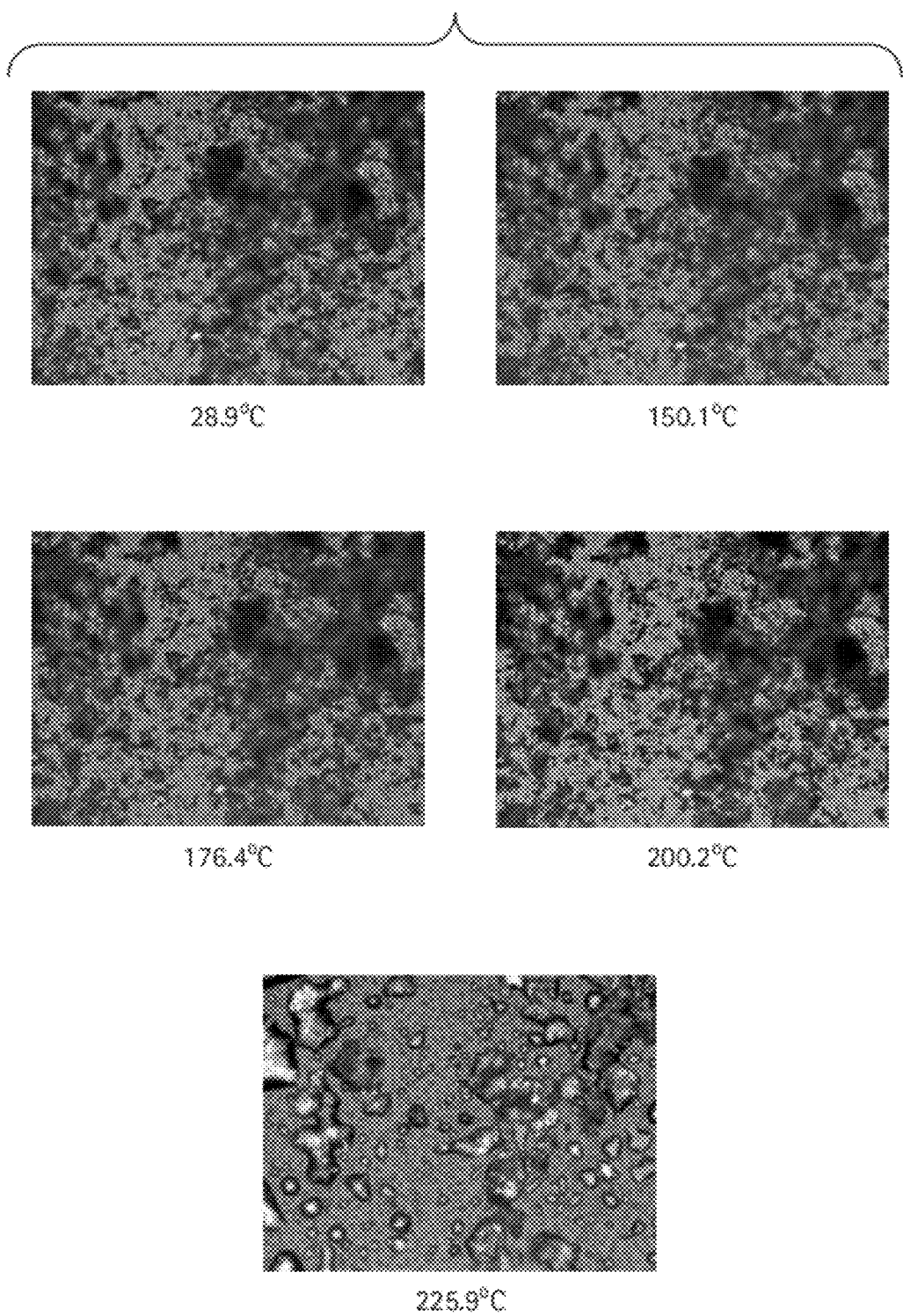
FIG. 4 shows the hot stage analysis of Form A—unmicronized.

The thermal data for Form A are shown in FIG. 3. The DSC curve shows a baseline shift at approximately 157° C. and an endotherm with an onset temperature of approximately 222° C. (signal maximum at ~224° C.). The event at ~224° C. was confirmed as the melt by hot stage microscopy (FIG. 4). The thermogravimetry (TG) curve exhibits a negligible weight loss of 0.34% up to 150° C., followed by a weight loss of 1.2% from 150 to 210° C. Karl Fischer data shows the material to contain approximately 0.38% residual water, consistent with the initial weight loss observed by TG.

Figure 5:
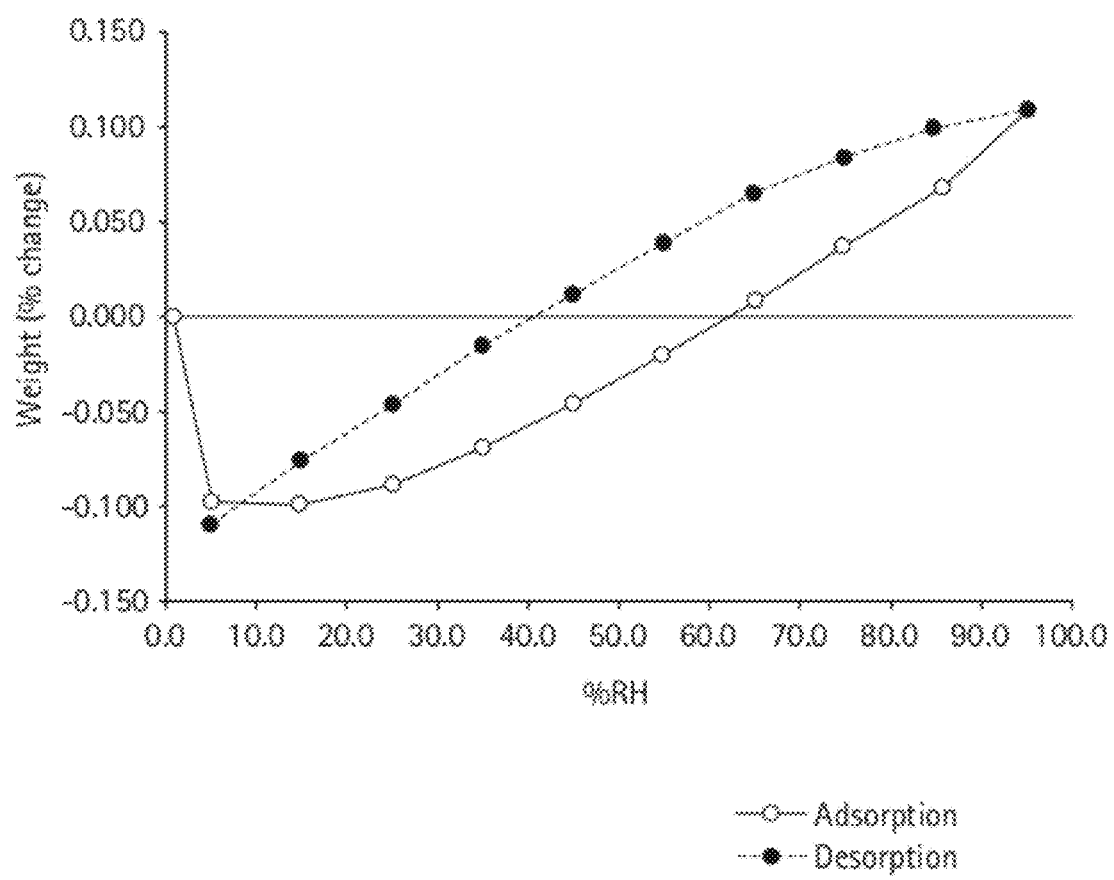
FIG. 5 shows the dynamic vapor sorption isotherm of Form A—unmicronized.

The DVS data indicate that Form A is not hygroscopic (FIG. 5). The material shows a negligible weight change throughout the experiment. The resulting material was analyzed by XRPD and is Form A.

Figure 6:
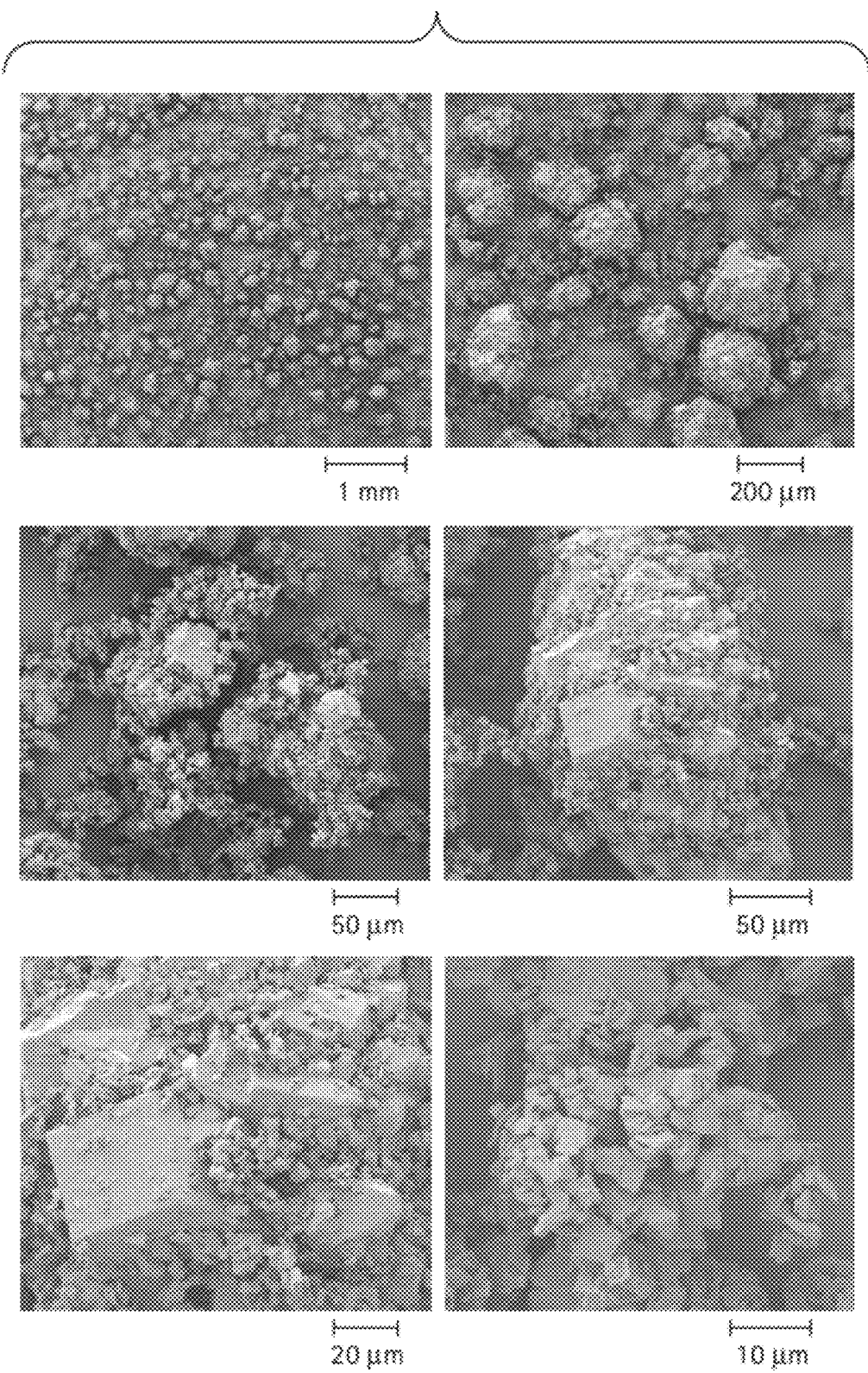
FIG. 6 shows the SEM images of Form A—unmicronized.

SEM images are shown in FIG. 6. Several habits are observed, including pyramidal, tablet, and plate-like.

Figure 7:
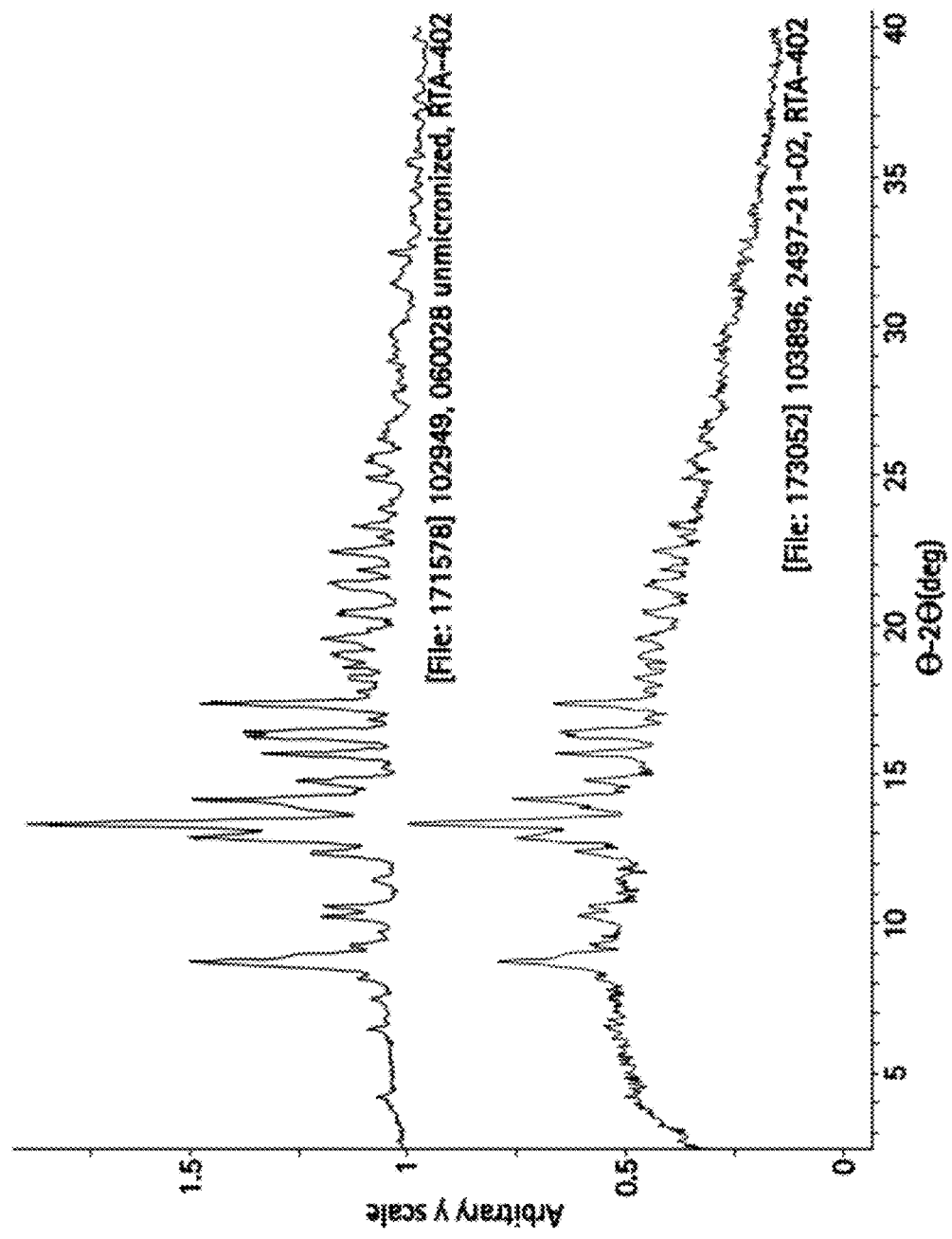
FIG. 7 shows Form A before (top) and after (bottom) stress at 195° C.

The physical stability of Form A at various conditions was investigated (Table 7). Samples stressed at either 25° C./60% RH or 40° C./75% RH for 7 days both showed a negligible weight change (0.6% loss and 0.2% gain, respectively) suggesting that Form A is not hygroscopic. Two samples were ground on a ball mill for approximately 20 minutes, one dry and one with a small amount of water. All samples were reanalyzed by XRPD and remained Form A. A sample was stressed at 195° C. for 15 minutes and showed a 2% weight loss. The XRPD of the resulting material is similar to that of Form A; however, an increase in the baseline noise is evident (FIG. 7).

Figure 8:
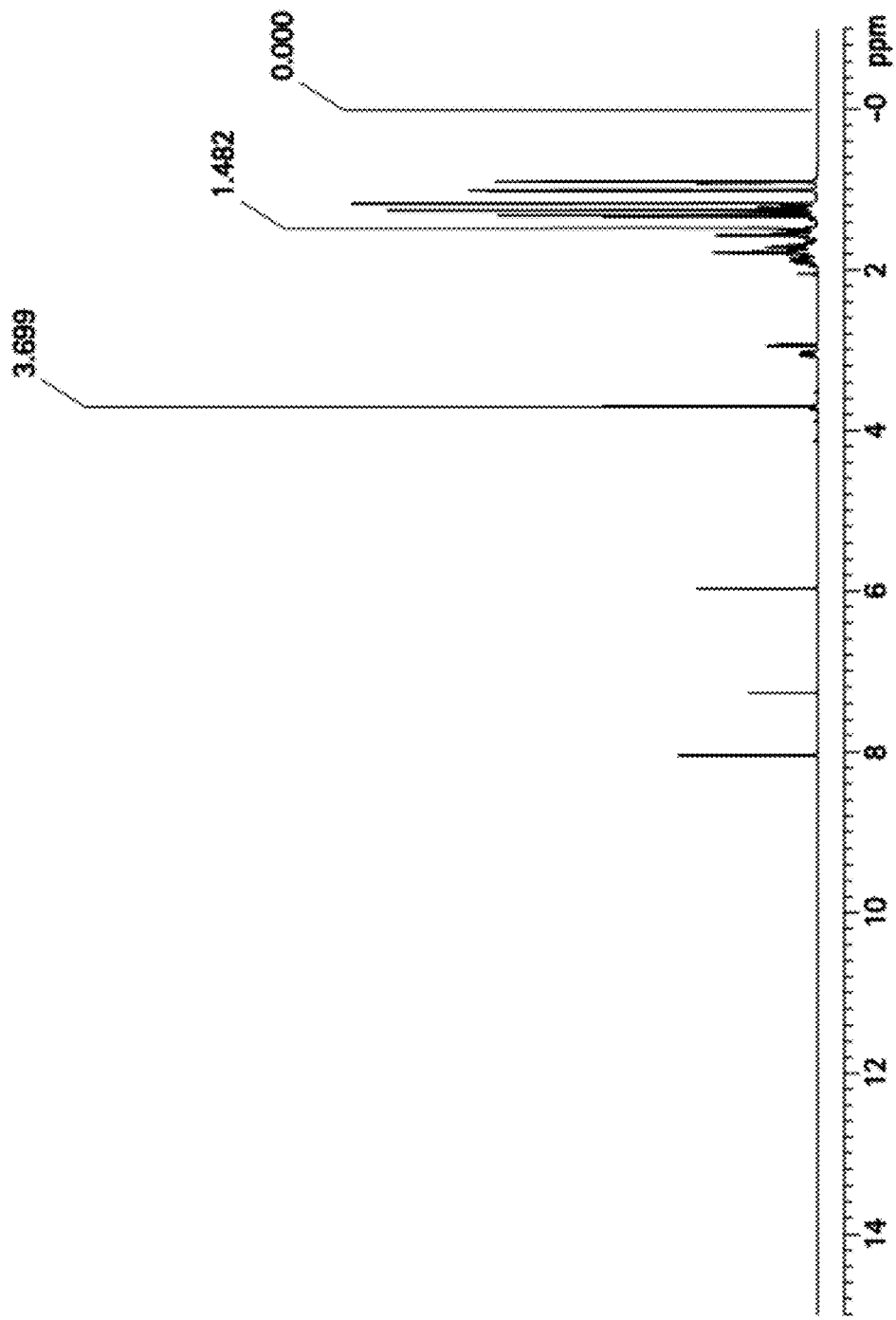
FIG. 8 shows the NMR spectrum of Form A—unmicronized.

The solution NMR spectrum is shown in FIG. 8. The spectrum is consistent with the structure of CDDO methyl ester. Peaks at approximately 1.6 and 7.3 ppm are assigned to water and chloroform (due to exchange), respectively.

Form A is unsolvated and not hygroscopic, therefore, and it melts at approximately 228° C., based on observations of analyst during hot stage microscopy.

EXAMPLE 4

Characterization of CDDO-methyl Ester—Form A (Micronized)

Figure 2:
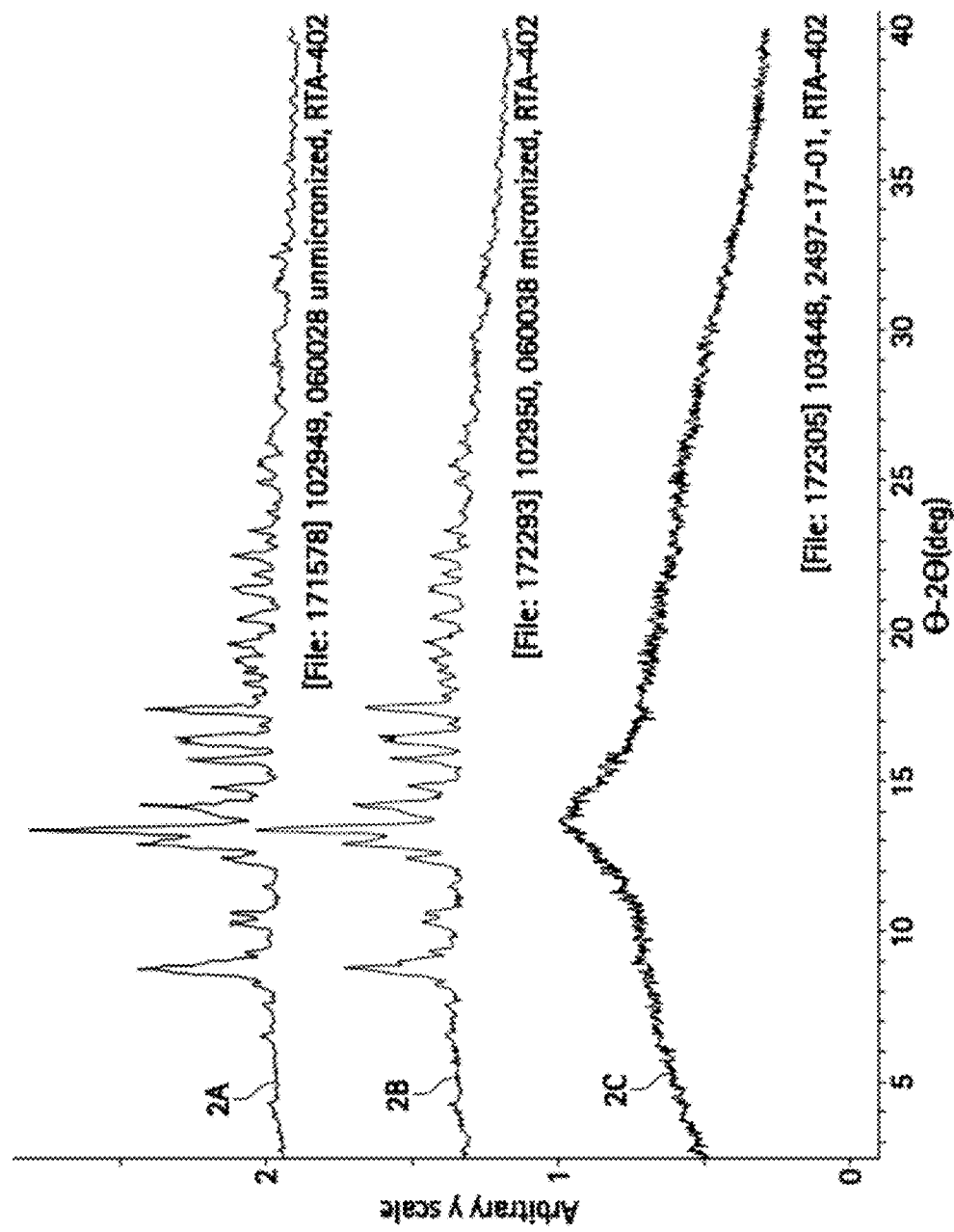
FIG. 2 presents the XRPD pattern of Form A (top) and Form B (bottom). From top to bottom: unmicronized Form A; micronized Form A; and Form B.

Micronized Form A CDDO methyl ester was determined to be Form A by XRPD (FIG. 2, Table 1). Micronized material can be produced by conventional methodology, well known to the field, such as air jet milling. These findings appear to indicate that micronization does not affect Form A in order to alter its XRPD pattern.

EXAMPLE 5

Characterization of CDDO-methyl Ester—Form B

Form B material can be prepared from lyophilization, melt/quench, and several other evaporation experiments, as provided in Table 3.

Figure 9:
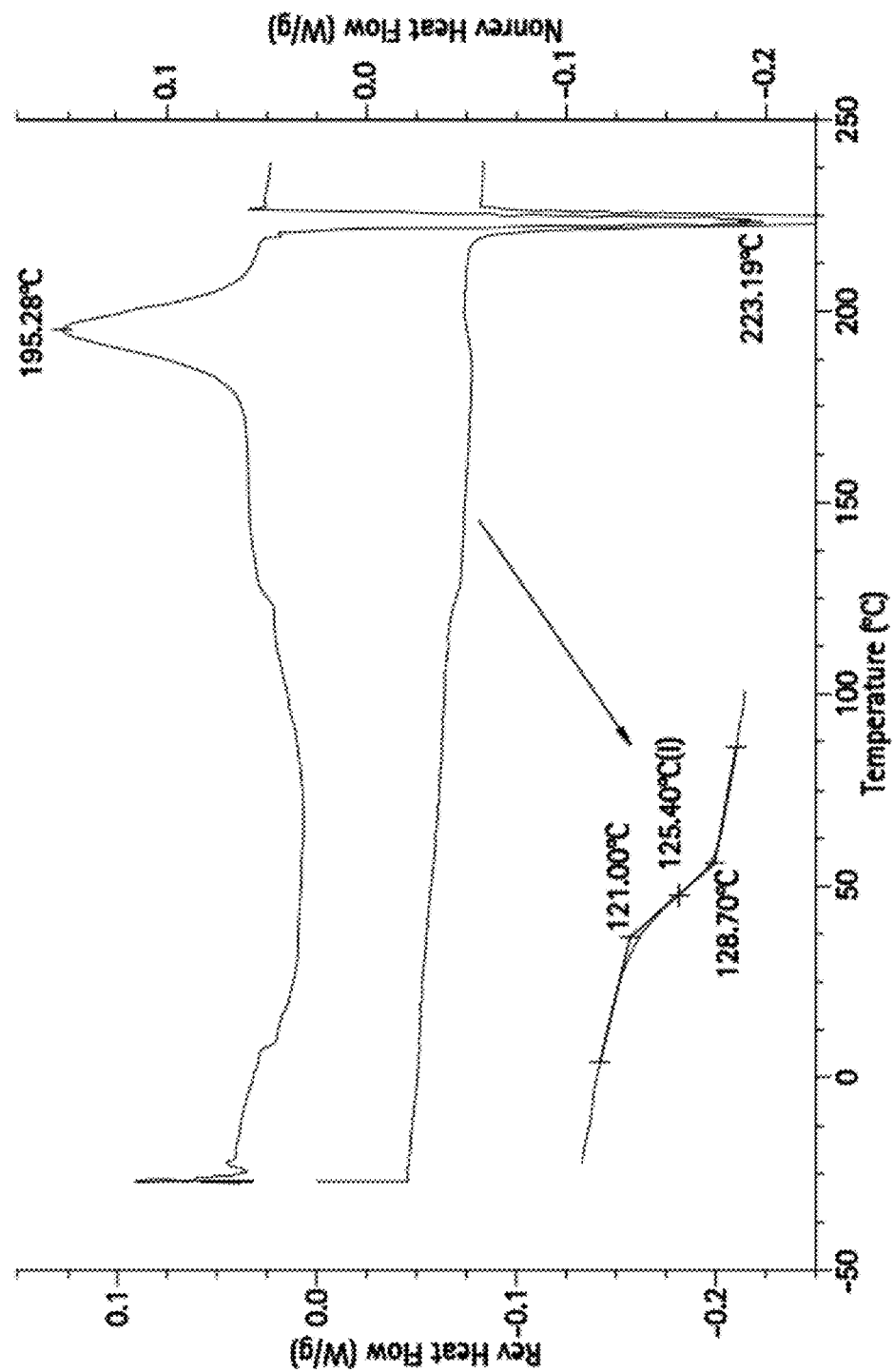
FIG. 9 shows the MDSC curve of Form B CDDO methyl ester.

The modulated DSC (MDSC) data are shown in FIG. 9. The reversible curve shows a glass transition temperature (Tg) at approximately 125° C. The non-reversible curve shows an exotherm with signal maximum at 195° C. and an endotherm with signal maximum at 223° C. The non-reversible events are most likely due to crystallization of the Form B material (exotherm) followed by the melt of the crystallized material (endotherm).

The physical stability of Form B material at various conditions was investigated (Table 9). Samples stressed at 22°

Figure 10:
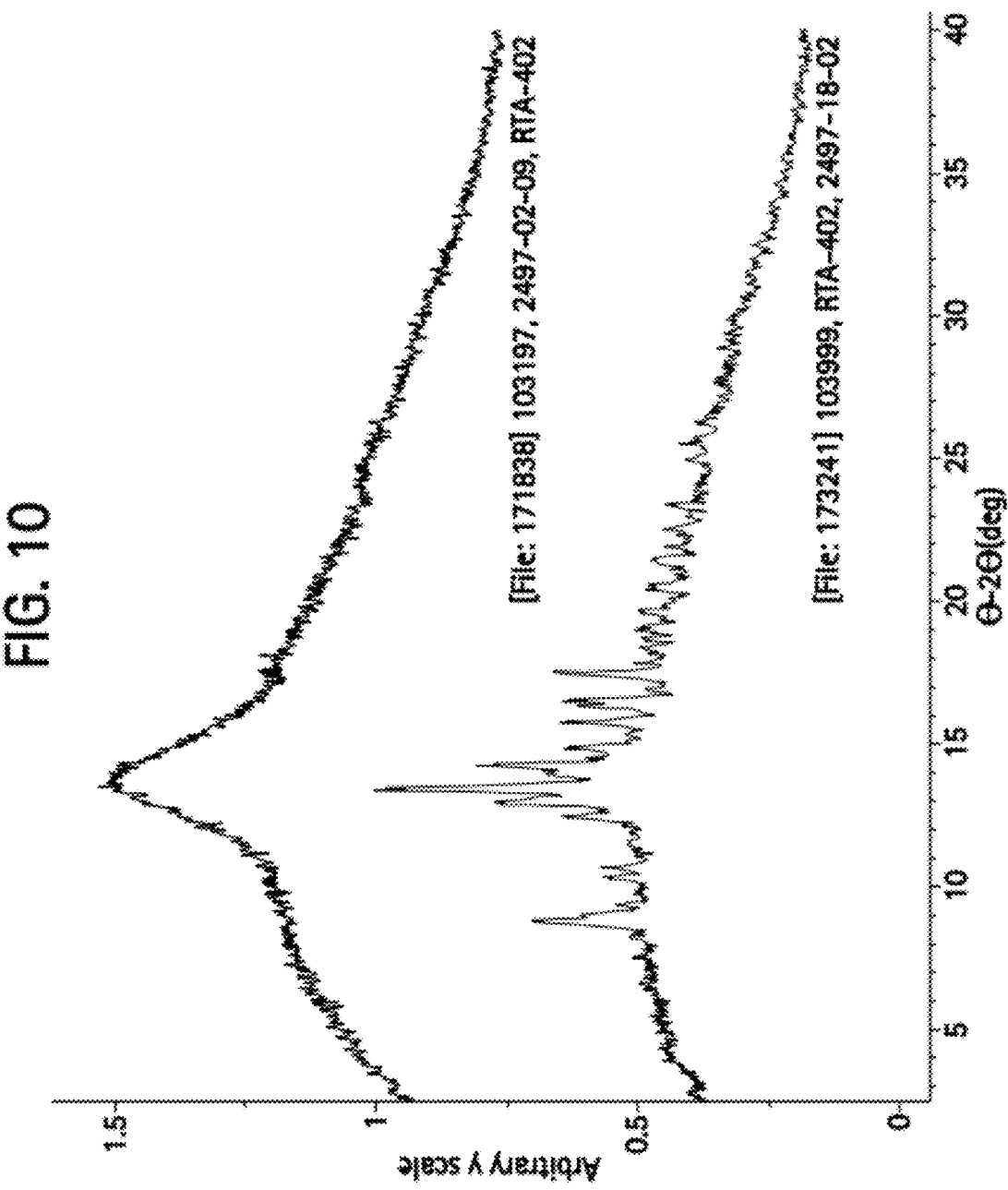
FIG. 10 shows Form B CDDO methyl ester before (top) and after (bottom) thermal stress at 200° C./ambient RH for 60 minutes.

C./97% RH, 40° C./75% RH, 80° C./0% RH, and 195° C./ambient RH remained Form B. Stressing the material at 200° C./ambient RH for 60 minutes produced Form A plus minor Form B material (FIG. 10).

Figure 11:
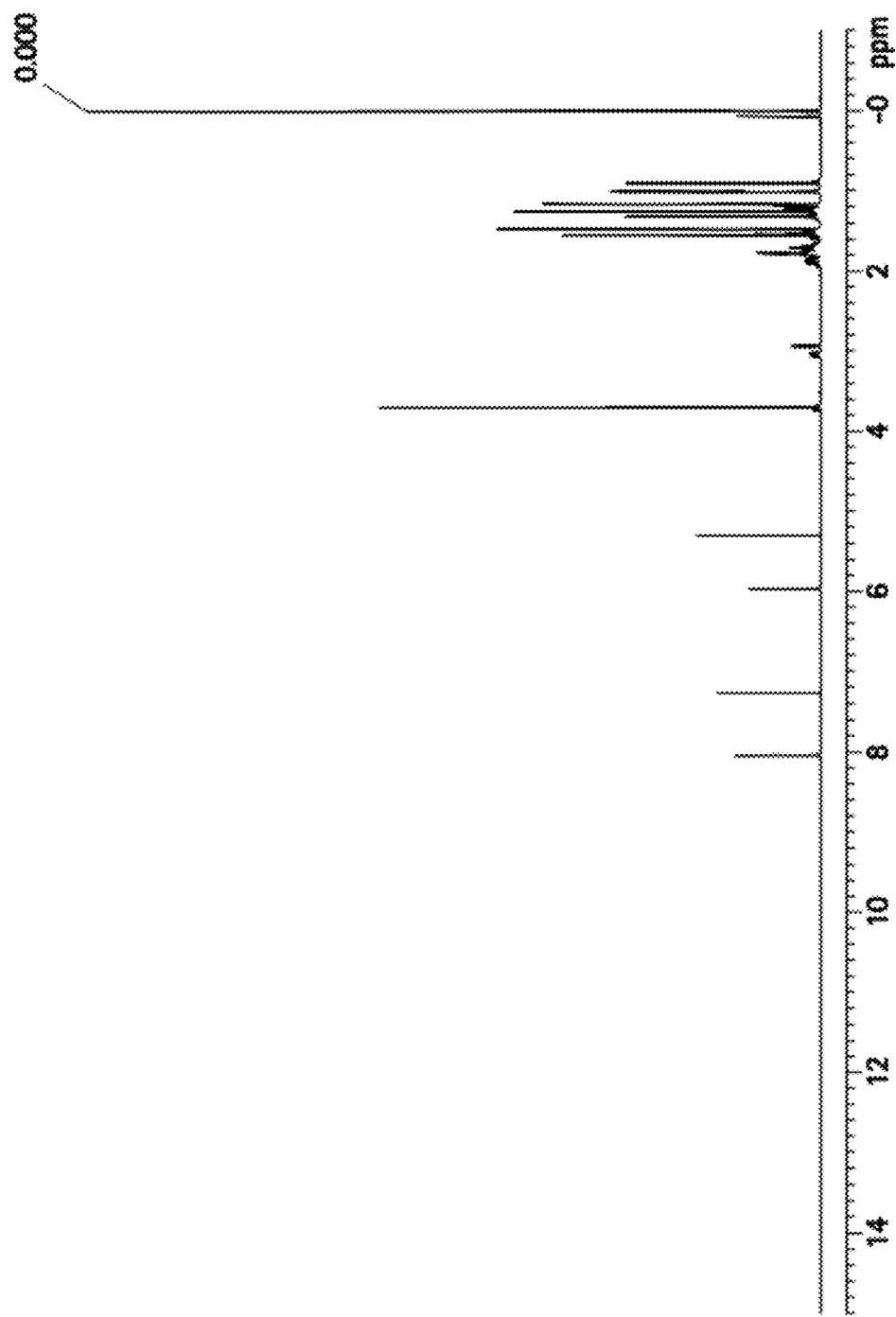
FIG. 11 shows the NMR spectrum of Form B CDDO methyl ester.

The solution NMR spectrum is shown in FIG. 11. The spectrum is consistent with the structure of CDDO methyl ester. Peaks at approximately 1.6, 5.3, and 7.3 ppm are assigned to water, dichloromethane, and chloroform, respectively.

Form B is not hygroscopic, crystallizes to Form A at approximately 200° C., and has a glass transition temperature (Tg) of approximately 125° C.-130° C.

In summary, Form B is not hygroscopic. The MDSC data indicates that the glass transition temperature (Tg) of Form B is approximately 125° C.-130° C. Form B material crystallizes to Form A when stressed at approximately 200° C.

EXAMPLE 6

Stability Studies for Form B CDDO-methyl Ester and CDDO-methyl Ester Polymer Excipient Dispersions (i) Purified Form B Studies Form B CDDO-methyl ester was subjected to varying stress conditions. Table 15 provides some of the results from these studies. Form B CDDO-methyl ester produced by a useful but less preferred embodiment of this invention, involving the use of ethyl acetate as solvent, shows considerable stability. Nevertheless, testing of Form B samples produced in the presence of ethyl acetate revealed the formation of Form A after 28 days of storage at temperatures of 60° C. and above. By contrast, all samples produced in accordance with a preferred embodiment of this invention, Example 11 below being illustrative thereof, retained amorphous characteristics after stress testing under particularly rigorous conditions (see Table 15). These studies show the surprising stability of the Form B material, especially when it is prepared in accordance with the aforementioned, preferred embodiment.

Figure 28:
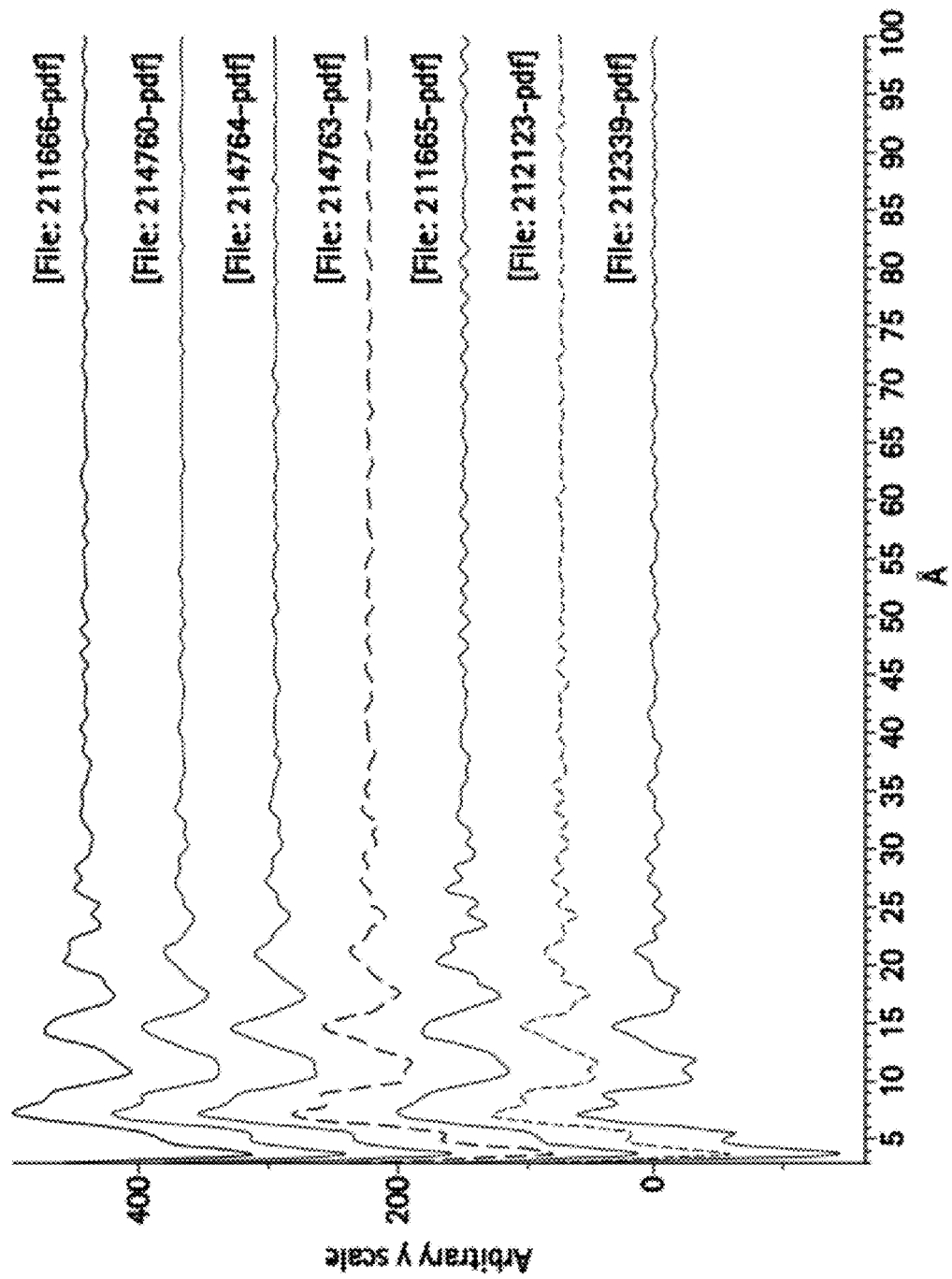
FIG. 28 is an overlay representation of X-ray amorphous patterns for different preparations of Form B, showing substantial uniformity among the preparations.

In addition, Form B samples prepared under varying conditions were analyzed to determine whether they have similar chemical properties. As described above, that is, Form B samples were prepared by cryogrinding, melt quench, and spray drying methods. In addition, unmicronized Form B was micronized to produce micronized Form B. PDF analysis was performed on the samples (FIG. 28), which were determined to be glassy in nature.

(ii) Studies with CDDO-Me Dispersion Preparations

Studies were performed to compare the performance of different Form B :polymer solid dispersions produced by spray drying. The product attributes studied included stability and drug dissolution profile.

Different polymers were used at three active pharmaceutical ingredient (API) to polymer ratios (20:80; 40:60 and 60:40% w/w).

The following three polymers were selected:
Methacrylic Acid-Ethyl Acrylate Copolymer (1:1)
Copovidone [1-vinyl-2-pyrrolidone-vinyl acetate copolymer (3:2)]
Hypromellose Phthalate.

Solutions of CDDO-Me, either Form A crystalline material or Form B material, and the polymer chosen for study were dissolved in a suitable solvent at the appropriate weight ratios, typically to afford from 10-20% by weight of solids in solution. The solvent typically employed was acetone. The resulting solutions were spray dried by means of a laboratory scale spray dryer (BÜCHI, model B-290), equipped with a two-fluid nozzle, using nitrogen as a drying and carrier gas. Carrier gas inlet temperatures of 65-85° C. and outlet temperatures of 50-60° C. typically were employed. The solids were collected and the spray dried powders were post-dried under vacuum, further to reduce the levels of the organic solvents.

The spray dried powders were analyzed for the level of residual organic solvents, glass transition temperature ($T_g$) and bulk density. After post-drying the powders were also analyzed for purity, water content, average particle size, absence of crystalline material by X-ray powder diffraction (XRPD) and dissolution profile.

The physiochemical characteristics of the dispersions were evaluated after short term stressing (after 5 days, 40° C./75% RH) by XRPD and modulated differential scanning calorimetry (mDSC).

These studies found that the glass transition temperature, $T_g$, decreased during short term stressing, probably due to the uptake of moisture over the course of stressing. The decrease was more pronounced with the formulations having low CCDO methyl ester:polymer ratios. For samples before the short-term stressing, one or two endothermic transitions were observed at higher temperatures, although these temperatures are somewhat lower than the ones observed initially. The enthalpy associated with these transitions decreased as polymer content decreased. This is an indication that this transition is most probably related with the polymer and not with the melting of a crystalline form. In fact, for dispersions produced with PVP/VA, the temperature of this endothermic transition was similar to the one observed for pure excipient, as received from the manufacturer. In each case, the XRPD profile after stressing continued to be the characteristic halo pattern centered around 13.5°2θ, and no peaks associated with the crystalline form were detected.

Further spray drying studies on two formulation were conducted, using larger scale spray drying equipment. In these cases, a Niro pilot scale dryer model PSD-1 (mobile minor 2000) was employed. Also employed were equivalent nozzle and spray drying conditions to those described above. Tables 20 and 21 summarize the solutions prepared for spray drying and their characteristics following spray drying. The formulations showed a lower $T_g$, relative to pure Form B, due to the formulation including polymers with a lower $T_g$ than Form B.

EXAMPLE 7

Administration of CDDO Methyl Ester

Form B Versus Form A in Cynomolgus Monkeys

In phase 1 of this study, a quantity of hard gelatin capsules, containing pure micronized Form A CDDO-Me or pure micronized Form B CDDO-Me, were prepared by (i) adding an appropriately weighed quantity of the pure form of the drug substance to a size 1 hard gelatin capsule and then (ii) closing the capsule. No additional excipients were employed. Either CDDO methyl ester Form B or Form A was administered orally in a gelatin capsule to Cynomolgus monkeys (dose=4.1 mg/kg in all cases).

Figure 20:
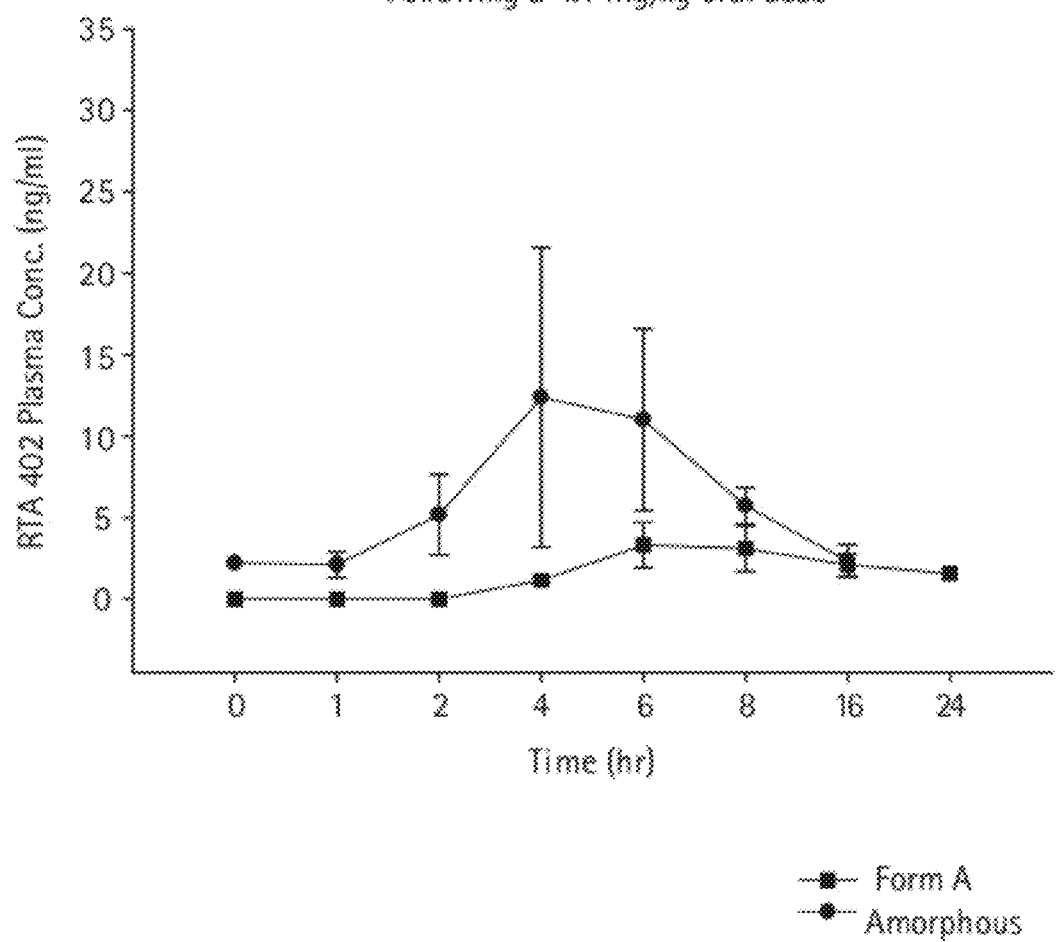
FIG. 20 shows a representative plot of the area under the curve for Form A and Form B, following a 4.1 mg/kg oral administration to cynomolgus monkeys. Each datum point represents the mean plasma concentration of CDDO methyl ester in 8 animals. Error bars represent the standard deviation within the sampled population.
Figure 21:
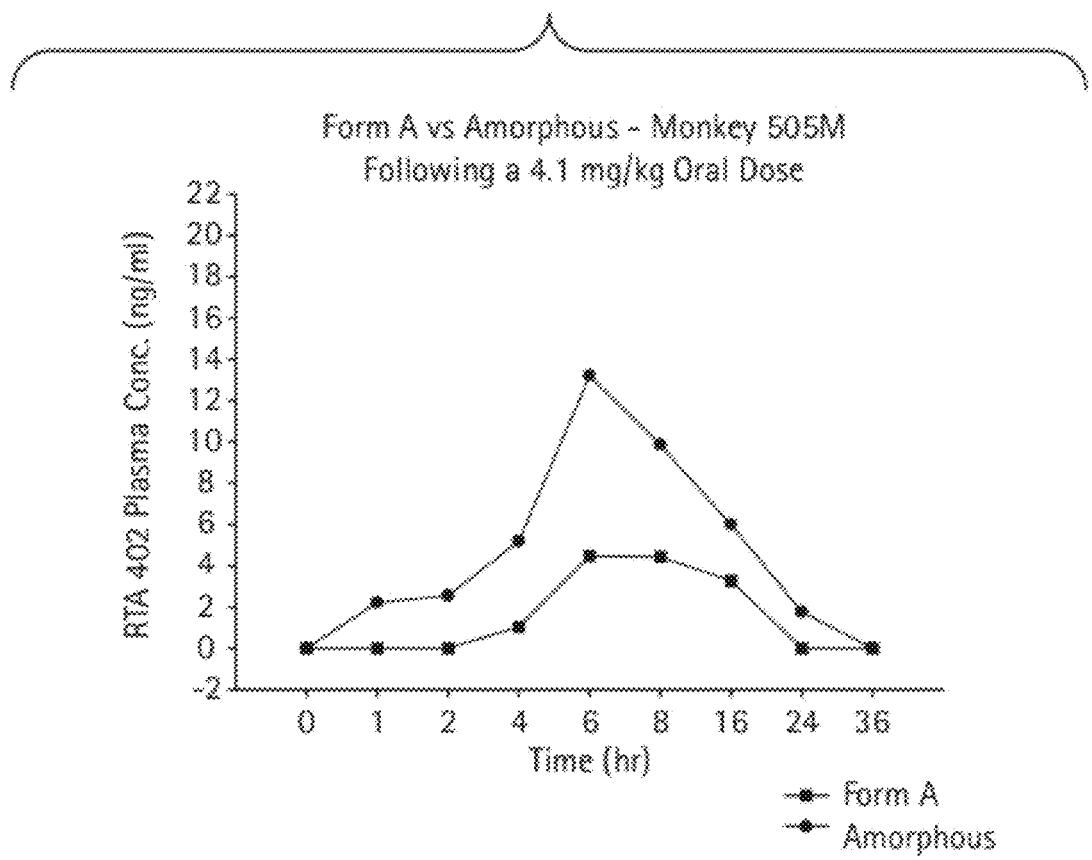
FIG. 21 shows a comparison of plasma concentration of Form B CDDO methyl ester versus Form A in Animal #505M (top panel) and animal #507F (bottom panel).
Figure 21:
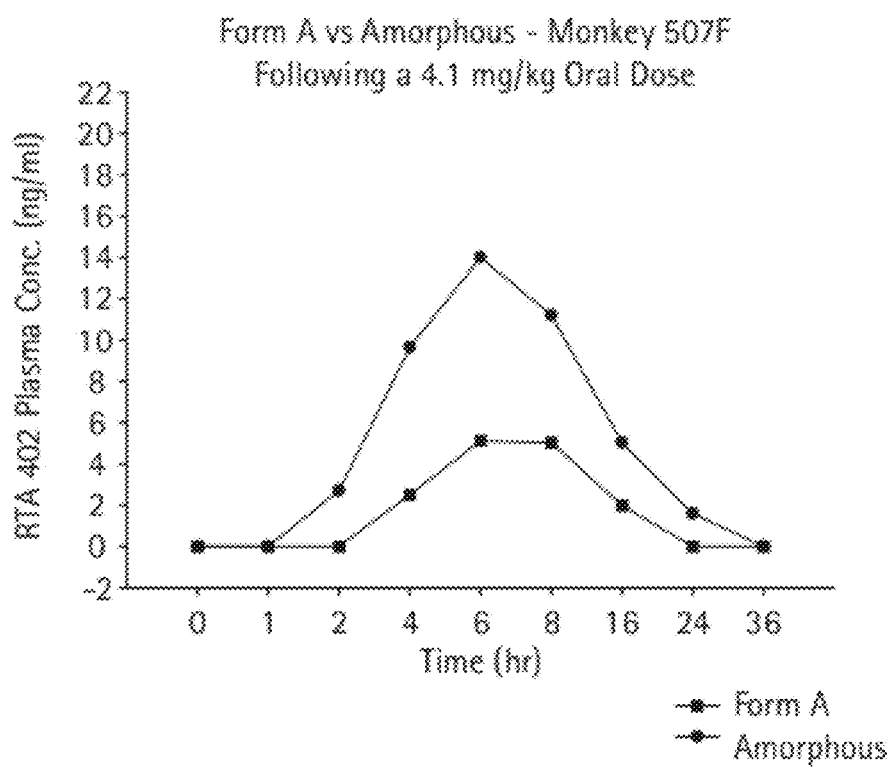
Figure 22:
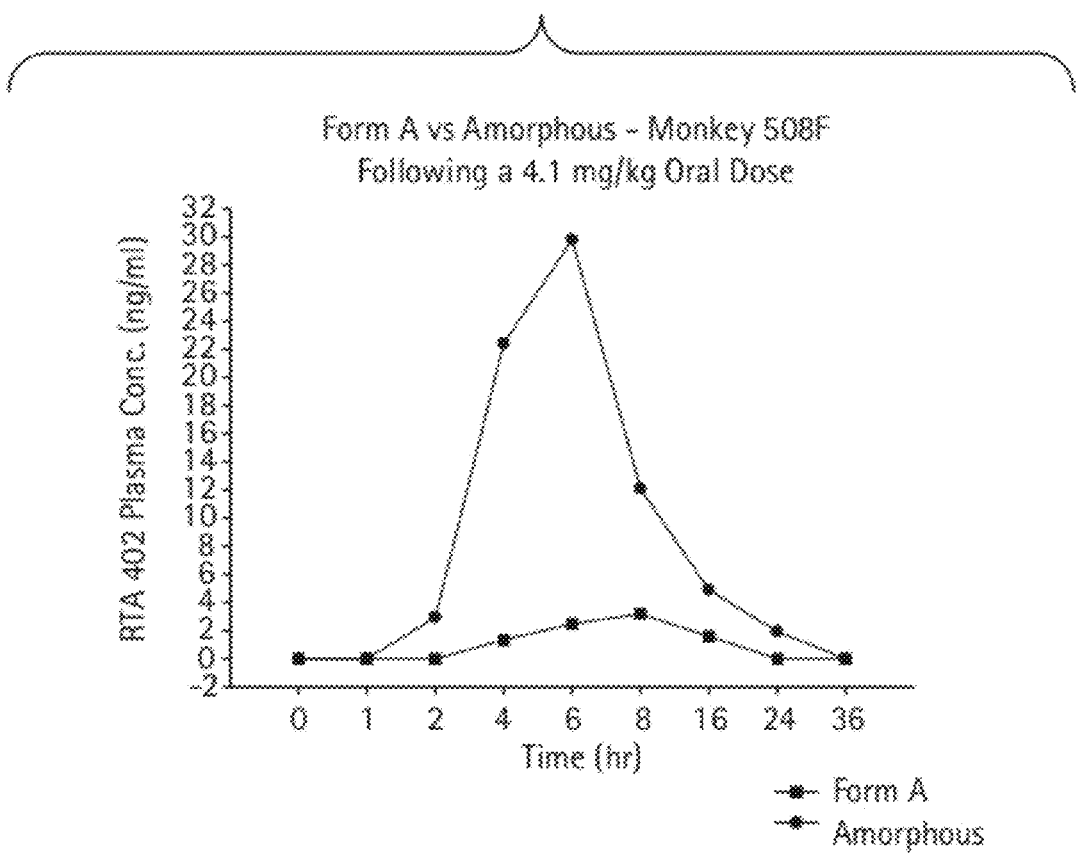
FIG. 22 presents a comparison of plasma concentration of Form B CDDO methyl ester versus Form A between Animal #508F (top panel) and animal #502M (bottom panel).
Figure 22:
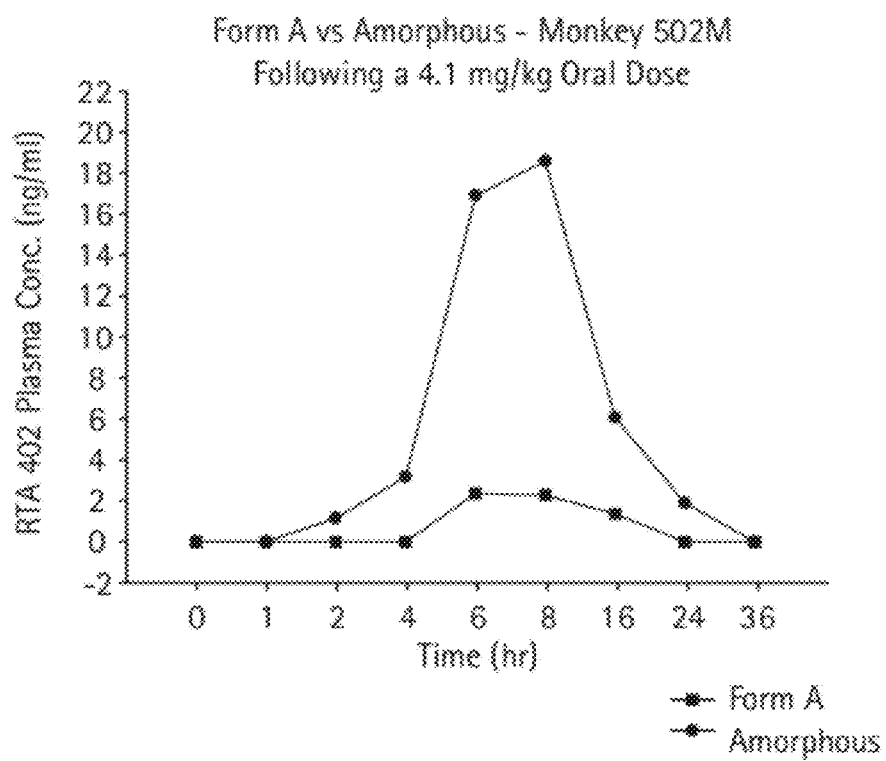

Administration of the CDDO methyl ester Form B provided a median exposure which was approximately 520% greater than the equivalent dose of CDDO methyl ester Form A in monkeys. Table 11 compares the individual animal drug exposures. A crossover design was implemented in this study to increase the 'n' value and to enhance data reliability. A wash-out period of 1 week was implemented during the crossover. FIG. 20 demonstrates the achieved plasma concentrations of both forms of CDDO methyl ester over time in the sampled population. FIG. 21 represents comparative CDDO methyl ester plasma concentrations of animals #505M and #507F. FIG. 22 represents comparative CDDO methyl ester plasma concentrations of animals #508F and #502M.

To assess further the comparative bioavailability of the oral dosage forms of CDDO-methyl ester, including those containing CDDO-methyl ester excipient dispersions, two additional study phases 2 and 3 were conducted, as detailed below. These studies included some of the CDDO-Me Form B—polymer dispersions described in Example 6. All formulations included commonly used formulation additives.

Phase 2:

An aqueous suspension of nanocrystalline CDDO-Me was produced, starting from a sample of micronized Form A material. A Retsch® Planatory Ball Mill model PM 400, containing zirconia balls of 2 mm average size, was charged with 25 gm of micronized CDDO-Me (average particle size distribution of 6.1 uM), 5 gm of docusate sodium, 1 gm of Tween 80, and 68.3 gm of water. Grinding was initiated at approximately 400 RPM and was continued for 2 hours. A particle size distribution (PSD) determination using a laser light granulometer indicated an average PSD of 0.37 μM was obtained. To this thick suspension were added 1 gm of microcrystalline cellulose and 0.2 gm of xantham gum, with brief mixing, and the suspension was stored refrigerated.

The ball milled nano suspension was spray coated onto a dry excipient blend in a laboratory scale Aeromatic Strea 1 fluid bed, with the top spray assembly having a pray nozzle size of 0.4 mm. The inlet temperature was set at 55° C. The exhaust temperature range during spraying was 32 to 35° C. The resulting granulation was dried for approximately 5 minutes, until the exhaust temperature reached 38° C. (Attachment 3-5). The composition of the coated materials is given below.

Theoretical Composition of the nanocrystalline 30 mg CDDO-Me Formulation

| Item# | Ingredient | % | mg/unit |
|---|---|---|---|
| 1 | CDDO-Me | 5.7 | 19 |
| 2 | Tween 80 | 0.12 | 0.4 |
| 3 | DOS | 1.14 | 3.8 |
| 4 | Microcrystalline Cellulose in suspension | 0.21 | 0.7 |
| 5 | Xanthan Gum | 0.03 | 0.1 |
| 6 | Microcrystalline Cellulose in granulation | 24.4 | 81.55 |
| 7 | Starch Pregel | 58.5 | 195.3 |
| 8 | Povidone K29/32 | 0.5 | 1.75 |
| 9 | Crospovidone | 8.4 | 28 |
| 10 | Colloidal Silicon Dioxide | 0.5 | 1.75 |
| 11 | Magnesium Stearate | 0.5 | 1.75 |
| | Total: | 100.0 | 334.1 |

The resulting dry granulation was submitted for HPLC analysis to determine the assay of active ingredient. That assay was determined to be 14.4% (wt/wt), substantially higher than the theoretical value (5.7%). Based on the HPLC analysis, capsules were filled so as to afford a net CDDO-Me content of 30 mg.

The crystalline micronized Form A and amorphous, micronized Form B formulations were produced by a conventional dry powder blending process, using, as additives, microcrystalline cellulose, pregelatinized starch, crospovidone (functioning as a disintegrant), colloidal silicon dioxide, and vegetable grade magnesium stearate. Micronized CDDO-Me Form A of average PSD 6.1 μM was used for the Form A formulation, while micronized CDDO-Me Form B of average PSD 10.8 μM was employed for the corresponding CDDO-Me Form B formulation. The table below presents the quantitative composition of both formulations.

Form A and Form B 30 mg capsule Quantitative Composition

| Identity | % w/w | mg per capsule |
|---|---|---|
| CDDO-Me (Micronized) | 18.18 | 30.0 |
| Microcrystalline Cellulose | 18.55 | 30.6. |
| Pregelatinized Starch | 53.45 | 88.2. |
| Crospovidone | 8.72 | 14.4 |
| Colloidal Silicon Dioxide | 0.55 | 0.9 |
| Magnesium Stearate (Vegetable Grade) | 0.55 | 0.9 |
| Total Capsule Contents | 100.00 | 165 mg |

Each of 15 male Cynomolgus monkeys, Macaca fascicularis, received a single oral administration of CDDO-methyl ester (3 different formulations, 5 monkeys per formulation) at a target dose level of 10 mg/kg. The monkeys ranged from 1-3 years in age and 2.5-3.5 kg in size. Blood samples were collected up to 72 hours post-dose.

Phase 3:

The CDDO-Me excipient dispersions described in Example 6 were further formulated by a conventional dry powder blending process, using microcrystalline cellulose, lactose monohydrate, crospovidone (functioning as a disintegrant), and sodium lauryl sulfate as additives. The quantitative composition of each formulation appears below.

Composition of CDDO-Me excipient dispersions blended with addities in capsule formulation

| Component | 40% CDDO-Me/ 60% Methacrylic acid copolymer Type C | 60% CDDO-Me/ 40% PVP/VA | 60% CDDO-Me/ 40% HPMC-P |
|---|---|---|---|
| CDDO-Me Dispersion | 60.0% | 50.0% | 50.0% |
| Microcrystalline Cellulose | 12.8% | 16.0% | 16.0% |

-continued

Composition of CDDO-Me excipient dispersions blended with addities in capsule formulation

| Component | 40% CDDO-Me/ 60% Methacrylic acid copolymer Type C | 60% CDDO-Me/ 40% PVP/VA | 60% CDDO-Me/ 40% HPMC-P |
|---|---|---|---|
| Lactose monohydrate | 20.0% | 25.0% | 25.0% |
| Crospovidone | 6.4% | 8.0% | 8.0% |
| Sodium lauryl sulfate | 0.8% | 1.0% | 1.0% |
| Total Capsule Contents | 100% | 100% | 100% |
| Fill mass | 125 mg | 100 mg | 100 mg |

After a suitable wash-out period (7 to 10 days), the same 15 male Cynomolgus monkeys used in Phase 2 each received a single oral administration of CDDO-mehtyl ester (3 different formulations, 5 monkeys per formulation) at a target dose level of 10 mg/kg. Blood samples were collected up to 72 hours post-dose.

The below chart summarizes each phase of the study.

| Phase number | Route of administration | CDDO-Me formulation | Target dose level | Number of animals (males) |
|---|---|---|---|---|
| 2 | Oral (capsule) | Nanocrystalline Form A | 30 mg/per animal (10 mg/kg) | 5 |
|   |   | Amorphous micronized Form B |   | 5 |
|   |   | Crystalline micronized Form A |   | 5 |
| 3 | Oral (capsule) | PVP/VA Form B | 30 mg/per animal (10 mg/kg) | 5 |
|   |   | HPMC-P Form B |   | 5 |
|   |   | Methacrylic acid copolymer Type C-Form B |   | 5 |

The mean intravenous and oral doses received by male Cynomolgus monkeys and mean concentrations of CDDO-methyl ester are summarized below:

| Phase number | Formulation | Mean body weight (kg) | Mean dose (mg/kg) |
|---|---|---|---|
| 2 | PO (nanocrystalline Form A) | 2.89 ± 0.267 | 10.5 ± 0.971 |
|   | PO (amorphous micronized Form B) | 2.87 ± 0.177 | 10.5 ± 0.635 |
|   | PO (crystalline micronized Form A) | 2.91 ± 0.202 | 10.3 ± 0.702 |
| 3 | PO Form B (PVP/VA) | 2.98 ± 0.311 | 10.2 ± 1.06 |
|   | PO Form B (HPMC-P) | 2.93 ± 0.183 | 10.3 ± 0.627 |
|   | PO Form B (Methacrylic acid copolymer Type C) | 2.93 ± 0.142 | 10.2 ± 0.486 |

PO Oral administration by capsule.

Gelatin capsule size 2 was used to deliver the formulations in phase 2 and gelatin capsule size 1 was used for delivery in phase 3. The net drug content in each capsule was 30 mg, corresponding to a 10 mg/kg dosage of drug, based on an assumption that each monkey weighed 3 kg. The capsule was attached to a gavage, the animal was gavaged, and the capsule was released from the end of the gavage by air pressure from an empty syringe. A small amount of water (approximately 10 mL) was given orally after the administration of the last capsule.

Serial blood samples (approximately 1 mL) were removed from the femoral vein or artery of each animal and transferred into tubes containing $K_2$-EDTA at each of the following time points (actual times were recorded):

Phase 2 Pre-dose, 1, 2, 4, 8, 16, 24, 48 and 72 h post-dose
Phase 3 Pre-dose, 1, 2, 4, 8, 16, 24, 48 and 72 h post-dose All samples were thoroughly mixed following collection and placed on wet ice, prior to being refrigerated at approximately 4° C. CDDO-methyl ester concentrations in blood were analysed by HPLC-MS/MS.

Figure 30:
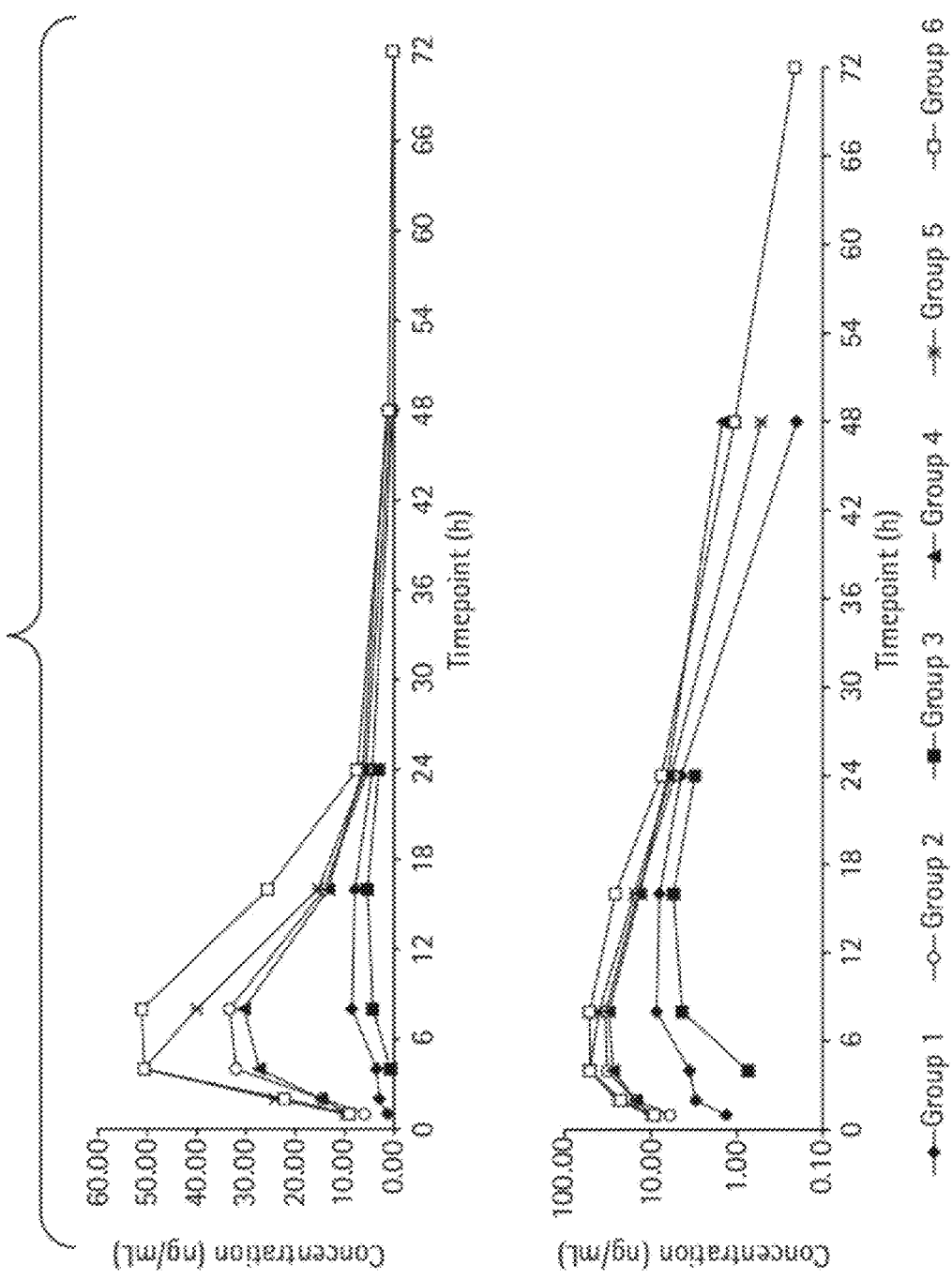
FIG. 30 shows the mean blood concentrations of CDDO-methyl ester following single oral administrations of CDDO-methyl ester capsules to male Cynomolgus monkeys (Phases 2 and 3).

The results are provided in Table 22 and in FIG. 30. For phase 2, Form B showed significantly better bioavailability to the two Form A formulations tested. Phase 3 results show that each of the CDD)-Me: polymer dispersion-based formulations had much higher bioavailability than either the micronized Form A or nanocrystalline Form A formulations. The methacrylic acid copolymer Type C and HPMC-P formulations showed the greatest bioavailability in the subject monkeys.

EXAMPLE 8

Characterization of Hemibenzenate Form of CDDO-Methyl Ester

Various experiments, replicating the last recovery step from the synthesis of CDDO methyl ester, were performed. Honda et al., 2000. The objective was the isolation of crystalline material from a solution mixture of (10:1) benzene/acetone.

Approximately 100 mg of CDDO-methyl ester was dissolved in 300 µL of benzene/acetone (10:1) and filtered through a 0.2-µm nylon filter. The solution was then sonicated using an ultrasonic processor for 10 minutes and allowed to evaporate at room temperature in an uncapped vial overnight. A clear gel formed and 100 µL of benzene/acetone (10:1) was added. The solution was submitted to sonication on an ultrasonic processor for approximately 30 minutes. A white precipitate formed. The solids were allowed to air dry.

In other experiments, approximately 200 mg of CDDO-methyl ester was dissolved in 0.8 mL of benzene/acetone (10:1) and filtered through a 0.2-µm nylon filter. The solution was then evenly divided into two 1-dram vials. Samples A and B were then allowed to fast evaporate at room temperature for a few hours. Sample A was capped and placed in a freezer. After the sample froze, the sample was allowed to thaw at room temperature. A small scratch was introduced using a spatula and the sample was allowed to evaporate at room temperature. White solids formed and were allowed to air dry. Sample B was capped, left at room temperature and was a clear solution after sitting at room temperature overnight. A small scratch was introduced using a spatula and the sample was allowed to evaporate at room temperature. White solids formed and were allowed to air dry.

Crystalline material, determined to be a hemibenzenate, was obtained from several of these experiments. As described above, minor disturbances, such as sonication or merely introducing a small scratch within the recovery vessel, will facilitate the crystallization of the benzene solvate (Table 12).

Figure 23:
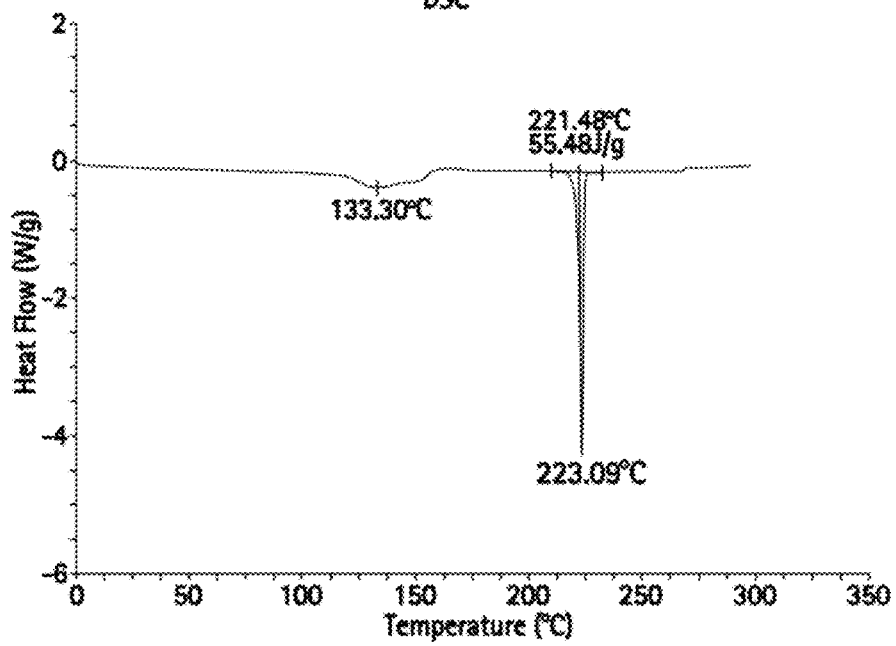
FIG. 23 depicts thermograms of CDDO methyl ester hemibenzene solvate.
Figure 23:
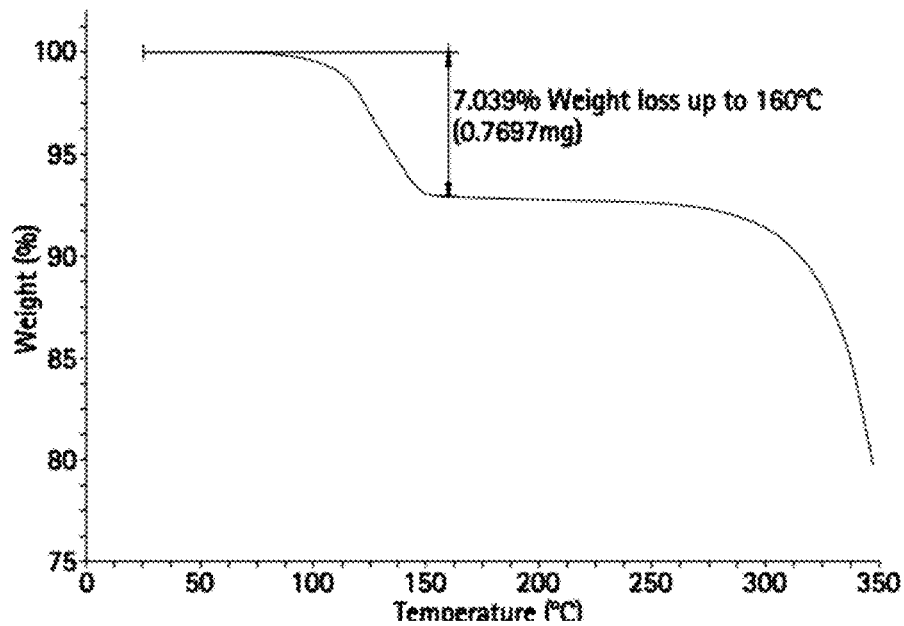

Characterization data of the hemibenzenate are summarized in Table 13. Characteristic peaks for the hemibenzenate XRPD pattern are provided in Table 19. The DSC curve exhibits a broad endotherm near 133° C., associated with ~7.0% of weight loss in the TG thermograph FIG. 23. The weight loss is likely due to the volatilization of benzene (see NMR discussion below), and corresponds to 0.5 moles of benzene for each mole of CDDO-methyl ester. The DSC endotherm observed near 223° C. most likely results from the melt of desolvated material.

These data distinguish previously isolated forms of CDDO-methyl ester from the present invention.

EXAMPLE 9

Characterization of Novel Dimethanolate Form of CDDO-Methyl Ester

A CDDO-methyl ester dimethanol solvate was prepared according to the below procedure. Approximately 500 mg of CDDO-methyl ester was dissolved in 20 mL of methanol at 60° C. The solution was then slowly added to 20 mL of cold methanol at −10° C. with agitation. White solids were collected by vacuum filtration and then stored in a freezer.

Characterization data are summarized in Table 14. Characteristic peaks for the dimethanolate XRPD pattern are provided in Table 18.

Figure 24:
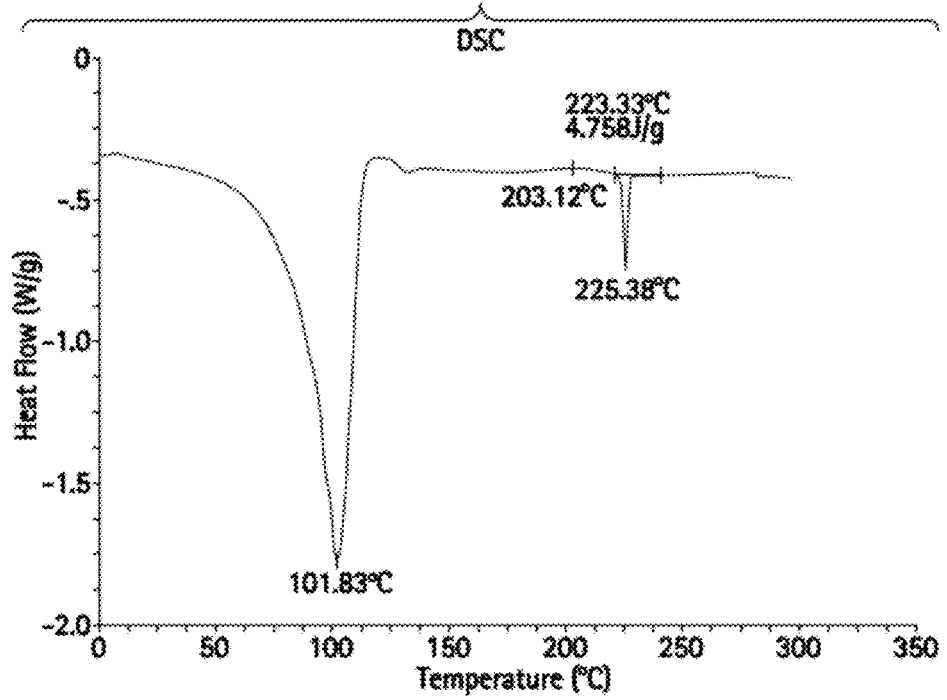
FIG. 24 shows thermograms of CDDO-methyl ester dimethanol solvate.
Figure 24:
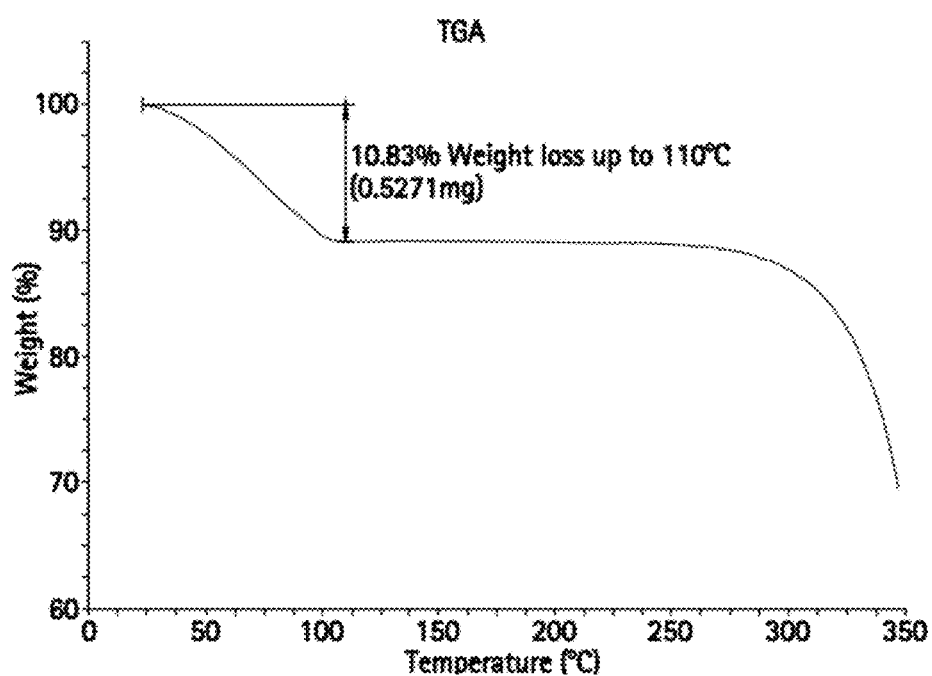
Figure 25:
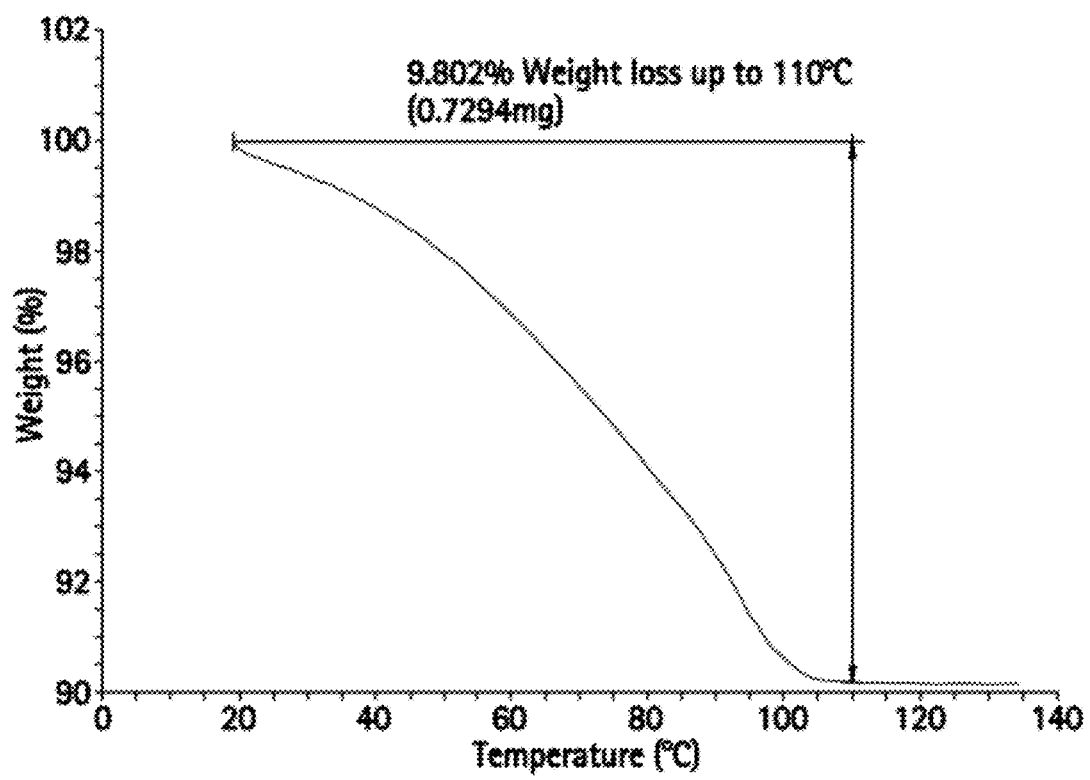
FIG. 25 depicts TGIR data relating to CDDO methyl ester dimethanol solvate.
Figure 26:
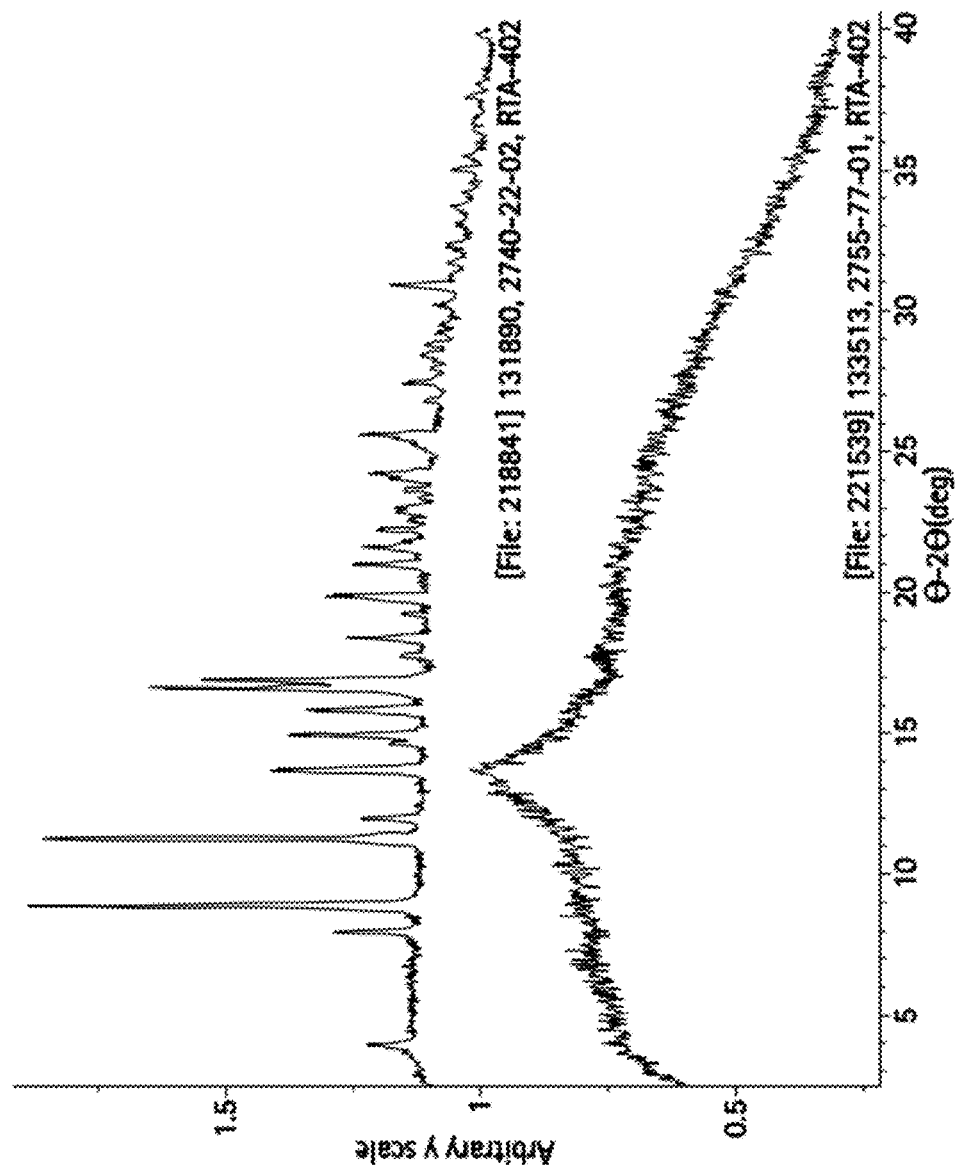
FIG. 26 presents XRPD patterns of CDDO methyl ester dimethanol solvate, before (top) and after (bottom) TGIR analysis (up to 140° C.).

The DSC curve shows a broad endotherm near 102° C., associated with ~11% of weight loss in the TG thermograph (FIG. 24). The TGIR data confirms the weight loss is due to volatilization of ~2.0 moles of methanol (FIG. 25). The resulting material from the TGIR experiment was recovered and was amorphous by XRPD (FIG. 26). A baseline shift at approximately 130° C., a broad exotherm near 203° C. followed by a sharp endotherm (onset: 223° C.) are also observed in the DSC curve. These events are most likely indicative of the Tg of the amorphous material (Form B) obtained through the desolvation of the dimethanol solvate followed by crystallization of the amorphous material to Form A and melting of that crystalline material.

The solution proton NMR spectrum was obtained. The chemical assignments were not performed; however it appears consistent with the chemical structure of CDDO-methyl ester. The peaks at ~3.51 ppm are assigned to methanol and correspond to ~1.7 moles. This result is consistent with the thermal data above.

EXAMPLE 10

Clinical Studies with CDDO-Methyl Ester

CDDO-Me, formulated using micronized Form A, was selected for clinical development and first tested in a Phase I safety-oriented study in patients with advanced cancer who had failed to respond adequately to prior therapies. In this Phase I dose-escalation trial, CDDO-Me was administered to 21 adult patients with various forms of advanced (metastatic) cancer. Patients were administered daily doses of CDDO-Me capsules at doses ranging from 5 to 900 mg/day (specifically 5, 10, 20, 40, 80, 150, 300, 600, or 900 mg/day). CDDO-Me was administered in "cycles" which were repeated until the patient experienced unacceptable toxicity or showed evidence of disease progression. In this study, one cycle of CDDO-Me consisted of 21 consecutive days of dosing followed by a 7-day rest period after which the patient was eligible to start the next cycle.

Both the safety and anti-tumor activity of CDDO-Me were reviewed. In addition, the biological effects of CDDO-Me were characterized. CDDO-Me was very well tolerated in these patients, with no significant drug-related adverse events reported. Several patients (approximately 75% of evaluable patients) were considered to have stable disease (based on standard radiological and clinical criteria) at the first evaluation point following completion of the second treatment cycle. Patients who were found to have evidence of progressive disease before completing the second cycle were not formally evaluated, and were not included in the group of evaluable patients. Five patients, including patients with melanoma and renal cell cancer, continued to show stable disease, some with evidence of regression of individual tumor lesions, after four cycles of treatment. Four patients were considered to have stable disease after at least six cycles of treatment. No new metastases developed in any patient receiving a dose of at least 40 mg CDDO-Me per day according to the prescribed schedule.

Based on the known anti-inflammatory properties of CDDO-Me, circulating inflammatory cytokines were evaluated in patients in the Phase I trial. At doses as low as 5 mg/day, there was a reduction of several circulating pro-inflammatory cytokines and chemokines including MMP-9, TNFα, IL-8, and VEGF. In particular, TNFα, which is known to play a significant role in the inflammatory process of diseases such as rheumatoid arthritis, was reduced substantially or to below detectable limits in 3 patients with elevated baseline TNF levels (one patient each at treatment doses of 10, 20, and 40 mg per day). Unlike anti-TNF monoclonal antibodies, which bind to and render protein targets inactive, CDDO-Me reduces production of TNFα and resultant circulating levels of TNFα.

Additionally, phase 2 gene products, which include antioxidant and detoxification enzymes, have been monitored in peripheral blood mononuclear cells of patients in the Phase I study. Significant induction of NQO1 (NAD(P)H:quinone oxidoreductase), a marker of phase 2 transcriptional activity, has been seen at doses of 10 mg/day and above.

Tumor biopsy data from several patients, taken after two cycles of treatment with CDDO-Me, indicated pronounced reductions in tumor tissue levels of cyclooxygenase-2 (COX-2), inducible nitric oxide synthase (iNOS), and phosphorylated STAT3 (pSTAT3). High levels of expression of each of these proteins are known to be correlated with tumor progression and poor clinical outcomes. Tumor biopsy data in several patients also indicated a pronounced degree of tumor cell death after two cycles of treatment with CDDO-Me. Levels of serum creatinine were significantly lower on day 21, compared to the pre-treatment baseline level, in more than 80% of the patients in this study. A number of patients who continued on treatment for multiple cycles showed continuing reductions in serum creatinine Since serum creatinine is a widely used indicator of renal function, these observations indicate that treatment with CDDO-Me improves kidney function.

These studies provide data in human cancer patients showing the beneficial effect of CDDO-methyl ester on patients suffering from cancer. The data further indicate that CDDO-Me is likely to have clinically useful effects in patients suffering from other inflammation-related diseases, including renal dysfunction.

EXAMPLE 11

Large Scale Production of Form B

Using a Dimethanol Solvate Intermediate

One kilogram of Form A CDDO-Me was dissolved in 60±5° C. methanol to afford a complete solution. The resulting hot solution of CDDO-Me was added to a vessel containing cold −5° C. to −15° C. methanol, while maintaining agitation and a temperature of −5° C. to −15° C. throughout the addition. The resulting suspension of crystalline dimethanol solvate of CDDO-Me was filtered. The resulting solids, which displayed an XRPD pattern consistent with that presented in FIG. 26 (prior to TGIR analysis), were dried in an oven at 70±5° C. Drying was continued until the XRPD profile displayed no reflections characteristic of crystalline substance. The resulting XRPD amorphous CDDO-Me solids were passed through a sieve and packaged. Product recovery ranges from 65-95%.

EXAMPLE 12

Cryo Ground Form A and Form B

Form A was cryoground and analyzed. The measured x-ray data of the sample obtained through cryogrinding (2 hours) showed some broadening in the peak at approximately 13.5°2θ. PDF analysis of cryoground Form A produced results similar to the Form B analysis. These results suggest that the cryoground Form A is a glassy material and that cryogrinding can provide an alternative method for producing Form B.

Form B was cryoground and analyzed. The measured x-ray data of the sample obtained through cryogrinding (1 hour) was similar to the starting Form B material. These results indicate that Form B is stable and does not change Form due to cryogrinding.

TABLE 1

Sample Information

| SAMPLE INFORMATION | DESCRIPTION | XRPD RESULT |
|---|---|---|
| Unmicronized | White powder | A |
| micronized | — | A |

TABLE 2

Approximate Solubilities of CDDO methyl ester

| SOLVENT | SOLUBILITY (mg/mL)[a] |
|---|---|
| Acetone | 70 |
| ACN (acetonitrile) | 66 |
| DCM (dichloromethane) | >194 |
| 1,4-Dioxane | 21 |
| EtOH (ethanol) | 4 |
| EtOAc (ethyl acetate) | 36 |
| Hexanes | <1 |
| (10:1) Isopropanol/water | 4 |
| MeOH (methanol) | 8 |
| MTBE (tert-butyl methyl ether) | 4 |
| THF (tetrahydrofuran) | 97 |
| Toluene | 38 |
| Water | <0.1 |

[a]Solubilities are calculated based on the total solvent used to give a solution; actual solubilities may be greater because of the volume of the solvent portions utilized or a slow rate of dissolution. Solubilities are rounded to the nearest mg/mL.

TABLE 3

Crystallization Experiments on CDDO methyl ester

| SOLVENT | CONDITIONS[a] | HABIT/DESCRIPTION | XRPD RESULT |
|---|---|---|---|
| Acetone | FE | White chunks | A |
|  | SE | White broken glass | Form B |
| (3:10) Acetone/hexanes | SC | No solid | — |
| ACN | FE | White broken glass | A + Form B |
|  | SE | White chunks | A |
| (7:5) ACN/water | SC | Small white blades | A |
| DCM | Rotovap | White broken glass | Form B |
|  | FE | Broken glass | Form B |
|  | SE | White broken glass | Form B |
| (1:5) DCM/hexanes | SC | No solid | — |
| 1,4-Dioxane | FD | Fluffy white solid | Form B |
| EtOH | FE | White chunks | A |
|  | SE | White irregulars | A |
|  | SC | Small white tablets | A |
| EtOAc | FE | White broken glass | Form B |
|  | SE | White broken glass | Form B |
|  | SC | No solid | — |
| (10:1) IPA/water | SC | Small white tablets | A |
| MeOH | FE | White chunks | A |
|  | SE | White tablets, irregulars | A |
|  | SC | Pyramidal tablets | A[b] |
| MTBE | FE | White broken glass | Form B |
|  | SE | White broken glass | Form B |
|  | SC | No solid | — |
| THF | FE | White broken glass | Form B |
|  | SE | White broken glass | Form B |
| (1:2) THF/hexanes | SC | No solid | — |
| Toluene | FE | White chunks | Form B |
|  | SE | White broken glass | Form B |
|  | SC | No solid | — |
| — | Melt/quench | Clear broken glass | Form B |

[a]FE = fast evaporation, SE = slow evaporation, SC = slow cool, temperatures are approximate, FD = freeze dry, rotovap = rotary evaporation
[b]single crystal structure determination

TABLE 4

Slurry Experiments of CDDO methyl ester

| SOLVENT | TIME (DAYS) | HABIT/ DESCRIPTION | XRPD RESULT |
|---|---|---|---|
| (10:1) IPA/water | 7 | White bits | A |
| MTBE | 10 | White chunks | A |
| MeOH | 10 | White chunks | A |

TABLE 5

Cold Precipitation Experiments of CDDO methyl ester

| SOLVENT | ANTISOLVENT | HABIT/ DESCRIPTION | XRPD RESULT |
|---|---|---|---|
| Acetone | Hexanes | No solid | — |
|  | Water | White solid | A |
| DCM | Hexanes | No solid | — |
| THF | Water | White solid | A |

TABLE 6

Characterization Data of Form A

| ANALYTICAL TECHNIQUE | RESULTS[a] |
|---|---|
| XRPD | A |
| DSC | Baseline shift 157° C., endotherm 224° C. |
| TGA | 0.3% weight loss up to 150° C. 1.2% weight loss from 150 to 210° C. |
| KF | 0.38% |
| Hot Stage | 28.9: begin of heating 150.1: — 176.4: — 200.1: no changes 225.9: melting 227.9: melt point |
| MB | Negligible weight change throughout experiment |
| Post MB XRPD | A |
| SEM[b] | Pyramidals, tablets, and plates |
| NMR (CDCl$_3$) | Consistent with structure |

[a]all temperatures are in ° C., endo = endotherm
[b]results based on images taken

TABLE 7

Stress Studies of Form A

| CONDITIONS[a] | HABIT/ DESCRIPTION | XRPD RESULT |
|---|---|---|
| 25° C./60% RH 3 days: 1.5% loss 7 days: 0.6% loss | White powder | A |
| 40° C./75% RH 3 days: 1.4% loss 7 days: 0.2% gain | White powder | A |
| 195° C.[b] 15 minutes: 2% loss | White powder | A |
| 20 min grind, dry | White powder | A |
| 20 min wet grind, water | White powder | A |

TABLE 8

Characterization Data of Form B CDDO methyl ester

| ANALYTICAL TECHNIQUE | RESULTS[a] |
|---|---|
| XRPD | Form B |
| MDSC | Tg ~125° C. |
| NMR (CDCl$_3$) | Consistent with structure |

TABLE 9

Stress Studies of Form B CDDO methyl ester

| CONDITIONS[a] | HABIT/ DESCRIPTION | XRPD RESULT[c] |
|---|---|---|
| 22° C./97% RH 7 days | Broken glass | Form B |
| 40° C./75% RH 8 days | Broken glass | Form B |
| 80° C./0% RH ~24 hours | White broken glass, clear rounded chunks | Form B |
| 195° C.[b] 5 minutes | White fines | Form B |
| 200° C.[b] 60 minutes | White birefringent bits | A + Form B (min) |

[a]RH = relative humidity, Tg = glass transition temperature
[b]Ambient lab humidity was measured as 74% RH
[c]min = minor

TABLE 10

Crystal Data and Data Collection Parameters for Form A

| | |
|---|---|
| formula | C$_{32}$H$_{43}$NO$_4$ |
| formula weight | 505.70 |
| space group | P 43 21 2 (No. 96) |
| a, Å | 14.21620(10) |
| c, Å | 81.5875(12) |
| V, Å$^3$ | 16488.9(3) |
| Z | 24 |
| d$_{calc}$, g cm$^{-3}$ | 1.222 |
| crystal dimensions, mm | 0.01 × 0.01 × 0.00[b] |
| temperature, K | 150. |
| radiation (wavelength, Å) | Mo K$_\alpha$ (0.71073) |
| monochromator | graphite |
| linear abs coef, mm$^{-1}$ | 0.074 |
| absorption correction applied | empirical[a] |
| transmission factors: min, max | 0.9995, 0.9999 |
| diffractometer | Nonius KappaCCD |
| h, k, l range | −15 to 15 −10 to 10 −86 to 72 |
| 2θ range, deg | 4.08-44.43 |
| mosaicity, deg | 0.32 |
| programs used | SHELXTL |
| F$_{000}$ | 6576.0 |
| weighting | 1/[σ$^2$(F$_o^2$) + (0.0176P)$^2$ + 0.0000P] where P = (F$_o^2$ + 2F$_c^2$)/3 |
| data collected | 46742 |
| unique data | 9168 |
| R$_{int}$ | 0.093 |
| data used in refinement | 9168 |
| cutoff used in R-factor calculations | F$_o^2$ > 2.0σ(F$_o^2$) |
| data with I > 2.0σ (I) | 5421 |
| number of variables | 1024 |
| largest shift/esd in final cycle | 0.00 |
| R(F$_o$) | 0.051 |
| R$_w$(F$_o^2$) | 0.085 |
| goodness of fit | 1.045 |

[a]Otwinowski Z. & Minor, W. *Methods Enzymol.*, 1997, 276, 307.
[b]The crystal dimensions are approximate

TABLE 11

Summary of the area under the plasma concentration (AUC) versus time in all animals studied (n = 8) CDDO METHYL ESTER FORMULATION STUDY - PARENT COMPOUND

| Monkey subject # | Form A AUC (ng/ml*hr) | Form B AUC (ng/ml*hr) | % Form B over Form A |
|---|---|---|---|
| 501M | 37.5 | 203.4 | 542 |
| 502M | 28.3 | 204.7 | 723 |
| 503F | 21.3 | 107.3 | 504 |
| 504F | N/A | 175 | N/A |
| 505M | 60.4 | 158.3 | 262 |
| 506M | N/A | N/A | N/A |
| 507F | 57.3 | 164 | 286 |
| 508F | 37.3 | 228 | 611 |
| Mean | 40.4 | 177.2 | 439 |
| Median | 37.4 | 175.0 | 523 |
| Range (min-max) | 21-60.4 | 158-228 | 262-723% |

N/A—not determined.

TABLE 12

Crystallization Experiments of CDDO-methyl ester.

| SOLVENT | CONDITIONS[a] | DESCRIPTION | XRPD RESULT |
|---|---|---|---|
| 10:1 Benzene/acetone | RE, room temperature | White solids | X-ray amorphous |
| 10:1 Benzene/acetone | FE followed by drying at 60° C. | Clear gel | — |
| 10:1 Benzene/acetone | FE w/capillaries | Clear film | — |
| 10:1 Benzene/acetone | FE, capped and put in a freezer over night, scratched the vial using a metal spatula and left to evaporate at room temperature | White solid | Benzene solvate |
| 10:1 Benzene/acetone | FE, capped and sitting at room temperature over night, scratched the vial using a metal spatula and left to evaporate at room temperature | White solid | Benzene solvate |
| 10:1 Benzene/acetone | FE w/sonication | White solids | Benzene solvate |

[a]RE = rotary evaporation, FE = fast evaporation

TABLE 13

Characterization of CDDO-methyl ester Hemibenzene Solvate

| ANALYTICAL TECHNIQUE | RESULTS |
|---|---|
| XRPD | Hemibenzene solvate |
| DSC, 10° C./min | Endotherm 133° C. |
| | Endotherm 223° C. (onset 221° C.) |
| TG, 10° C./min | 7.0% weight loss up to 160° C. |
| | Corresponds to 0.5 moles of benzene |
| $^1$H NMR (CDCl$_3$) | Consistent with structure |
| | ~0.5 moles of benzene evident |

TABLE 14

Characterization of CDDO-methyl ester Dimethanol Solvate

| ANALYTICAL TECHNIQUE | RESULTS |
|---|---|
| XRPD | Dimethanol solvate |
| DSC, 10° C./min | Endotherm 102° C. |
| | Baseline shift at 130° C. |
| | Broad exotherm 203° C. |
| | Endotherm 225° C. (onset: 223° C.) |
| TG, 10° C./min | 11% weight loss up to 110° C. |
| | Corresponds to ~2.0 moles of methanol |
| TGIR, 20° C./min | 9.8% weight loss up to 110° C. |
| | Corresponds to ~1.7 moles of methanol |
| | Volatile component identified as methanol |
| Post TGIR XRPD | X-ray amorphous |
| IR | Consistent with structure |
| $^1$H NMR (CDCl$_3$) | Consistent with structure |
| | ~1.7 moles of methanol evident |

TABLE 15

Stress Studies of Micronized Form B CDDO-methyl ester

| | FORM B PRODUCED VIA EXAMPLE 11 PROCEDURE | | FORM B PRODUCED BY ISOLATION FROM ETHYL ACETATE AND ETHANOL MIXTURES | |
|---|---|---|---|---|
| Stress Conditions[a] | XRPD Result | KF Result | XRPD Result | KF Result |
| 80° C./P$_2$O$_5$, 14 d | Form B | NP | NP | NP |
| 80° C./P$_2$O$_5$, 28 d | Form B | 1.10 | 100% Form A | 0.37 |
| 60° C./23% RH, 28 d | Form B | 0.04 | ~50% Form A + Form B | 0.02 |
| 40° C./48% RH, 28 d | Form B | 0.00[b] | Form B | 0.39 |
| 25° C./75% RH, 14 d | Form B | NP | NP | NP |
| 25° C./75% RH, 28 d | Form B | 0.77 | Form B | 0.58 |

[a]RH = relative humidity
[b]Actual value was negative

TABLE 20

Solutions prepared for spray drying

| SOLID RATIO | 40% Form B, 60% Polymer | 60% Form B, 40% Polymer |
|---|---|---|
| POLYMER | Methacrylic acid copolymer Type C | HPMCP HP-55 |
| SOLVENT | Acetone | Acetone |
| CONC. % W/W | 10 | 10 |
| TEMPERATURE ° C. | −20 | −20 |
| OBSERVATIONS | Solution showed some haziness after the charge of the polymer. A sample of the solution was heated up to 35/40° C., but the haziness didn't disappear and some flocculation was observed.. | The solution was completely clear after the charge of the polymer. The two runs done used the solution in the same day that it was prepared. |

TABLE 16

CDDO-Me Single Agent Anticancer Activity

| MODEL | AGENT/ ROUTE | DRUG ACTIVITY | COMMENTS |
|---|---|---|---|
| NCI-H460 Lung Cancer Xenograft (nude rat) | CDDO-Me, p.o. | 78% TGI [1] | Dose-dependent effects. CDDO-Me as effective as radiation |
| MCF-7/Her-2 Breast Cancer Xenograft (nude mouse) | CDDO-Me, i.v. | 15% regression | Superior results achieved in tumors that over-express Her-2 [a] |
| 4T1 Syngeneic Breast Cancer Metastasis Model (mouse) - Early Treatment | CDDO-Me, i.v. | 100% suppression | All animals remained tumor-free at sacrifice on Day 85 [b] |
| 4T1 Syngeneic Breast Cancer Metastasis Model (mouse) - Delayed Treatment | CDDO-Me, i.v. | 67% suppression | 33% of animals tumor-free at sacrifice on Day 95 [2] |
| L3.6PL Pancreatic Cancer Xenograft (nude mouse) | CDDO-Me, i.v. | 51% TGI | CDDO-Me outperformed Gemcitabine |
| DU-145 Prostate Cancer Xenograft (nude rat) | CDDO-Me, p.o. | 77% TGI | Multiple schedules tested - TGI 60-77% |

[1] TGI = Tumor Growth Inhibition
Data presented is from doses at or below the MTD (defined as ≤10% mortality and ≤20% weight loss).
[a] Konopleva, et al., "Synthetic triterpenoid 2-cyano-3,12-dioxooleana-1,9-dien-28-oic acid induces growth arrest in HER2-overexpressing breast cancer cells," *Mol Cancer Ther.* 2006, 5: 317-28.
[b] Ling, et al, "The novel triterpenoid C-28 methyl ester of 2-cyano-3,12-dioxoolen-1,9-dien-28-oic acid inhibits metastatic murine breast tumor growth through inactivation of STAT3 signaling," *Cancer Res.* 2007, 67: 4210-8.

TABLE 21

Characteristics of tested formulations

| Polymer | Methacrylic acid copolymer, Type C | HPMCP HP-55 |
|---|---|---|

Tests

| | | |
|---|---|---|
| Description | White solid | White solid |
| X-Ray Powder Diffraction | No crystalline peak detected | No crystalline peak detected |
| Water | 1.50% w/w | — |
| DSC - Tg (inflection point) | 106° C. | 118° C. |
| Assay (by HPLC) | 409% w/w (calculated on the anhydrous and solvent free basis) | 59.4% w/w (calculated on the anhydrous and solvent free basis) |
| Total of impurities (HPLC)ti | 1.14% area | 0.42% area |
| Particle size (D50) | 21 pm | |
| Bulk density | 0.18 g/cm$^3$ (calculated with 4 g of product) | 0.19 g/cm$^3$ (calculated with 4 g of product) |

TABLE 22

Mean Concentrations of CDDO-Me in Plasma of Cynomolgus Monkeys in Phase 2 and 3 Samples Mean concentrations of CDDO-methyl ester (ng/mL)

| Time | PO Form A (nanocrystalline) | PO Form B (micronized) | PO Form A (crystalline micronized) | PO Form B (PVP/VA) | PO Form B (HPMCP) | PO Form B (Eudragit L100-55) |
|---|---|---|---|---|---|---|
| Pre-dose | BLQ | BLQ | BLQ | BLQ | BLQ | BLQ |
| 5 min | NST | NST | NST | NST | NST | NST |
| 10 min | NST | NST | NST | NST | NST | NST |
| 15 min | NST | NST | NST | NST | NST | NST |
| 30 min | NST | NST | NST | NST | NST | NST |
| 1 h | *1.53 ± 1.49* | *6.01 ± 5.67* | *0.619 ± 0.207* | 9.45 ± 3.64 | *9.94 ± 4.83* | 9.06 ± 4.38 |
| 2 h | 3.00 ± 2.02 | 14.5 ± 9.63 | *0.505 ± 0.260* | 14.8 ± 3.04 | 24.1 ± 13.2 | 22.2 ± 11.7 |
| 4 h | 3.52 ± 1.30 | 32.0 ± 11.6 | *1.15 ± 0.73* | 27.3 ± 3.79 | 50.7 ± 10.0 | 50.6 ± 19.3 |
| 8 h | 8.56 ± 2.32 | 33.3 ± 8.44 | 4.31 ± 1.35 | 30.4 ± 10.8 | 40.0 ± 15.6 | 51.1 ± 8.72 |
| 16 h | 7.90 ± 2.26 | 14.2 ± 5.68 | 5.39 ± 1.12 | 13.3 ± 3.92 | 15.4 ± 7.41 | 25.6 ± 13.9 |
| 24 h | 4.40 ± 2.33 | 5.23 ± 1.86 | 3.05 ± 1.42 | 6.39 ± 2.02 | 5.79 ± 2.95 | 7.47 ± 4.10 |
| 36 h | NST | NST | NST | NST | NST | NST |
| 48 h | *0.649 ± 0.342* | *0.576 ± 0.175* | *0.419 ± 0.291* | *1.78 ± 1.61* | *0.983 ± 0.343* | *1.37 ± 0.626* |
| 72 h | *0.312 ± 0.390* | *0.408 ± 0.368* | *0.0169 ± 0.0252* | *0.395 ± 0.319* | *0.448 ± 0.283* | *0.344 ± 0.461* |

NST No sample taken.

BLQ Below limit of quantification (1.00 ng/mL).

IV Intravenous administration.

PO Oral administration by capsule.

Values in bold italics calculated using all values presented in Appendix 3, consequently the mean may differ from means calculated where values that are BLQ are assumed to be zero.

Cited Publications

1. Sheldrick, G. M. SHELX97, A Program for Crystal Structure Refinement, University of Gottingen, Germany (1997).
2. Otwinowski, Z.; Minor, W. *Methods Enzymol.* 1997, 276, 307.
3. Bruker, XPREP in SHELXTL v. 6.12., Bruker AXS Inc., Madison, Wis. (2002).
4. Bruno, et al., *Acta Crystallogr.* 2002, B58, 389
5. International Tables for Crystallography, Vol. C, Tables 4.2.6.8 and 6.1.1.4, Kluwer Academic Publishers: Dordrecht, The Netherlands (1992).
6. Kraus, W., and G. Nolze, PowderCell for Windows Version 2.3, Federal Institute for Materials Research and Testing, Berlin (1999).
7. Johnson, C. K. ORTEPIII, Report ORNL-6895, Oak Ridge National Laboratory, TN, U.S.A. 1996.
8. Watkin, D. J.; Prout, C. K.; Pearce, L. J. Cameron, Chemical Crystallography Laboratory, University of Oxford, Oxford, 1996.
9. OPTEP-3 for Windows V1.05 ,. Farrugia, L. J., *J. Appl. Cryst.* 1997, 30, 565.
10. Bore, et al., *Acta Cryst.* 2002, C58, o199-o200.
11. Honda, et al., *Bioorganic & Medicinal Chemistry Letters* 1997, 7, 1623.
12. Honda, et al, *loc. cit.* 1998, 8, 2711-14.
13. Honda, et al., J. Med. Chem. 2000, 43, 1866.
14. Honda, et al., loc. cit., 4233.
15. Honda, et al., *Bioorganic & Medicinal Chemistry Letters* 2002, 12, 1027.
16. Zhou, et al., *J. Pharmaceutical Sciences* 2002, 91, 1863.
17. Cui et al., *Int'l J. Pharmaceutics,* 2007 339, 3-18.
18. Repka et al., Hot-melt extrusion technology In: Enclopedia of Pharmaceutical Technology, 2$^{nd}$ ed (Marcel Dekker, 2002), pages 203-06.

What is claimed is:

1. Anhydrous, crystalline methyl 2-cyano-3,12-dioxoleana-1,9(11)-dien-28-oate (CDDO-methyl ester) characterized in that its X-ray powder diffractogram comprises peaks at 8.78° 2θ, 12.94° 2θ, 13.35° 2θ, 14.18° 2θ, and 17.4° 2θ±0.2° 2θ based upon data collected on a diffractometer with Cu K$_\alpha$ radiation.

2. The CDDO-methyl ester according to claim 1, wherein the X-ray powder diffractogram is substantially as shown in FIG. 18.

3. The CDDO-methyl ester according to claim 1, further characterized in that its differential scanning calorimetry curve comprises a baseline shift at approximately 157° C. and an endotherm maximum at about 224° C.

4. The CDDO-methyl ester according to claim 3, wherein the differential scanning calorimetry curve is substantially as shown in FIG. 3.

5. A pharmaceutical composition comprising a therapeutically effective amount of the CDDO-methyl ester according to claim 1 and one or more solid pharmaceutically acceptable carriers.

6. The pharmaceutical composition according to claim 5, wherein the CDDO-methyl ester is micronized and the solid pharmaceutically acceptable carriers are edible carriers.

7. A method for treating a chronic inflammatory condition in a subject suffering therefrom, comprising administering to the subject a therapeutically effective amount of CDDO-methyl ester according to claim 1.

8. Crystalline CDDO-methyl ester hemibenzenate, characterized in that its X-ray powder diffractogram comprises peaks at 9.25° 2θ, 14.17° 2θ, , 14.62° 2θ, 16.32°2θ, and 17.11° 2θ±0.2° 2θ based upon data collected on a diffractometer with Cu K$_\alpha$ radiation.

9. The crystalline CDDO-methyl ester hemibenzenate according to claim 8, further characterized in that it has a differential scanning calorimetry curve as substantially shown in FIG. 23.

* * * * *